United States Patent
Berta et al.

(10) Patent No.: US 7,105,535 B2
(45) Date of Patent: Sep. 12, 2006

(54) OXAZOLYL-PYRAZOLE DERIVATIVES AS KINASE INHIBITORS

(75) Inventors: Daniela Berta, Sassari (IT); Eduard Felder, Mendrisio (CH); Anna Vulpetti, Brugherio (IT); Marzia Villa, Bologna (IT)

(73) Assignee: Pfizer Italia S.R.L., Rome (IT)

( * ) Notice: Subject to any disclaimer, the term of this patent is extended or adjusted under 35 U.S.C. 154(b) by 248 days.

(21) Appl. No.: 10/470,859

(22) PCT Filed: Jan. 28, 2002

(86) PCT No.: PCT/EP02/00995

§ 371 (c)(1),
(2), (4) Date: Apr. 15, 2004

(87) PCT Pub. No.: WO02/062804

PCT Pub. Date: Aug. 15, 2002

(65) Prior Publication Data

US 2004/0180881 A1    Sep. 16, 2004

(30) Foreign Application Priority Data

Feb. 2, 2001  (GB) ................................ 0102687.1

(51) Int. Cl.
  *A61K 31/302*  (2006.01)
  *A61K 31/338*  (2006.01)
  *A61K 31/375*  (2006.01)
  *C07D 471/04*  (2006.01)
  *C07D 471/06*  (2006.01)
(52) U.S. Cl. ...................... 514/302; 514/338; 514/375; 548/217; 546/271.7; 546/115; 546/270.4
(58) Field of Classification Search ................ 548/217; 546/115, 271.7, 270.4, 156; 514/375, 302, 514/338
See application file for complete search history.

(56) References Cited

FOREIGN PATENT DOCUMENTS

| DE | 3722992 A1 | 1/1989 |
| WO | WO 98/52940 A1 | 11/1998 |
| WO | WO 99/58523 A1 | 11/1999 |

OTHER PUBLICATIONS

El-Maghraby et al. Indian Journal of Chemistry, Section B 1978, 16B(1), p. 57-59 *CAS Abstract Attached.*
International Search Report for PCT/EP02/00995, 2 pages, (Jun. 2002).
Philip Cohen, "*The development and therapeutic potential of protein kinase inhibitors,*" Current Opinion in Chemical Biology, vol. 3, pp. 459-465, (1999).
Meanwell, et al. "*Nonprostaniod Prostacyclin Mimetics. 5. Structure-Activity Relationsips Associated with [3-[4-(4,5-Diphenyl-2-oxazolyl)-5-oxazolyl]phenoxy]acetic Acid,*" Journal of Medicinal Chemistry, pp. 3884-3903, (1993).
Mustafa M. El-Abadelah, Thienopyridinone antibacterials: Synthesis and antibacterial activity of some 7-aryl-2-chloro-4,7-dihydro-4-oxothieno[2,3-b]pyridine-5-carboxylic acids, Eur. J. Med. Chem., 33, 33-42, (1998).
Tomoko Hosoi, Evidence for cdk5 as a Major Activity Phosphorylating Tau Protein in Porcine Brain Extract, J. Biochem., 117, 741-749, (1995).

\* cited by examiner

*Primary Examiner*—Kamal A. Saeed
*Assistant Examiner*—Jason M. Nolan
(74) *Attorney, Agent, or Firm*—Scully, Scott, Murphy & Presser, P.C.

(57) ABSTRACT

Compounds which are oxazolyl-pyrazole derivatives, as defined in the specification, and pharmaceutically acceptable salts thereof; are useful in the treatment of diseases caused by and/or associated with an altered protein kinase activity such as cancer, cell proliferative disorders, viral infections, autoimmune diseases and neurodegenerative disorders.

27 Claims, No Drawings

OXAZOLYL-PYRAZOLE DERIVATIVES AS KINASE INHIBITORS

BACKGROUND OF THE INVENTION

1. Field of the Invention

The present invention relates to pyrazole derivatives active as kinase inhibitors and, more in particular, it relates to oxazolyl-pyrazole derivatives, to a process for their preparation, to pharmaceutical compositions comprising them and to their use as therapeutic agents, particularly in the treatment of diseases linked to disregulated protein kinases.

2. Discussion of the Background

The malfunctioning of protein kinases (PKs) is the hallmark of numerous diseases.

A large share of the oncogenes and proto-oncogenes involved in human cancers code for PKs. The enhanced activities of PKs are also implicated in many non-malignant diseases such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or disregulation see, for instance, Current Opinion in Chemical Biology 1999, 3, 459–465.

SUMMARY OF THE INVENTION

The present inventors have now discovered that some oxazolyl-pyrazoles are endowed with multiple protein kinase inhibiting activity and are thus useful in therapy in the treatment of diseases caused by and/or associated with disregulated protein kinases.

As such, it is an object of the invention to provide compounds which are useful as therapeutic agents against a host of diseases caused by a disregulated protein kinase activity.

It is another object to provide compounds which are endowed with multiple protein kinase inhibiting activity.

More specifically, the oxazolyl-pyrazoles of this invention are useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Due to the key role of PKs in the regulation of cellular proliferation, these oxazolyl-pyrazoles are also useful in the treatment of a variety of cell proliferative disorders such as, for instance, benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

The compounds of the invention can be useful in the treatment of Alzheimer's disease, as suggested by the fact that cdk5 is involved in the phosphorylation of tau protein (J. Biochem., 117, 741–749, 1995).

The compounds of this invention, as modulators of apoptosis, may also be useful in the treatment of cancer, viral infections, prevention of AIDS development in HIV-infected individuals, autoimmune diseases and neurodegenerative disorders.

The compounds of this invention may be useful in inhibiting tumor angiogenesis and metastasis.

The compounds of the invention are useful as cyclin dependent kinase (cdk) inhibitors and also as inhibitors of other protein kinases such as, for instance, protein kinase C in different isoforms, Met, PAK-4, PAK-5, ZC-1, STLK-2, DDR-2, Aurora 1, Aurora 2, Bub-1, PLK, Chk1, Chk2, HER2, raf1, MEK1, MAPK, EGF-R, PDGF-R, FGF-R, IGF-R, VEGF-R, PI3K, weel kinase, Src, Abl, Akt, ILK, MK-2, IKK-2, Cdc7, Nek, and thus be effective in the treatment of diseases associated with other protein kinases.

Accordingly, the present invention provides a method for treating diseases caused by and/or associated with an altered protein kinase activity which comprises administering to a mammal in need thereof an effective amount of an oxazolyl-pyrazole derivative represented by formula (I):

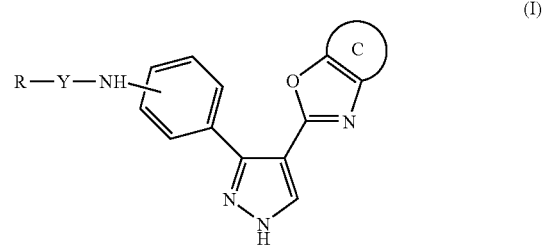

wherein

R represents a hydrogen atom; a straight or branched $C_1$–$C_8$ alkyl group; a straight or branched $C_2$–$C_8$ alkenyl group; an aryl or aryl $C_1$–$C_6$ alkyl group; a saturated or unsaturated $C_3$–$C_6$ cycloalkyl or cycloalkyloxy group optionally further condensed with 1 or 2 benzene rings; or it is an optionally benzocondensed 5 or 6 membered heterocyclic or heterocyclyl $C_1$–$C_6$ alkyl group, having 1 or 2 heteroatoms selected among nitrogen, oxygen or sulfur; each of the above defined R groups being optionally further substituted by one or more groups selected from:

i) halogen, nitro, cyano, hydroxy, oxo groups (=O);

ii) straight or branched $C_1$–$C_6$ alkyl, alkoxyalkyl or perfluorinated alkyl;

iii) aryl or 5 or 6 membered heterocycles having 1 or 2 heteroatoms selected among nitrogen, oxygen or sulfur, optionally substituted by halogen, nitro, cyano, $C_1$–$C_6$ alkyl or alkoxy;

iv) straight or branched $C_1$–$C_6$ alkoxy, alkoxyalkyloxy, arylalkyloxy or aryloxy optionally substituted by halogen, nitro, cyano, $C_1$–$C_6$ alkyl or alkoxy;

v) straight or branched $C_1$–$C_6$ alkylthio or alkylsulphonyl, arylthio or arylsulphonyl;

vi) $C_3$–$C_6$ cycloalkyl;

vii) amino, $C_1$–$C_6$ alkylamino, dialkylamino or arylamino;

viii) $C_1$–$C_6$ alkylcarbonyl, alkyloxycarbonyl, alkylaminocarbonyl, aminocarbonyl, arylcarbonyl or heterocyclylcarbonyl optionally substituted by halogen, nitro, cyano, $C_1$–$C_6$ alkyl or alkoxy;

ix) $C_1$–$C_6$ alkylcarbonylamino, alkyloxycarbonylamino, arylalkyloxycarbonylamino, arylcarbonylamino or aryloxycarbonylamino;

x) carboxy, $C_1$–$C_6$ alkylcarbonyloxy or arylcarbonyloxy;

Y is a single bond or a divalent group selected from carbonyl (>C=O), aminocarbonyl (—NHCO—) or sulphonyl (—SO$_2$—);

C is benzene, naphthalene or an optionally benzocondensed 5 or 6 membered heterocycle having 1 or 2 heteroatoms selected among nitrogen, oxygen or sulphur; each of which being optionally further substituted by one or more groups selected from halogen, nitro, cyano, straight or branched $C_1$–$C_6$ alkyl or alkoxy, alkylsulphonyl or aryl groups;

or a pharmaceutically acceptable salt thereof.

In a preferred embodiment of the method described above, the disease caused by and/or associated with an altered protein kinase activity is selected from the group consisting of cancer, cell proliferative disorders, Alzheimer's disease, viral infections, auto-immune diseases and neurodegenerative disorders.

Specific types of cancer that may be treated according to the invention include carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderoma pigmentosum, keratoxanthoma, thyroid follicular cancer and Kaposi's sarcoma In another preferred embodiment of the method described above, the cell proliferative disorder is selected from the group consisting of benign prostate hyperplasia, familial adenomatosis polyposis, neuro-fibromatosis, psoriasis, vascular smooth cell proliferation associated with atherosclerosis, pulmonary fibrosis, arthritis glomerulonephritis and post-surgical stenosis and restenosis. In addition, the method object of the present invention, provides tumor angiogenesis and metastasis inhibition.

The present invention also provides an oxazolyl-pyrazole derivative represented by formula (I):

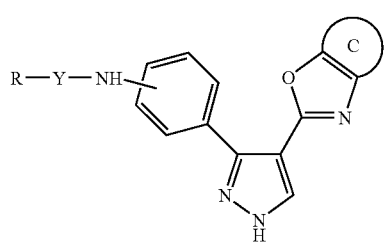

(I)

wherein

R represents a hydrogen atom; a straight or branched $C_1$–$C_8$ alkyl group; a straight or branched $C_2$–$C_8$ alkenyl group; an aryl or aryl $C_1$–$C_6$ alkyl group; a saturated or unsaturated C3–$C_6$ cycloalkyl or cycloalkyloxy group optionally further condensed with 1 or 2 benzene rings; or it is an optionally benzocondensed 5 or 6 membered heterocyclic or heterocyclyl $C_1$–$C_6$ alkyl group, having 1 or 2 heteroatoms selected among nitrogen, oxygen or sulfur; each of the above defined R groups being optionally further substituted by one or more groups selected from:

i) halogen, nitro, cyano, hydroxy, oxo groups (=O);

ii) straight or branched $C_1$–$C_6$ alkyl, alkoxyalkyl or perfluorinated alkyl;

iii) aryl or 5 or 6 membered heterocycles having 1 or 2 heteroatoms selected among nitrogen, oxygen or sulfur, optionally substituted by halogen, nitro, cyano, $C_1$–$C_6$ alkyl or alkoxy;

iv) straight or branched $C_1$–$C_6$ alkoxy, alkoxyalkyloxy, arylalkyloxy or aryloxy optionally substituted by halogen, nitro, cyano, $C_1$–$C_6$ alkyl or alkoxy;

v) straight or branched $C_1$–$C_6$ alkylthio or alkylsulphonyl, arylthio or arylsulphonyl;

vi) $C_3$–$C_6$ cycloalkyl;

vii) amino, $C_1$–$C_6$ alkylamino, dialkylamino or arylamino;

viii) $C_1$–$C_6$ alkylcarbonyl, alkyloxycarbonyl, alkylaminocarbonyl, aminocarbonyl, arylcarbonyl or heterocyclylcarbonyl optionally substituted by halogen, nitro, cyano, $C_1$–$C_6$ alkyl or alkoxy;

ix) $C_1$–$C_6$ alkylcarbonylamino, alkyloxycarbonylamino, arylalkyloxycarbonylamino, arylcarbonylamino or aryloxycarbonylamino;

x) carboxy, $C_1$–$C_6$ alkylcarbonyloxy or arylcarbonyloxy;

Y is a single bond or a divalent group selected from carbonyl (>C=O), aminocarbonyl (—NHCO—) or sulphonyl (—SO$_2$—);

C is benzene, naphthalene or an optionally benzocondensed 5 or 6 membered heterocycle having 1 or 2 heteroatoms selected among nitrogen, oxygen or sulphur; each of which being optionally further substituted by one or more groups selected from halogen, nitro, cyano, straight or branched $C_1$–$C_6$ alkyl or alkoxy, alkylsulphonyl or aryl groups;

or a pharmaceutically acceptable salt thereof.

The oxazolyl-pyrazole derivatives of formula (I), object of the invention, are obtainable through a synthetic process comprising well known reactions carried out according to conventional techniques, as well as through a new and extremely versatile solid-phase combinatorial process, being both comprised within the scope of the invention.

The present invention also provides a pharmaceutical composition comprising the oxazolyl-pyrazole derivatives of formula (I) and at least one pharmaceutically acceptable excipient, carrier or diluent.

A more complete appreciation of the invention and many of the attendant advantages thereof will be readily obtained as the same becomes better understood by reference to the following detailed description.

DETAILED DESCRIPTION OF THE INVENTION

Some heteroaryl-pyrazole derivatives structurally close to the compounds of formula (I) are known in the art. Among them are, as an example, certain imidazolyl-pyrazoles active as cardiovascular agents (DE 3722992 by Dr. Karl Thomae). Imidazolyl-pyrazoles wherein the imidazole moiety is part of a purine bicyclic system, active as p38 kinase inhibitors, are also disclosed in the international patent application WO 98/52940 in the name of G. D. Searle and Co.

The compounds of formula (I), object of the present invention, may have asymmetric carbon atoms and may therefore exist either as racemic admixtures or as individual optical isomers. Accordingly, all the possible isomers and their admixtures and of both the metabolites and the pharmaceutically acceptable bio-precursors (otherwise referred to as pro-drugs) of the compounds of formula (I), as well as any therapeutic method of treatment comprising them, are also within the scope of the present invention.

In addition to the above, as it will be readily appreciated, the unsubstituted ring nitrogen pyrazoles in the compounds of the invention are known to rapidly equilibrate, in solution, as admixtures of both tautomers:

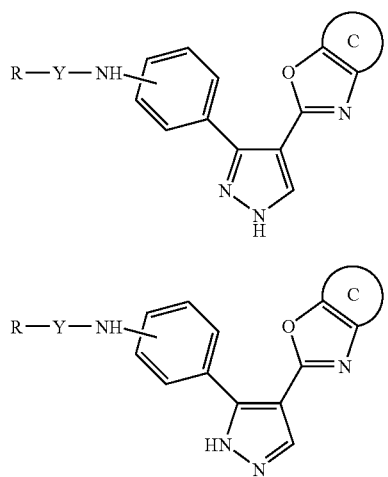

Accordingly, in the present invention and unless otherwise indicated, where only one tautomer is indicated for the compounds of formula (I), the other, (Ia), is also within the scope of the present invention.

As used herein, unless otherwise specified, with the term straight or branched $C_1$–$C_8$ alkyl, hence also comprising $C_1$–$C_6$ alkyl, we intend a group such as, for instance, methyl, ethyl, n-propyl, isopropyl, n-butyl, isobutyl, sec-butyl, tert-butyl, n-pentyl, neopentyl, n-hexyl, isohexyl, n-heptyl, 2-methyl-hexyl-2-yl, n-octyl, and the like. With the term straight or branched $C_2$–$C_8$ alkenyl we intend a group such as, for instance, vinyl, 1- or -2-propenyl, isopropenyl, 1-, 2- or 3-butenyl, pentenyl, hexenyl, heptenyl, octenyl and the like.

With the term aryl we intend an aromatic carbocycle such as, for instance, phenyl, biphenyl, 1-naphthyl, 2-naphthyl, and the like.

With the term saturated or unsaturated $C_3$–$C_6$ cycloalkyl or cycloalkyloxy group we intend, for instance, cyclopropyl, cyclobutyl, cyclopentyl, cyclohexyl, cyclopentenyl, cyclohexenyl, cyclopentyloxy, cyclohexyloxy and the like.

Unless otherwise specified, saturated or unsaturated cycloalkyl groups further condensed with 1 or 2 benzene rings are, for instance, 1,2,3,4-tetrahydro-naphthalene-2-yl, fluorene-9-yl, and the like.

With the term 5 or 6 membered heterocycle with 1 or 2 heteroatoms selected among nitrogen, oxygen or sulphur, we intend a saturated, partly unsaturated or fully unsaturated either aromatic or non aromatic heterocycle such as, for instance, thiophene, furan, pyrrole, imidazole, pyrazole, thiazole, isothiazole, oxazole, isoxazole, pyridine, pyrazine, pyrimidine, pyridazine, pyrrolidine, pyrroline, imidazolidine, imidazoline, piperidine, piperazine, morpholine, tetrahydrofuran, tetrahydropyran, tetrahydrothiopyran, and the like.

With the term optionally benzocondensed heterocycle and unless otherwise indicated we intend any of the above defined heterocycles further condensed, through any one of the available bonds, with benzene rings such as, for instance, quinoline, isoquinoline, chroman, chromene, thionaphthene, indoline, and the like.

As far as the C group is concerned, it represents either a mono-cyclic or bi-cyclic ring system being condensed, through any one of its available bonds, to the oxazole ring in formula (I).

As above indicated, C may represent a benzene ring or a naphthalene group linked to the rest of the molecule through any one of its bonds, for instance the bond in position 1,2 or 2,3 of the naphthalene moiety. Alternatively, C may represent an optionally benzocondensed 5 or 6 membered heterocycle, as above indicated.

According to the meanings provided to R and C, any of the said groups may be optionally further substituted, in any of the free positions, by one or more groups as above indicated.

In this respect, unless otherwise indicated, with the term halogen atom we intend a fluorine, chlorine, bromine or iodine atom.

With the term oxo we intend a carbonyl (>C=O) group.

With the term perfluorinated alkyl we intend any alkyl group as above defined being substituted by two or more fluorine atoms such as, for instance, trifluoromethyl, 2,2,2-trifluoroethyl, 1,1-difluoroethyl, and the like.

From all of the above, it is clear to the skilled man that any of the groups or substituents being defined, for instance, as arylalkyl, heterocyclylalkyl, alkylaryl, alkoxy, alkoxyalkyloxy, arylalkyloxy, alkylaminocarbonyl, heterocyclylcarbonyl, alkylamino, arylamino, alkylthio, arylthio, alkylsulphonyl, arylsulphonyl and the like, have to be construed from the names of the groups from which they originate.

As an example, unless specifically noted otherwise, any arylalkyloxycarbonylamino group has to be intended as a carbonylamino group being substituted by alkyloxy wherein the alkyl moiety is further substituted by aryl, both aryl and alkyl being as above defined.

Pharmaceutically acceptable salts of the compounds of formula (I) are the acid addition salts with inorganic or organic, e.g. nitric, hydrochloric, hydrobromic, sulphuric, perchloric, phosphoric, acetic, trifluoroacetic, propionic, glycolic, lactic, oxalic, malonic, malic, maleic, tartaric, citric, benzoic, cinnamic, mandelic, methanesulphonic, isethionic and salicylic acid, as well as the salts with inorganic or organic bases, e.g. alkali or alkaline-earth metals, especially sodium, potassium, calcium or magnesium hydroxides, carbonates or bicarbonates, acyclic or cyclic amines, preferably methylamine, ethylamine, diethylamine, triethylamine or piperidine.

Within the compounds of formula (I) object of the invention, the R—Y—NH— group can be in position 2 (ortho), 3 (meta) or 4 (para) of the phenylene moiety with respect to the pyrazole ring; preferably, the said R—Y—NH group is in position meta or para.

Preferred compounds of formula (I) are the compounds wherein R is selected from straight or branched $C_1$–$C_8$ alkyl or $C_2$–$C_6$ alkenyl, aryl, aryl $C_1$–$C_6$ alkyl or 5 or 6 membered heterocyclyl, saturated or unsaturated $C_3$–$C_6$ cycloalkyl or cycloalkyloxy optionally further condensed as above defined, or optionally benzocondensed 5 or 6 membered heterocycle having 1 or 2 heteroatoms selected among nitrogen, oxygen or sulfur; each of which being optionally substituted as above defined; Y is a divalent group selected from carbonyl (>C=O), aminocarbonyl (—NHCO—) or sulphonyl (—SO$_2$—); and C is a benzene or a naphthalene ring or it is a 5 or 6 membered heterocycle with 1 or 2 heteroatoms selected among nitrogen, oxygen and sulfur, each of which being optionally further substituted as above defined.

Still more preferred, within this class, are the compounds of formula (I) wherein R is a straight or branched $C_1$–$C_8$ alkyl or $C_2$–$C_6$ alkenyl, phenyl, phenyl $C_1$–$C_6$ alkyl, 1-naphthyl, 2-naphtyl, biphenyl, pyridyl, pyrazolyl, thienyl, isoxazolyl, thiazolyl, pyrazolyl, cyclopropyl, cyclobutyl, cyclopentyl, fluorene-9-yl, cyclohexyl, cyclohexyloxy, cyclohexenyl, tetrahydronaphtyl, piperidine or tetrahydroquinoline; each of which being optionally further substituted as above indicated; Y is a divalent group selected from carbonyl (>C=O), aminocarbonyl (—NHCO—) or sulphonyl (—SO$_2$—); and C is a benzene, naphthalene or pyridine ring, each of which being optionally further substituted as above indicated.

According to a preferred embodiment of the invention, the compounds of formula (I) are amido derivatives wherein R and C are as above defined and Y is a divalent carbonyl (>C=O) group.

According to another preferred embodiment of the invention, the compounds of formula (I) are ureido derivatives wherein R and C are as above defined and Y is a divalent aminocarbonyl (—NHCO—) group.

According to another still preferred embodiment of the invention, the compounds of formula (I) are sulphonamido derivatives wherein R and C are as above defined and Y is a divalent sulphonyl (—SO$_2$—) group.

Specific, not limiting, examples of the compounds of formula (I) of the invention, whenever appropriate in the form of pharmaceutically acceptable salts, are the following:

1. N-{4-[4-(1,3-benzoxazol-2-yl)pyrazol-3-yl]phenyl}-N'-methyl urea;
2. N-{4-[4-(1,3-benzoxazol-2-yl)pyrazol-3-yl]phenyl}-N'-ethyl urea;
3. N-{4-[4-(1,3-benzoxazol-2-yl)pyrazol-3-yl]phenyl}-N'-isopropyl urea;
4. N-{4-[4-(1,3-benzoxazol-2-yl)pyrazol-3-yl]phenyl}-N'-phenyl urea;
5. N-{4-[4-(1,3-benzoxazol-2-yl)pyrazol-3-yl]phenyl}-N'-3-chlorophenyl urea;
6. N-{4-[4-(1,3-benzoxazol-2-yl)pyrazol-3-yl]phenyl}-N'-4-fluorophenyl urea;
7. N-{4-[4-(1,3-benzoxazol-2-yl)pyrazol-3-yl]phenyl}-N'-2,4-fluorophenyl urea;
8. N-{4-[4-(1,3-benzoxazol-2-yl)pyrazol-3-yl]phenyl}-N'-benzyl urea;
9. N-{4-[4-(1,3-benzoxazol-2-yl)pyrazol-3-yl]phenyl}-N'-4-methoxyphenyl urea;
10. N-{4-[4-(1,3-benzoxazol-2-yl)pyrazol-3-yl]phenyl}-N'-2,6-dimethylphenyl urea;
11. N-{4-[4-(1,3-benzoxazol-2-yl)pyrazol-3-yl]phenyl}-N'-3-methoxyphenyl urea;
12. N-{4-[4-(1,3-benzoxazol-2-yl)pyrazol-3-yl]phenyl}benzenesulphonamide;
13. N-{4-[4-(1,3-benzoxazol-2-yl)pyrazol-3-yl]phenyl}methanesulphonamide;
14. N-{4-[4-(1,3-benzoxazol-2-yl)pyrazol-3-yl]phenyl}toluensulphonamide;
15. N-{4-[4-(1,3-benzoxazol-2-yl)pyrazol-3-yl]phenyl}ethanesulphonamide;
16. N-{4-[4-(1,3-benzoxazol-2-yl)pyrazol-3-yl]phenyl}acetamide;
17. N-{4-[4-(1,3-benzoxazol-2-yl)pyrazol-3-yl]phenyl}benzamide;
18. N-{4-[4-(1,3-benzoxazol-2-yl)pyrazol-3-yl]phenyl}chromone-3-carboxamide;
19. N-{4-[4-(1,3-benzoxazol-2-yl)pyrazol-3-yl]phenyl}cis-2-(2-thiophenecarbonyl)-1-cyclohexanecarboxamide;
20. N-{4-[4-(1,3-benzoxazol-2-yl)pyrazol-3-yl]phenyl}cyclobutanecarboxamide;
21. N-{4-[4-(1,3-benzoxazol-2-yl)pyrazol-3-yl]phenyl}cyclopentanecarboxamide;
22. N-{4-[4-(1,3-benzoxazol-2-yl)pyrazol-3-yl]phenyl}dicyclohexylacetamide;
23. N-{4-[4-(1,3-benzoxazol-2-yl)pyrazol-3-yl]phenyl}diphenylacetamide;
24. N-{4-[4-(1,3-benzoxazol-2-yl)pyrazol-3-yl]phenyl}isoxazole-5-carboxamide;
25. N-{4-[4-(1,3-benzoxazol-2-yl)pyrazol-3-yl]phenyl}menthyloxyacetamide;
26. N-{4-[4-(1,3-benzoxazol-2-yl)pyrazol-3-yl]phenyl}nicotinamide;
27. N-{4-[4-(1,3-benzoxazol-2-yl)pyrazol-3-yl]phenyl}phenylacetamide;
28. N-{4-[4-(1,3-benzoxazol-2-yl)pyrazol-3-yl]phenyl}picolinamide;
29. N-{4-[4-(1,3-benzoxazol-2-yl)pyrazol-3-yl]phenyl}p-tolylacetamide;
30. N-{4-[4-(1,3-benzoxazol-2-yl)pyrazol-3-yl]phenyl}succinamide;
31. N-{4-[4-(1,3-benzoxazol-2-yl)pyrazol-3-yl]phenyl}tert-butylacetamide;
32. N-{4-[4-(1,3-benzoxazol-2-yl)pyrazol-3-yl]phenyl}thiophene-3-acetamide;
33. N-{4-[4-(1,3-benzoxazol-2-yl)pyrazol-3-yl]phenyl}thiophene-3-carboxamide;
34. N-{3-[4-(6-methyl-1,3-benzoxazol-2-yl)pyrazol-3-yl]phenyl}-N'-methyl urea;
35. N-{3-[4-(6-methyl-1,3-benzoxazol-2-yl)pyrazol-3-yl]phenyl}-N'-ethyl urea;
36. N-{3-[4-(6-methyl-1,3-benzoxazol-2-yl)pyrazol-3-yl]phenyl}-N'-isopropyl urea;
37. N-{3-[4-(6-methyl-1,3-benzoxazol-2-yl)pyrazol-3-yl]phenyl}-N'-phenyl urea;
38. N-{3-[4-(6-methyl-1,3-benzoxazol-2-yl)pyrazol-3-yl]phenyl}-N'-3-chlorophenyl urea;
39. N-{3-[4-(6-methyl-1,3-benzoxazol-2-yl)pyrazol-3-yl]phenyl}-N'-4-fluorophenyl urea;
40. N-{3-[4-(6-methyl-1,3-benzoxazol-2-yl)pyrazol-3-yl]phenyl}-N'-2,4-fluorophenyl urea;
41. N-{3-[4-(6-methyl-1,3-benzoxazol-2-yl)pyrazol-3-yl]phenyl}-N'-benzyl urea;
42. N-{3-[4-(6-methyl-1,3-benzoxazol-2-yl)pyrazol-3-yl]phenyl}-N'-4-methoxyphenyl urea;
43. N-{3-[4-(6-methyl-1,3-benzoxazol-2-yl)pyrazol-3-yl]phenyl}-N'-2,6-dimethylphenyl urea;
44. N-{3-[4-(6-methyl-1,3-benzoxazol-2-yl)pyrazol-3-yl]phenyl}-N'-3-methoxyphenyl urea;
45. N-{3-[4-(6-methyl-1,3-benzoxazol-2-yl)pyrazol-3-yl]phenyl}benzenesulphonamide;
46. N-{3-[4-(6-methyl-1,3-benzoxazol-2-yl)pyrazol-3-yl]phenyl}methanesulphonamide;
47. N-{3-[4-(6-methyl-1,3-benzoxazol-2-yl)pyrazol-3-yl]phenyl}toluensulphonamide;
48. N-{3-[4-(6-methyl-1,3-benzoxazol-2-yl)pyrazol-3-yl]phenyl}ethanesulphonamide;

49. N-{3-[4-(6-methyl-1,3-benzoxazol-2-yl)pyrazol-3-yl]phenyl}acetamide;
50. N-{3-[4-(6-methyl-1,3-benzoxazol-2-yl)pyrazol-3-yl]phenyl}benzamide;
51. N-{3-[4-(6-methyl-1,3-benzoxazol-2-yl)pyrazol-3-yl]phenyl}chromone-3-carboxamide;
52. N-{3-[4-(6-methyl-1,3-benzoxazol-2-yl)pyrazol-3-yl]phenyl}cis-2-(2-thiophenecarbonyl)-1-cyclohexanecarboxamide;
53. N-{3-[4-(6-methyl-1,3-benzoxazol-2-yl)pyrazol-3-yl]phenyl}cyclobutanecarboxamide;
54. N-{3-[4-(6-methyl-1,3-benzoxazol-2-yl)pyrazol-3-yl]phenyl}cyclopentanecarboxamide;
55. N-{3-[4-(6-methyl-1,3-benzoxazol-2-yl)pyrazol-3-yl]phenyl}dicyclohexylacetamide;
56. N-{3-[4-(6-methyl-1,3-benzoxazol-2-yl)pyrazol-3-yl]phenyl}diphenylacetamide;
57. N-{3-[4-(6-methyl-1,3-benzoxazol-2-yl)pyrazol-3-yl]phenyl}isoxazole-5-carboxamide;
58. N-{3-[4-(6-methyl-1,3-benzoxazol-2-yl)pyrazol-3-yl]phenyl}menthyloxyacetamide;
59. N-{3-[4-(6-methyl-1,3-benzoxazol-2-yl)pyrazol-3-yl]phenyl}nicotinamide;
60. N-{3-[4-(6-methyl-1,3-benzoxazol-2-yl)pyrazol-3-yl]phenyl}phenylacetamide;
61. N-{3-[4-(6-methyl-1,3-benzoxazol-2-yl)pyrazol-3-yl]phenyl}picolinamide;
62. N-{3-[4-(6-methyl-1,3-benzoxazol-2-yl)pyrazol-3-yl]phenyl}(p-tolyl)acetamide;
63. N-{3-[4-(6-methyl-1,3-benzoxazol-2-yl)pyrazol-3-yl]phenyl}succinamide;
64. N-{3-[4-(6-methyl-1,3-benzoxazol-2-yl)pyrazol-3-yl]phenyl}tert-butylacetamide;
65. N-{3-[4-(6-methyl-1,3-benzoxazol-2-yl)pyrazol-3-yl]phenyl}thiophene-3-acetamide;
66. N-{3-[4-(6-methyl-1,3-benzoxazol-2-yl)pyrazol-3-yl]phenyl}thiophene-3-carboxamide;
67. N-{4-[4-(6-methyl-1,3-benzoxazol-2-yl)pyrazol-3-yl]phenyl}9-fluorenecarboxamide;
68. N-{4-[4-(6-methyl-1,3-benzoxazol-2-yl)pyrazol-3-yl]phenyl}(3,5-dimethoxyphenyl)acetamide;
69. N-{4-[4-(6-methyl-1,3-benzoxazol-2-yl)pyrazol-3-yl]phenyl}1-(aminocarbonyl)-1-cyclopropanecarboxamide;
70. N-{4-[4-(6-methyl-1,3-benzoxazol-2-yl)pyrazol-3-yl]phenyl}1-(p-tolyl)-1-cyclopentanecarboxamide;
71. N-{4-[4-(6-methyl-1,3-benzoxazol-2-yl)pyrazol-3-yl]phenyl}1,2,3,4-tetrahydro-2-naphtaleneamide;
72. N-{4-[4-(6-methyl-1,3-benzoxazol-2-yl)pyrazol-3-yl]phenyl}1-cyanocyclopropanecarboxamide;
73. N-{4-[4-(6-methyl-1,3-benzoxazol-2-yl)pyrazol-3-yl]phenyl}1-methylcyclopropane-1-carboxamide;
74. N-{4-[4-(6-methyl-1,3-benzoxazol-2-yl)pyrazol-3-yl]phenyl}1-naphtalene amide;
75. N-{4-[4-(6-methyl-1,3-benzoxazol-2-yl)pyrazol-3-yl]phenyl}1-phenyl-1-cyclopropanecarboxamide;
76. N-{4-[4-(6-methyl-1,3-benzoxazol-2-yl)pyrazol-3-yl]phenyl}2-(2-methoxyethoxy)acetamide;
77. N-{4-[4-(6-methyl-1,3-benzoxazol-2-yl)pyrazol-3-yl]phenyl}2-(4-chlorobenzoyl)benzamide;
78. N-{4-[4-(6-methyl-1,3-benzoxazol-2-yl)pyrazol-3-yl]phenyl}2-(4-nitrophenyl)propionamide;
79. N-{4-[4-(6-methyl-1,3-benzoxazol-2-yl)pyrazol-3-yl]phenyl}2-(4-pyridyl)thiazole-4-carboxamide;
80. N-{4-[4-(6-methyl-1,3-benzoxazol-2-yl)pyrazol-3-yl]phenyl}2-(benzyloxycarbonylamino)A-cyclohexene-1-carboxamide;
81. N-{4-[4-(6-methyl-1,3-benzoxazol-2-yl)pyrazol-3-yl]phenyl}2-(benzyloxycarbonylamino)-cyclohexanecarboxamide;
82. N-{4-[4-(6-methyl-1,3-benzoxazol-2-yl)pyrazol-3-yl]phenyl}2,2,3,3-tetramethylcyclopropanecarboxamide;
83. N-{4-[4-(6-methyl-1,3-benzoxazol-2-yl)pyrazol-3-yl]phenyl}2,2-dimethyl-4-pentenamide;
84. N-{4-[4-(6-methyl-1,3-benzoxazol-2-yl)pyrazol-3-yl]phenyl}2,2-dimethylhexanamide;
85. N-{4-[4-(6-methyl-1,3-benzoxazol-2-yl)pyrazol-3-yl]phenyl}2,3-dichlorophenoxyacetamide;
86. N-{4-[4-(6-methyl-1,3-benzoxazol-2-yl)pyrazol-3-yl]phenyl}2,4,6-trimethoxyphenylacetamide;
87. N-{4-[4-(6-methyl-1,3-benzoxazol-2-yl)pyrazol-3-yl]phenyl}2,4-dichlorophenylacetamide;
88. N-{4-[4-(6-methyl-1,3-benzoxazol-2-yl)pyrazol-3-yl]phenyl}2,5-dibromobenzamide;
89. N-{4-[4-(6-methyl-1,3-benzoxazol-2-yl)pyrazol-3-yl]phenyl}2,5-dimethoxybenzamide;
90. N-{4-[4-(6-methyl-1,3-benzoxazol-2-yl)pyrazol-3-yl]phenyl}2,6-dichloropyridine-4-carboxamide;
91. N-{4-[4-(6-methyl-1,3-benzoxazol-2-yl)pyrazol-3-yl]phenyl}2,6-dimethylbenzamide;
92. N-{4-[4-(6-methyl-1,3-benzoxazol-2-yl)pyrazol-3-yl]phenyl}2-acetamido-5-bromobenzamide;
93. N-{4-[4-(6-methyl-1,3-benzoxazol-2-yl)pyrazol-3-yl]phenyl}2-acetoxypropionamide;
94. N-{4-[4-(6-methyl-1,3-benzoxazol-2-yl)pyrazol-3-yl]phenyl}2-benzyloxyphenylacetamide;
95. N-{4-[4-(6-methyl-1,3-benzoxazol-2-yl)pyrazol-3-yl]phenyl}2-biphenylcarboxamide;
96. N-{4-[4-(6-methyl-1,3-benzoxazol-2-yl)pyrazol-3-yl]phenyl}2-bromo-4-fluorobenzamide;
97. N-{4-[4-(6-methyl-1,3-benzoxazol-2-yl)pyrazol-3-yl]phenyl}2-chloro-4-methylsulfonylbenzamide;
98. N-{4-[4-(6-methyl-1,3-benzoxazol-2-yl)pyrazol-3-yl]phenyl}2-fluoro-6-iodobenzamide;
99. N-{4-[4-(6-methyl-1,3-benzoxazol-2-yl)pyrazol-3-yl]phenyl}2-fluorobenzamide;
100. N-{4-[4-(6-methyl-1,3-benzoxazol-2-yl)pyrazol-3-yl]phenyl}2-ketobutyramide;
101. N-{4-[4-(5-chloro-1,3-benzoxazol-2-yl)pyrazol-3-yl]phenyl}2-methoxypropionamide;
102. N-{4-[4-(5-chloro-1,3-benzoxazol-2-yl)pyrazol-3-yl]phenyl}2-methyl-4,4,4-trifluorobutyramide;
103. N-{4-[4-(5-chloro-1,3-benzoxazol-2-yl)pyrazol-3-yl]phenyl}2-naphtaleneamide;
104. N-{4-[4-(5-chloro-1,3-benzoxazol-2-yl)pyrazol-3-yl]phenyl}3-(2-chloro-6-fluorophenyl)-5-methylisoxazole-4-carboxamide;
105. N-{4-[4-(5-chloro-1,3-benzoxazol-2-yl)pyrazol-3-yl]phenyl}3-(2-methoxyphenyl)propionamide;
106. N-{4-[4-(5-chloro-1,3-benzoxazol-2-yl)pyrazol-3-yl]phenyl}3-(2-thenoyl)-propionamide;
107. N-{4-[4-(5-chloro-1,3-benzoxazol-2-yl)pyrazol-3-yl]phenyl}3-(diethylamino)propionamide;
108. N-{4-[4-(5-chloro-1,3-benzoxazol-2-yl)pyrazol-3-yl]phenyl}3-(methylsulphonyl)benzamide;
109. N-{4-[4-(5-chloro-1,3-benzoxazol-2-yl)pyrazol-3-yl]phenyl}3-(phenylsulphonyl)propionamide;
110. N-{4-[4-(5-chloro-1,3-benzoxazol-2-yl)pyrazol-3-yl]phenyl}3,4,5-trimethoxybenzamide;
111. N-{4-[4-(5-chloro-1,3-benzoxazol-2-yl)pyrazol-3-yl]phenyl}3,4-diethoxybenzamide;
112. N-{4-[4-(5-chloro-1,3-benzoxazol-2-yl)pyrazol-3-yl]phenyl}3,4-dimethoxybenzamide;

113. N-{4-[4-(5-chloro-1,3-benzoxazol-2-yl)pyrazol-3-yl]phenyl}3,5-diacetamidobenzamide;
114. N-{4-[4-(5-chloro-1,3-benzoxazol-2-yl)pyrazol-3-yl]phenyl}3,5-dibromobenzamide;
115. N-{4-[4-(5-chloro-1,3-benzoxazol-2-yl)pyrazol-3-yl]phenyl}3-acetoxybenzamide;
116. N-{4-[4-(5-chloro-1,3-benzoxazol-2-yl)pyrazol-3-yl]phenyl}3-bromobenzamide;
117. N-{4-[4-(5-chloro-1,3-benzoxazol-2-yl)pyrazol-3-yl]phenyl}3-chloro-2-methylbenzamide;
118. N-{4-[4-(5-chloro-1,3-benzoxazol-2-yl)pyrazol-3-yl]phenyl}3-cyanobenzamide;
119. N-{4-[4-(5-chloro-1,3-benzoxazol-2-yl)pyrazol-3-yl]phenyl}3-fluorophenylacetamide;
120. N-{4-[4-(5-chloro-1,3-benzoxazol-2-yl)pyrazol-3-yl]phenyl}3-methoxycyclohexanecarboxamide;
121. N-{4-[4-(5-chloro-1,3-benzoxazol-2-yl)pyrazol-3-yl]phenyl}3-methyl-1-cyclohexanecarboxamide;
122. N-{4-[4-(5-chloro-1,3-benzoxazol-2-yl)pyrazol-3-yl]phenyl}3-methylthiopropionamide;
123. N-{4-[4-(5-chloro-1,3-benzoxazol-2-yl)pyrazol-3-yl]phenyl}3-pyridinepropionamide;
124. N-{4-[4-(5-chloro-1,3-benzoxazol-2-yl)pyrazol-3-yl]phenyl}4-(3,4-dimethoxyphenyl)butyramide;
125. N-{4-[4-(5-chloro-1,3-benzoxazol-2-yl)pyrazol-3-yl]phenyl}4-(dimethylamino)phenylacetamide;
126. N-{4-[4-(5-chloro-1,3-benzoxazol-2-yl)pyrazol-3-yl]phenyl}4-(tert-butoxymethyl)benzamide;
127. N-{4-[4-(5-chloro-1,3-benzoxazol-2-yl)pyrazol-3-yl]phenyl}4,5-dibromothiophene-2-carboxamide;
128. N-{4-[4-(5-chloro-1,3-benzoxazol-2-yl)pyrazol-3-yl]phenyl}4-acetamido-3-nitrobenzamide;
129. N-{4-[4-(5-chloro-1,3-benzoxazol-2-yl)pyrazol-3-yl]phenyl}4-acetamidobutyramide;
130. N-{4-[4-(5-chloro-1,3-benzoxazol-2-yl)pyrazol-3-yl]phenyl}4-biphenylcarboxamide;
131. N-{4-[4-(5-chloro-1,3-benzoxazol-2-yl)pyrazol-3-yl]phenyl}4-bromo-2-fluorobenzamide;
132. N-{4-[4-(5-chloro-1,3-benzoxazol-2-yl)pyrazol-3-yl]phenyl}4-bromo-2-methylbenzamide;
133. N-{4-[4-(5-chloro-1,3-benzoxazol-2-yl)pyrazol-3-yl]phenyl}4-bromo-3-methylbenzamide;
134. N-{4-[4-(5-chloro-1,3-benzoxazol-2-yl)pyrazol-3-yl]phenyl}4-carboxybenzenesulfonamide;
135. N-{4-[4-(5-methyl-1,3-benzoxazol-2-yl)pyrazol-3-yl]phenyl}4-chloro-alpha-methylphenylacetamide;
136. N-{4-[4-(5-methyl-1,3-benzoxazol-2-yl)pyrazol-3-yl]phenyl}4-cyanobenzamide;
137. N-{4-[4-(5-methyl-1,3-benzoxazol-2-yl)pyrazol-3-yl]phenyl}4-diethylaminobenzamide;
138. N-{4-[4-(5-methyl-1,3-benzoxazol-2-yl)pyrazol-3-yl]phenyl}4-dimethylaminobutyramide;
139. N-{4-[4-(5-methyl-1,3-benzoxazol-2-yl)pyrazol-3-yl]phenyl}4-ethoxyphenylacetamide;
140. N-{4-[4-(5-methyl-1,3-benzoxazol-2-yl)pyrazol-3-yl]phenyl}4-iodobenzamide;
141. N-{4-[4-(5-methyl-1,3-benzoxazol-2-yl)pyrazol-3-yl]phenyl}4-iodophenylacetamide;
142. N-{4-[4-(5-methyl-1,3-benzoxazol-2-yl)pyrazol-3-yl]phenyl}4-isopropylphenoxyacetamide;
143. N-{4-[4-(5-methyl-1,3-benzoxazol-2-yl)pyrazol-3-yl]phenyl}4-methyl-3-nitrobenzamide;
144. N-{4-[4-(5-methyl-1,3-benzoxazol-2-yl)pyrazol-3-yl]phenyl}5-(2-thienyl)pentanamide;
145. N-{4-[4-(5-methyl-1,3-benzoxazol-2-yl)pyrazol-3-yl]phenyl}5,6-dichloronicotinamide;
146. N-{4-[4-(5-methyl-1,3-benzoxazol-2-yl)pyrazol-3-yl]phenyl}5-acetamido-2-nitrobenzamide;
147. N-{4-[4-(5-methyl-1,3-benzoxazol-2-yl)pyrazol-3-yl]phenyl}5-benzoylpentanamide;
148. N-{4-[4-(5-methyl-1,3-benzoxazol-2-yl)pyrazol-3-yl]phenyl}5-bromo-3-pyridylacetamide;
149. N-{4-[4-(5-methyl-1,3-benzoxazol-2-yl)pyrazol-3-yl]phenyl}5-chlorothianaphthene-3-acetamide;
150. N-{4-[4-(5-methyl-1,3-benzoxazol-2-yl)pyrazol-3-yl]phenyl}5-methyl-1-phenylpyrazole-4-carboxamide;
151. N-{4-[4-(5-methyl-1,3-benzoxazol-2-yl)pyrazol-3-yl]phenyl}5-methylhexanamide;
152. N-{4-[4-(5-methyl-1,3-benzoxazol-2-yl)pyrazol-3-yl]phenyl}5-methylisoxazole-4-carboxamide;
153. N-{4-[4-(5-methyl-1,3-benzoxazol-2-yl)pyrazol-3-yl]phenyl}6-acetoxy-2-naphtaleneamide;
154. N-{4-[4-(5-methyl-1,3-benzoxazol-2-yl)pyrazol-3-yl]phenyl}6-cyanonicotinamide;
155. N-{4-[4-(5-methyl-1,3-benzoxazol-2-yl)pyrazol-3-yl]phenyl}7-chloro-1-ethyl-6-fluoro-4-oxohydroquinoline-3-carboxamide;
156. N-{4-[4-(5-tertbutyl-1,3-benzoxazol-2-yl)pyrazol-3-yl]phenyl}-N'-methyl urea;
157. N-{4-[4-(5-tertbutyl-1,3-benzoxazol-2-yl)pyrazol-3-yl]phenyl}-N'-ethyl urea;
158. N-{4-[4-(5-tertbutyl-1,3-benzoxazol-2-yl)pyrazol-3-yl]phenyl}-N'-isopropyl urea;
159. N-{4-[4-(5-tertbutyl-1,3-benzoxazol-2-yl)pyrazol-3-yl]phenyl}-N'-phenyl urea;
160. N-{4-[4-(5-tertbutyl-1,3-benzoxazol-2-yl)pyrazol-3-yl]phenyl}-N'-3-chlorophenyl urea;
161. N-{4-[4-(5-tertbutyl-1,3-benzoxazol-2-yl)pyrazol-3-yl]phenyl}-N'-4-fluorophenyl urea;
162. N-{4-[4-(5-tertbutyl-1,3-benzoxazol-2-yl)pyrazol-3-yl]phenyl}-N'-2,4-fluorophenyl urea;
163. N-{4-[4-(5-tertbutyl-1,3-benzoxazol-2-yl)pyrazol-3-yl]phenyl}-N'-benzyl urea;
164. N-{4-[4-(5-tertbutyl-1,3-benzoxazol-2-yl)pyrazol-3-yl]phenyl}-N'-4-methoxyphenyl urea;
165. N-{4-[4-(5-tertbutyl-1,3-benzoxazol-2-yl)pyrazol-3-yl]phenyl}-N'-2,6-dimethylphenyl urea;
166. N-{4-[4-(5-tertbutyl-1,3-benzoxazol-2-yl)pyrazol-3-yl]phenyl}-N'-3-methoxyphenyl urea;
167. N-{4-[4-(5-tertbutyl-1,3-benzoxazol-2-yl)pyrazol-3-yl]phenyl}benzenesulphonamide;
168. N-{4-[4-(5-tertbutyl-1,3-benzoxazol-2-yl)pyrazol-3-yl]phenyl}methanesulphonamide;
169. N-{4-[4-(5-tertbutyl-1,3-benzoxazol-2-yl)pyrazol-3-yl]phenyl}toluensulphonamide;
170. N-{4-[4-(5-tertbutyl-1,3-benzoxazol-2-yl)pyrazol-3-yl]phenyl}ethanesulphonamide;
171. N-{4-[4-(5-tertbutyl-1,3-benzoxazol-2-yl)pyrazol-3-yl]phenyl}acetamide;
172. N-{4-[4-(5-tertbutyl-1,3-benzoxazol-2-yl)pyrazol-3-yl]phenyl}benzamide;
173. N-{4-[4-(5-tertbutyl-1,3-benzoxazol-2-yl)pyrazol-3-yl]phenyl}chromone-3-carboxamide;
174. N-{4-[4-(5-tertbutyl-1,3-benzoxazol-2-yl)pyrazol-3-yl]phenyl}cis-2-(2-thiophenecarbonyl)-1-cyclohexanecarboxamide;
175. N-{4-[4-(5-tertbutyl-1,3-benzoxazol-2-yl)pyrazol-3-yl]phenyl}cyclobutanecarboxamide;
176. N-{4-[4-(5-tertbutyl-1,3-benzoxazol-2-yl)pyrazol-3-yl]phenyl}cyclopentanecarboxamide;
177. N-{4-[4-(5-tertbutyl-1,3-benzoxazol-2-yl)pyrazol-3-yl]phenyl}dicyclohexylacetamide;

178. N-{4-[4-(5-tertbutyl-1,3-benzoxazol-2-yl)pyrazol-3-yl]phenyl}diphenylacetamide;
179. N-{4-[4-(5,7-chloro-6-methyl-1,3-benzoxazol-2-yl)pyrazol-3-yl]phenyl}isoxazole-5-carboxamide;
180. N-{4-[4-(5,7-chloro-6-methyl-1,3-benzoxazol-2-yl)pyrazol-3-yl]phenyl}menthyloxyacetamide;
181. N-{4-[4-(5,7-chloro-6-methyl-1,3-benzoxazol-2-yl)pyrazol-3-yl]phenyl}nicotinamide;
182. N-{4-[4-(5,7-chloro-6-methyl-1,3-benzoxazol-2-yl)pyrazol-3-yl]phenyl}phenylacetamide;
183. N-{4-[4-(5,7-chloro-6-methyl-1,3-benzoxazol-2-yl)pyrazol-3-yl]phenyl}picolinamide;
184. N-{4-[4-(5,7-chloro-6-methyl-1,3-benzoxazol-2-yl)pyrazol-3-yl]phenyl}p-tolylacetamide;
185. N-{4-[4-(5,7-chloro-6-methyl-1,3-benzoxazol-2-yl)pyrazol-3-yl]phenyl}succinamide;
186. N-{4-[4-(5,7-chloro-6-methyl-1,3-benzoxazol-2-yl)pyrazol-3-yl]phenyl}tert-butylacetamide;
187. N-{4-[4-(5,7-chloro-6-methyl-1,3-benzoxazol-2-yl)pyrazol-3-yl]phenyl}thiophene-3-acetamide;
188. N-{4-[4-(5,7-chloro-6-methyl-1,3-benzoxazol-2-yl)pyrazol-3-yl]phenyl}thiophene-3-carboxamide;
189. N-{4-[4-(5-ethylsulfonyl-1,3-benzoxazol-2-yl)pyrazol-3-yl]phenyl}4-chloro-alpha-methylphenylacetamide;
190. N-{4-[4-(5-ethylsulfonyl-1,3-benzoxazol-2-yl)pyrazol-3-yl]phenyl}4-cyanobenzamide;
191. N-{4-[4-(5-ethylsulfonyl-1,3-benzoxazol-2-yl)pyrazol-3-yl]phenyl}4-diethylaminobenzamide;
192. N-{4-[4-(5-ethylsulfonyl-1,3-benzoxazol-2-yl)pyrazol-3-yl]phenyl}4-dimethylaminobutyramide;
193. N-{4-[4-(5-ethylsulfonyl-1,3-benzoxazol-2-yl)pyrazol-3-yl]phenyl}4-ethoxyphenylacetamide;
194. N-{4-[4-(5-ethylsulfonyl-1,3-benzoxazol-2-yl)pyrazol-3-yl]phenyl}4-iodobenzamide;
195. N-{4-[4-(5-ethylsulfonyl-1,3-benzoxazol-2-yl)pyrazol-3-yl]phenyl}4-iodophenylacetamide;
196. N-{4-[4-(5-ethylsulfonyl-1,3-benzoxazol-2-yl)pyrazol-3-yl]phenyl}4-isopropylphenoxyacetamide;
197. N-{4-[4-(5-ethylsulfonyl-1,3-benzoxazol-2-yl)pyrazol-3-yl]phenyl}4-methyl-3-nitrobenzamide;
198. N-{4-[4-(5-ethylsulfonyl-1,3-benzoxazol-2-yl)pyrazol-3-yl]phenyl}5-(2-thienyl)pentanamide;
199. N-{4-[4-(5-phenyl-1,3-benzoxazol-2-yl)pyrazol-3-yl]phenyl}5,6-dichloronicotinamide;
200. N-{4-[4-(5-phenyl-1,3-benzoxazol-2-yl)pyrazol-3-yl]phenyl}5-acetamido-2-nitrobenzamide;
201. N-{4-[4-(5-phenyl-1,3-benzoxazol-2-yl)pyrazol-3-yl]phenyl}5-benzoylpentanamide;
202. N-{4-[4-(5-phenyl-1,3-benzoxazol-2-yl)pyrazol-3-yl]phenyl}5-bromo-3-pyridylacetamide;
203. N-{4-[4-(5-phenyl-1,3-benzoxazol-2-yl)pyrazol-3-yl]phenyl}5-chlorothianaphthene-3-acetamide;
204. N-{4-[4-(4-methyl-1,3-benzoxazol-2-yl)pyrazol-3-yl]phenyl}5-methyl-1-phenylpyrazole-4-carboxamide;
205. N-{4-[4-(4-methyl-1,3-benzoxazol-2-yl)pyrazol-3-yl]phenyl}5-methylhexanamide;
206. N-{4-[4-(4-methyl-1,3-benzoxazol-2-yl)pyrazol-3-yl]phenyl}5-methylisoxazole-4-carboxamide;
207. N-{4-[4-(4-methyl-1,3-benzoxazol-2-yl)pyrazol-3-yl]phenyl}6-acetoxy-2-naphtaleneamide;
208. N-{4-[4-(4-methyl-1,3-benzoxazol-2-yl)pyrazol-3-yl]phenyl}6-cyanonicotinamide;
209. N-{4-[4-(4-methyl-1,3-benzoxazol-2-yl)pyrazol-3-yl]phenyl}7-chloro-1-ethyl-6-fluoro4-oxohydroquinoline-3-carboxamide;
210. N-{4-[4-(4-methyl-1,3-benzoxazol-2-yl)pyrazol-3-yl]phenyl}9-fluorenecarboxamide;
211. N-{4-[4-(4-methyl-1,3-benzoxazol-2-yl)pyrazol-3-yl]phenyl}(3,5-dimethoxyphenyl)acetamide;
212. N-{4-[4-(4-methyl-1,3-benzoxazol-2-yl)pyrazol-3-yl]phenyl}1-(aminocarbonyl)-1-cyclopropanecarboxamide;
213. N-{4-[4-(4-methyl-1,3-benzoxazol-2-yl)pyrazol-3-yl]phenyl}-(p-tolyl)-1-cyclopentanecarboxamide;
214. N-{4-[4-(4-methyl-1,3-benzoxazol-2-yl)pyrazol-3-yl]phenyl}1,2,3,4-tetrahydro-2-naphtaleneamide;
215. N-{4-[4-(4-methyl-1,3-benzoxazol-2-yl)pyrazol-3-yl]phenyl}1-cyanocyclopropanecarboxamide;
216. N-{4-[4-(4-methyl-1,3-benzoxazol-2-yl)pyrazol-3-yl]phenyl}1-methylcyclopropane-1-carboxamide;
217. N-{4-[4-(4-methyl-1,3-benzoxazol-2-yl)pyrazol-3-yl]phenyl}1-naphtalene amide;
218. N-{4-[4-(4-methyl-1,3-benzoxazol-2-yl)pyrazol-3-yl]phenyl}1-phenyl-1-cyclopropanecarboxamide;
219. N-{4-[4-(4-methyl-1,3-benzoxazol-2-yl)pyrazol-3-yl]phenyl}2-(2-methoxyethoxy)acetamide;
220. N-{4-[4-(4-methyl-1,3-benzoxazol-2-yl)pyrazol-3-yl]phenyl}2-(4-chlorobenzoyl)benzamide;
221. N-{4-[4-(4-methyl-1,3-benzoxazol-2-yl)pyrazol-3-yl]phenyl}2-(4-nitrophenyl)propionamide;
222. N-{4-[4-(4-methyl-1,3-benzoxazol-2-yl)pyrazol-3-yl]phenyl}2-(4-pyridyl)thiazole-4-carboxamide;
223. N-{4-[4-(4-methyl-1,3-benzoxazol-2-yl)pyrazol-3-yl]phenyl}2-(benzyloxycarbonylamino)-4-cyclohexene-1-carboxamide;
224. N-{4-[4-(4-methyl-7-isopropyl-1,3-benzoxazol-2-yl)pyrazol-3-yl]phenyl}2-(benzyloxycarbonylamino)-cyclohexanecarboxamide;
225. N-{4-[4-(4-methyl-7-isopropyl-1,3-benzoxazol-2-yl)pyrazol-3-yl]phenyl}2,2,3,3-tetramethylcyclopropanecarboxamide;
226. N-{4-[4-(4-methyl-7-isopropyl-1,3-benzoxazol-2-yl)pyrazol-3-yl]phenyl}2,2-dimethyl-4-pentenamide;
227. N-{4-[4-(4-methyl-7-isopropyl-1,3-benzoxazol-2-yl)pyrazol-3-yl]phenyl}2,2-dimethylhexanamide;
228. N-{4-[4-(4-methyl-7-isopropyl-1,3-benzoxazol-2-yl)pyrazol-3-yl]phenyl}2,3-dichlorophenoxyacetamide;
229. N-{4-[4-(4-methyl-7-isopropyl-1,3-benzoxazol-2-yl)pyrazol-3-yl]phenyl}2,4,6-trimethoxyphenylacetamide;
230. N-{4-[4-(4-methyl-7-isopropyl-1,3-benzoxazol-2-yl)pyrazol-3-yl]phenyl}2,4-dichlorophenylacetamide;
231. N-{4-[4-(4-methyl-7-isopropyl-1,3-benzoxazol-2-yl)pyrazol-3-yl]phenyl}2,5-dibromobenzamide;
232. N-{4-[4-(4-methyl-7-isopropyl-1,3-benzoxazol-2-yl)pyrazol-3-yl]phenyl}2,5-dimethoxybenzamide;
233. N-[4-[4-(1,3-naphth[2,3-d]oxazol-2-yl)pyrazol-3-yl]phenyl]2,6-dichloropyridine-4-carboxamide;
234. N-[4-[4-(1,3-naphth[2,3-d]oxazol-2-yl)pyrazol-3-yl]phenyl]2,6-dimethylbenzamide;
235. N-[4-[4-(1,3-naphth[2,3-d]oxazol-2-yl)pyrazol-3-yl]phenyl]2-acetamido-5-bromobenzamide;
236. N-[4-[4-(1,3-naphth[2,3-d]oxazol-2-yl)pyrazol-3-yl]phenyl]2-acetoxypropionamide;
237. N-[4-[4-(1,3-naphth[2,3-d]oxazol-2-yl)pyrazol-3-yl]phenyl]2-benzyloxyphenylacetamide;
238. N-[4-[4-(1,3-naphth[2,3-d]oxazol-2-yl)pyrazol-3-yl]phenyl]2-biphenylcarboxamide;
239. N-[4-[4-(1,3-naphth[2,3-d]oxazol-2-yl)pyrazol-3-yl]phenyl]2-bromo-4-fluorobenzamide;
240. N-[4-[4-(1,3-naphth[2,3-d]oxazol-2-yl)pyrazol-3-yl]phenyl]2-chloro-4-methylsulfonylbenzamide;
241. N-[4-[4-(1,3-naphth[2,3-d]oxazol-2-yl)pyrazol-3-yl]phenyl]2-fluoro-6-iodobenzamide;
242. N-[4-[4-(1,3-naphth[2,3-d]oxazol-2-yl)pyrazol-3-yl]phenyl]2-fluorobenzamide;

243. N-[4-[4-(1,3-oxazole[4,5-b]pyridine2-yl)pyrazol-3-yl]phenyl]2-methoxypropionamide;
244. N-[4-[4-(1,3-oxazole[4,5-b]pyridine2-yl)pyrazol-3-yl]phenyl]2-methyl-4,4,4-trifluorobutyramide;
245. N-[4-[4-(1,3-oxazole[4,5-b]pyridine2-yl)pyrazol-3-yl]phenyl]2-naphtaleneamide;
246. N-[4-[4-(1,3-oxazole[4,5-b]pyridine2-yl)pyrazol-3-yl]phenyl]3-(2-chloro-6-fluorophenyl)-5-methylisoxazole-4-carboxamide;
247. N-[4-[4-(1,3-oxazole[4,5-b]pyridine2-yl)pyrazol-3-yl]phenyl]3-(2-methoxyphenyl)propionamide;
248. N-[4-[4-(1,3-oxazole[4,5-b]pyridine2-yl)pyrazol-3-yl]phenyl]3-(2-thenoyl)-propionamide;
249. N-[4-[4-(1,3-oxazole[4,5-b]pyridine2-yl)pyrazol-3-yl]phenyl]3-(diethylamino)propionamide;
250. N-[4-[4-(1,3-oxazole[4,5-b]pyridine2-yl)pyrazol-3-yl]phenyl]3-(methylsulphonyl)benzamide;
251. N-[4-[4-(1,3-oxazole[4,5-b]pyridine2-yl)pyrazol-3-yl]phenyl]3-(phenylsulphonyl)propionamide;
252. N-[4-[4-(1,3-naphth[2,3-d]oxazol-2-yl)pyrazol-3-yl]phenyl]3,4,5-trimethoxybenzamide;
253. N-[4-[4-(1,3-naphth[2,3-d]oxazol-2-yl)pyrazol-3-yl]phenyl]3,4-diethoxybenzamide;
254. N-[4-[4-(1,3-naphth[2,3-d]oxazol-2-yl)pyrazol-3-yl]phenyl]3,4-dimethoxybenzamide;
255. N-[4-[4-(1,3-naphth[2,3-d]oxazol-2-yl)pyrazol-3-yl]phenyl]3,5-diacetamidobenzamide;
256. N-[4-[4-(1,3-naphth[2,3-d]oxazol-2-yl)pyrazol-3-yl]phenyl]3,5-dibromobenzamide;
257. N-[4-[4-(1,3-naphth[2,3-d]oxazol-2-yl)pyrazol-3-yl]phenyl]3-acetoxybenzamide;
258. N-[4-[4-(1,3-naphth[2,3-d]oxazol-2-yl)pyrazol-3-yl]phenyl]3-bromobenzamide;
259. N-[4-[4-(1,3-naphth[2,3-d]oxazol-2-yl)pyrazol-3-yl]phenyl]3-chloro-2-methylbenzamide;
260. N-[4-[4-(1,3-naphth[2,3-d]oxazol-2-yl)pyrazol-3-yl]phenyl]3-cyanobenzamide;
261. N-{3-[4-(1,3-benzoxazol-2-yl)pyrazol-3-yl]phenyl}3-fluorophenylacetamide;
262. N-{3-[4-(1,3-benzoxazol-2-yl)pyrazol-3-yl]phenyl}3-methoxycyclohexanecarboxamide;
263. N-{3-[4-(1,3-benzoxazol-2-yl)pyrazol-3-yl]phenyl}3-methyl-1-cyclohexanecarboxamide;
264. N-{3-[4-(1,3-benzoxazol-2-yl)pyrazol-3-yl]phenyl}3-methylthiopropionamide;
265. N-{3-[4-(1,3-benzoxazol-2-yl)pyrazol-3-yl]phenyl}3-pyridinepropionamide;
266. N-{3-[4-(1,3-benzoxazol-2-yl)pyrazol-3-yl]phenyl}4-(3,4-dimethoxyphenyl)butyramide;
267. N-{3-[4-(1,3-benzoxazol-2-yl)pyrazol-3-yl]phenyl}4-(dimethylamino)phenylacetamide;
268. N-{3-[4-(1,3-benzoxazol-2-yl)pyrazol-3-yl]phenyl}4-(tert-butoxymethyl)benzamide;
269. N-{3-[4-(1,3-benzoxazol-2-yl)pyrazol-3-yl]phenyl}4,5-dibromothiophene-2-carboxamide;
270. N-{3-[4-(5-chloro-1,3-benzoxazol-2-yl)pyrazol-3-yl]phenyl}4-acetamido-3-nitrobenzamide;
271. N-{3-[4-(5-chloro-1,3-benzoxazol-2-yl)pyrazol-3-yl]phenyl}4-acetamidobutyramide;
272. N-{3-[4-(5-chloro-1,3-benzoxazol-2-yl)pyrazol-3-yl]phenyl}4-biphenylcarboxamide;
273. N-{3-[4-(5-chloro-1,3-benzoxazol-2-yl)pyrazol-3-yl]phenyl}4-bromo-2-fluorobenzamide;
274. N-{3-[4-(5-chloro-1,3-benzoxazol-2-yl)pyrazol-3-yl]phenyl}4-bromo-2-methylbenzamide;
275. N-{3-[4-(5-chloro-1,3-benzoxazol-2-yl)pyrazol-3-yl]phenyl}4-bromo-3-methylbenzamide;
276. N-{3-[4-(5-chloro-1,3-benzoxazol-2-yl)pyrazol-3-yl]phenyl}4-carboxybenzenesulfonamide;
277. N-{3-[4-(5-chloro-1,3-benzoxazol-2-yl)pyrazol-3-yl]phenyl}-N'-methyl urea;
278. N-{3-[4-(5-chloro-1,3-benzoxazol-2-yl)pyrazol-3-yl]phenyl}-N'-ethyl urea;
279. N-{3-[4-(5-chloro-1,3-benzoxazol-2-yl)pyrazol-3-yl]phenyl}-N'-isopropyl urea;
280. N-{3-[4-(5-chloro-1,3-benzoxazol-2-yl)pyrazol-3-yl]phenyl}-N'-phenyl urea;
281. N-{3-[4-(5-chloro-1,3-benzoxazol-2-yl)pyrazol-3-yl]phenyl}-N'-3-chlorophenyl urea;
282. N-{3-[4-(5-chloro-1,3-benzoxazol-2-yl)pyrazol-3-yl]phenyl}-N'-4-fluorophenyl urea;
283. N-{3-[4-(5-chloro-1,3-benzoxazol-2-yl)pyrazol-3-yl]phenyl}-N'-2,4-fluorophenyl urea;
284. N-{3-[4-(5-chloro-1,3-benzoxazol-2-yl)pyrazol-3-yl]phenyl}-N'-benzyl urea;
285. N-{3-[4-(5-methyl-1,3-benzoxazol-2-yl)pyrazol-3-yl]phenyl}-N'-4-methoxyphenyl urea;
286. N-{3-[4-(5-methyl-1,3-benzoxazol-2-yl)pyrazol-3-yl]phenyl}-N'-2,6-dimethylphenyl urea;
287. N-{3-[4-(5-methyl-1,3-benzoxazol-2-yl)pyrazol-3-yl]phenyl}-N'-3-methoxyphenyl urea;
288. N-{3-[4-(5-methyl-1,3-benzoxazol-2-yl)pyrazol-3-yl]phenyl}benzenesulphonamide;
289. N-{3-[4-(5-methyl-1,3-benzoxazol-2-yl)pyrazol-3-yl]phenyl}methanesulphonamide;
290. N-{3-[4-(5-methyl-1,3-benzoxazol-2-yl)pyrazol-3-yl]phenyl}toluensulphonamide;
291. N-{3-[4-(5-methyl-1,3-benzoxazol-2-yl)pyrazol-3-yl]phenyl}ethanesulphonamide;
292. N-{3-[4-(5-methyl-1,3-benzoxazol-2-yl)pyrazol-3-yl]phenyl}acetamide;
293. N-{3-[4-(5-methyl-1,3-benzoxazol-2-yl)pyrazol-3-yl]phenyl}benzamide;
294. N-{3-[4-(5-methyl-1,3-benzoxazol-2-yl)pyrazol-3-yl]phenyl}chromone-3-carboxamide;
295. N-{3-[4-(5-methyl-1,3-benzoxazol-2-yl)pyrazol-3-yl]phenyl}cis-2-(2-thiophenecarbonyl)-1-cyclohexanecarboxamide;
296. N-{3-[4-(5-methyl-1,3-benzoxazol-2-yl)pyrazol-3-yl]phenyl}cyclobutanecarboxamide;
297. N-{3-[4-(5-methyl-1,3-benzoxazol-2-yl)pyrazol-3-yl]phenyl}cyclopentanecarboxamide;
298. N-{3-[4-(5-methyl-1,3-benzoxazol-2-yl)pyrazol-3-yl]phenyl}dicyclohexylacetamide;
299. N-{3-[4-(5-methyl-1,3-benzoxazol-2-yl)pyrazol-3-yl]phenyl}diphenylacetamide;
300. N-{3-[4-(5-tertbutyl-1,3-benzoxazol-2-yl)pyrazol-3-yl]phenyl}isoxazole-5-carboxamide;
301. N-{3-[4-(5-tertbutyl-1,3-benzoxazol-2-yl)pyrazol-3-yl]phenyl}menthyloxyacetamide;
302. N-{3-[4-(5-tertbutyl-1,3-benzoxazol-2-yl)pyrazol-3-yl]phenyl}nicotinamide;
303. N-{3-[4-(5-tertbutyl-1,3-benzoxazol-2-yl)pyrazol-3-yl]phenyl}phenylacetamide;
304. N-{3-[4-(5-tertbutyl-1,3-benzoxazol-2-yl)pyrazol-3-yl]phenyl}picolinamide;
305. N-{3-[4-(5-tertbutyl-1,3-benzoxazol-2-yl)pyrazol-3-yl]phenyl}p-tolylacetamide;
306. N-{3-[4-(5-tertbutyl-1,3-benzoxazol-2-yl)pyrazol-3-yl]phenyl}succinamide;
307. N-{3-[4-(5-tertbutyl-1,3-benzoxazol-2-yl)pyrazol-3-yl]phenyl}tert-butylacetamide;
308. N-{3-[4-(5-tertbutyl-1,3-benzoxazol-2-yl)pyrazol-3-yl]phenyl}thiophene-3-acetamide;

309. N-{3-[4-(5-tertbutyl-1,3-benzoxazol-2-yl)pyrazol-3-yl]phenyl}thiophene-3-carboxamide;
310. N-{3-[4-(5-tertbutyl-1,3-benzoxazol-2-yl)pyrazol-3-yl]phenyl}4-chloro-alpha-methylphenylacetamide;
311. N-{3-[4-(5-tertbutyl-1,3-benzoxazol-2-yl)pyrazol-3-yl]phenyl}4-cyanobenzamide;
312. N-{3-[4-(5-tertbutyl-1,3-benzoxazol-2-yl)pyrazol-3-yl]phenyl}4-diethylaminobenzamide;
313. N-{3-[4-(5-tertbutyl-1,3-benzoxazol-2-yl)pyrazol-3-yl]phenyl}4-dimethylaminobutyramide;
314. N-{3-[4-(5,7-chloro-6-methyl-1,3-benzoxazol-2-yl)pyrazol-3-yl]phenyl}4-ethoxyphenylacetamide;
315. N-{3-[4-(5,7-chloro-6-methyl-1,3-benzoxazol-2-yl)pyrazol-3-yl]phenyl}4-iodobenzamide;
316. N-{3-[4-(5,7-chloro-6-methyl-1,3-benzoxazol-2-yl)pyrazol-3-yl]phenyl}4-iodophenylacetamide;
317. N-{3-[4-(5,7-chloro-6-methyl-1,3-benzoxazol-2-yl)pyrazol-3-yl]phenyl}4-isopropylphenoxyacetamide;
318. N-{3-[4-(5,7-chloro-6-methyl-1,3-benzoxazol-2-yl)pyrazol-3-yl]phenyl}4-methyl-3-nitrobenzamide;
319. N-{3-[4-(5,7-chloro-6-methyl-1,3-benzoxazol-2-yl)pyrazol-3-yl]phenyl)5-(2-thienyl)pentanamide;
320. N-{3-[4-(5,7-chloro-6-methyl-1,3-benzoxazol-2-yl)pyrazol-3-yl]phenyl}5,6-dichloronicotinamide;
321. N-{3-[4-(5,7-chloro-6-methyl-1,3-benzoxazol-2-yl)pyrazol-3-yl]phenyl}5-acetamido-2-nitrobenzamide;
322. N-{3-[4-(5,7-chloro-6-methyl-1,3-benzoxazol-2-yl)pyrazol-3-yl]phenyl}5-benzoylpentanamide;
323. N-{3-[4-(5,7-chloro-6-methyl-1,3-benzoxazol-2-yl)pyrazol-3-yl]phenyl}5-bromo-3-pyridylacetamide;
324. N-{3-[4-(5-ethylsulfonyl-1,3-benzoxazol-2-yl)pyrazol-3-yl]phenyl}5-chlorothianaphthene-3-acetamide;
325. N-{3-[4-(5-ethylsulfonyl-1,3-benzoxazol-2-yl)pyrazol-3-yl]phenyl}5-methyl-1-phenylpyrazole-4-carboxamide;
326. N-{3-[4-(5-ethylsulfonyl-1,3-benzoxazol-2-yl)pyrazol-3-yl]phenyl}5-methylhexanamide;
327. N-{3-[4-(5-ethylsulfonyl-1,3-benzoxazol-2-yl)pyrazol-3-yl]phenyl}5-methylisoxazole-4-carboxamide;
328. N-{3-[4-(5-ethylsulfonyl-1,3-benzoxazol-2-yl)pyrazol-3-yl]phenyl}6-acetoxy-2-naphtaleneamide;
329. N-{3-[4-(5-ethylsulfonyl-1,3-benzoxazol-2-yl)pyrazol-3-yl]phenyl}6-cyanonicotinamide;
330. N-{3-[4-(5-ethylsulfonyl-1,3-benzoxazol-2-yl)pyrazol-3-yl]phenyl}7-chloro-1-ethyl-6-fluoro-4-oxohydroquinoline-3-carboxamide;
331. N-{3-[4-(5-ethylsulfonyl-1,3-benzoxazol-2-yl)pyrazol-3-yl]phenyl}-N'-methyl urea;
332. N-{3-[4-(5-ethylsulfonyl-1,3-benzoxazol-2-yl)pyrazol-3-yl]phenyl}-N'-ethyl urea;
333. N-{3-[4-(5-ethylsulfonyl-1,3-benzoxazol-2-yl)pyrazol-3-yl]phenyl}-N'-isopropyl urea;
334. N-{3-[4-(5-phenyl-1,3-benzoxazol-2-yl)pyrazol-3-yl]phenyl}-N'-phenyl urea;
335. N-{3-[4-(5-phenyl-1,3-benzoxazol-2-yl)pyrazol-3-yl]phenyl}-N'-3-chlorophenyl urea;
336. N-{3-[4-(5-phenyl-1,3-benzoxazol-2-yl)pyrazol-3-yl]phenyl}-N'-4-fluorophenyl urea;
337. N-{3-[4-(5-phenyl-1,3-benzoxazol-2-yl)pyrazol-3-yl]phenyl}-N'-2,4-fluorophenyl urea;
338. N-(3-[4-(5-phenyl-1,3-benzoxazol-2-yl)pyrazol-3-yl]phenyl}-N'-benzyl urea;
339. N-{3-[4-(5-phenyl-1,3-benzoxazol-2-yl)pyrazol-3-yl]phenyl}-N'-4-methoxyphenyl urea;
340. N-{3-[4-(5-phenyl-1,3-benzoxazol-2-yl)pyrazol-3-yl]phenyl}-N'-2,6-dimethylphenyl urea;
341. N-{3-[4-(5-phenyl-1,3-benzoxazol-2-yl)pyrazol-3-yl]phenyl}-N'-3-methoxyphenyl urea;
342. N-{3-[4-(5-phenyl-1,3-benzoxazol-2-yl)pyrazol-3-yl]phenyl}benzenesulphonamide;
343. N-{3-[4-(5-phenyl-1,3-benzoxazol-2-yl)pyrazol-3-yl]phenyl}methanesulphonamide;
344. N-{3-[4-(4-methyl-7-isopropyl-1,3-benzoxazol-2-yl)pyrazol-3-yl]phenyl}toluensulphonamide;
345. N-{3-[4-(4-methyl-7-isopropyl-1,3-benzoxazol-2-yl)pyrazol-3-yl]phenyl}ethanesulphonamide;
346. N-{3-[4-(4-methyl-7-isopropyl-1,3-benzoxazol-2-yl)pyrazol-3-yl]phenyl}acetamide;
347. N-{3-[4-(4-methyl-7-isopropyl-1,3-benzoxazol-2-yl)pyrazol-3-yl]phenyl}benzamide;
348. N-{3-[4-(4-methyl-7-isopropyl-1,3-benzoxazol-2-yl)pyrazol-3-yl]phenyl}chromone-3-carboxamide;
349. N-{3-[4-(4-methyl-7-isopropyl-1,3-benzoxazol-2-yl)pyrazol-3-yl]phenyl}cis-2-(2-thiophenecarbonyl)-1-cyclohexanecarboxamide;
350. N-{3-[4-(4-methyl-7-isopropyl-1,3-benzoxazol-2-yl)pyrazol-3-yl]phenyl}cyclobutanecarboxamide;
351. N-{3-[4-(4-methyl-7-isopropyl-1,3-benzoxazol-2-yl)pyrazol-3-yl]phenyl}cyclopentanecarboxamide;
352. N-{3-[4-(4-methyl-7-isopropyl-1,3-benzoxazol-2-yl)pyrazol-3-yl]phenyl}dicyclohexylacetamide;
353. N-{3-[4-(4-methyl-7-isopropyl-1,3-benzoxazol-2-yl)pyrazol-3-yl]phenyl}diphenylacetamide;
354. N-[3-[4-(1,3-naphth[2,3-d]oxazol-2-yl)pyrazol-3-yl]phenyl]isoxazole-5-carboxamide;
355. N-[3-[4-(1,3-naphth[2,3-d]oxazol-2-yl)pyrazol-3-yl]phenyl]menthyloxyacetamide;
356. N-[3-[4-(1,3-naphth[2,3-d]oxazol-2-yl)pyrazol-3-yl]phenyl]nicotinamide;
357. N-[3-[4-(1,3-naphth[2,3-d]oxazol-2-yl)pyrazol-3-yl]phenyl]phenylacetamide;
358. N-[3-[4-(1,3-naphth[2,3-d]oxazol-2-yl)pyrazol-3-yl]phenyl]picolinamide;
359. N-[3-[4-(1,3-naphth[2,3-d]oxazol-2-yl)pyrazol-3-yl]phenyl]p-tolylacetamide;
360. N-[3-[4-(1,3-naphth[2,3-d]oxazol-2-yl)pyrazol-3-yl]phenyl]succinamide;
361. N-[3-[4-(1,3-naphth[2,3-d]oxazol-2-yl)pyrazol-3-yl]phenyl]tert-butylacetamide;
362. N-[3-[4-(1,3-naphth[2,3-d]oxazol-2-yl)pyrazol-3-yl]phenyl]thiophene-3-acetamide;
363. N-[3-[4-(1,3-oxazole[4,5-b]pyridine2-yl)pyrazol-3-yl]phenyl]thiophene-3-carboxamide;
364. N-[3-[4-(1,3-oxazole[4,5-b]pyridine2-yl)pyrazol-3-yl]phenyl]2-(2-methoxyethoxy)acetamide;
365. N-[3-[4-(1,3-oxazole[4,5-b]pyridine2-yl)pyrazol-3-yl]phenyl]2-(4-chlorobenzoyl)benzamide;
366. N-[3-[4-(1,3-oxazole[4,5-b]pyridine2-yl)pyrazol-3-yl]phenyl]2-(4-nitrophenyl)propionamide;
367. N-[3-[4-(1,3-oxazole[4,5-b]pyridine2-yl)pyrazol-3-yl]phenyl]2-(4-pyridyl)thiazole-4-carboxamide;
368. N-[3-[4-(1,3-oxazole[4,5-b]pyridine2-yl)pyrazol-3-yl]phenyl]2-(benzyloxycarbonylamino)-4-cyclohexene-1-carboxamide;
369. N-[3-[4-(1,3-oxazole[4,5-b]pyridine2-yl)pyrazol-3-yl]phenyl]2-(benzyloxycarbonylamino)-cyclohexanecarboxamide;
370. N-[3-[4-(1,3-oxazole[4,5-b]pyridine2-yl)pyrazol-3-yl]phenyl]2,2,3,3-tetramethylcyclopropanecarboxamide;
371. N-[3-[4-(1,3-oxazole[4,5-b]pyridine2-yl)pyrazol-3-yl]phenyl]2,2-dimethyl-4-pentenamide;
372. N-[3-[4-(1,3-oxazole[4,5-b]pyridine2-yl)pyrazol-3-yl]phenyl]2,2-dimethylhexanamide;
373. N-[3-[4-(1,3-naphth[2,3-d]oxazol-2-yl)pyrazol-3-yl]phenyl]2,3-dichlorophenoxyacetamide;

374. N-[3-[4-(1,3-naphth[2,3-d]oxazol-2-yl)pyrazol-3-yl]phenyl]2,4,6-trimethoxyphenylacetamide;
375. N-[3-[4-(1,3-naphth[2,3-d]oxazol-2-yl)pyrazol-3-yl]phenyl]2,4-dichlorophenylacetamide;
376. N-[3-[4-(1,3-naphth[2,3-d]oxazol-2-yl)pyrazol-3-yl]phenyl]2,5-dibromobenzamide;
377. N-[3-[4-(1,3-naphth[2,3-d]oxazol-2-yl)pyrazol-3-yl]phenyl]2,5-dimethoxybenzamide;
378. N-[3-[4-(1,3-naphth[2,3-d]oxazol-2-yl)pyrazol-3-yl]phenyl]2,6-dichloropyridine4-carboxamide;
379. N-[3-[4-(1,3-naphth[2,3-d]oxazol-2-yl)pyrazol-3-yl]phenyl]2,6-dimethylbenzamide;
380. N-[3-[4-(1,3-naphth[2,3-d]oxazol-2-yl)pyrazol-3-yl]phenyl]2-acetamido-5-bromobenzamide;
381. N-[3-[4-(1,3-naphth[2,3-d]oxazol-2-yl)pyrazol-3-yl]phenyl]2-acetoxypropionamide;
382. N-[3-[4-(1,3-naphth[2,3-d]oxazol-2-yl)pyrazol-3-yl]phenyl]2-benzyloxyphenylacetamide.

As formerly indicated, it is a further object of the invention a process for preparing the compounds of formula (I) and pharmaceutically acceptable salts thereof, which process comprises:

a) reacting the compound of formula (II) with a suitable nitrogen-pyrazole protecting agent or a solid support

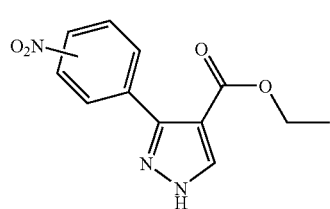
(II)

so as to obtain a compound of formula (III)

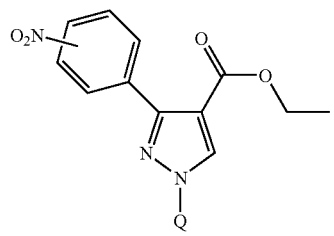
(III)

wherein Q is the said nitrogen-pyrazole protecting group or a solid support;

b) reacting the compound of formula (III) under basic conditions so as to obtain the compound of formula (IV)

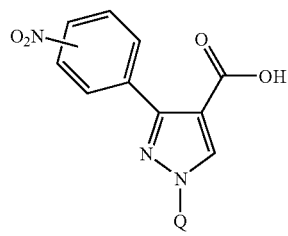
(IV)

wherein Q is as above defined;

c) reacting the compound of formula (IV) with a derivative of formula (V)

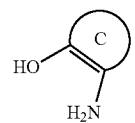
(V)

so as to obtain a compound of formula (VI)

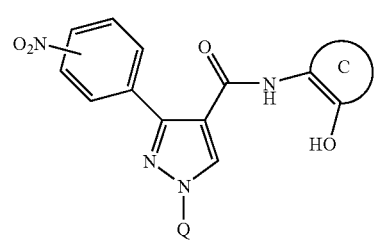
(VI)

wherein Q and C are as above defined;

d) reacting the compound of formula (VI) with a suitable azodicarboxylate derivative and a phosphine so as to obtain the compound of formula (VII)

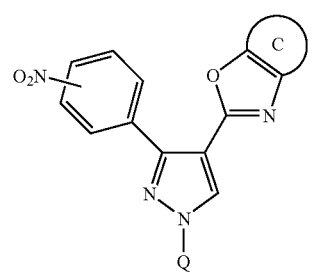
(VII)

wherein Q and C are as above defined;

e) reducing the compound of formula (VII) so as to obtain the compound of formula (VIII)

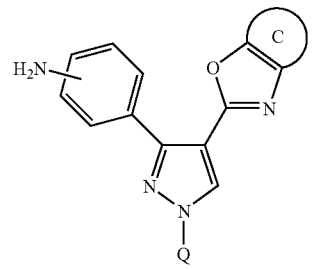
(VIII)

wherein Q and C are as above defined;

f) reacting the compound of formula (VIII) with any one of the compounds of formula (IX), (X) or (XI)

R—COX  (IX),

R—SO$_2$X'  (X),

R—NCO  (XI)

wherein R is as above defined, X is hydroxy or a suitable leaving group and X' is a suitable leaving group, so as to obtain the compound of formula (XII)

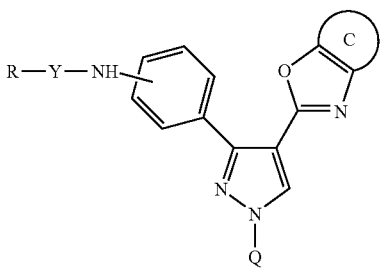

(XII)

wherein R, Q and C are as above defined and Y is a divalent group selected among (>C=O), (—SO$_2$—) or (—NHCO—); or, alternatively, reacting under reductive conditions the compound of formula (VIII) with a suitable aldehyde or ketone derivative of formula (XIII)

wherein R' and R" have the meanings reported for R, provided they are not both hydrogen atoms, so as to obtain the compound of formula (XII) wherein Q and C are as above defined, Y is a single bond and R is a group —CH(R')(R");

or, alternatively, reacting the compound of formula (VIII) with a suitable acylating agent in the presence of ammonia, so as to obtain the compound of formula (XII) wherein Q and C are as above defined, Y is aminocarbonyl (—NHCO—) and R is hydrogen;

g) deprotecting the compound of formula (XII) under acidic conditions so as to obtain the compound of formula (I) and, if desired, converting the said compound of formula (I) into another compound of formula (I) and/or into a salt thereof.

The above process is an analogy process which can be carried out according to well known methods.

It is clear to the person skilled in the art that if a compound of formula (I), prepared according to the above process, is obtained as an admixture of isomers, their separation into the single isomers of formula (I) carried out according to conventional techniques, is still within the scope of the present invention.

Likewise, the salification of a compound of formula (I) or the conversion of its salt into the free compound (I), carried out according to well-known procedures in the art, are still within the scope of the invention.

According to step a) of the process, the compound of formula (II) is reacted with a suitable nitrogen-pyrazole protecting agent such as, for instance, tert-butoxycarbonyl (BOC), di-tert-butyl dicarbonate, 2-(tert-butoxycarbonyloxymino)-2-phenylacetonitrile, chlorotriphenylmethane or trityl; or with a solid support such as, for instance, a trityl chloride resin or a chlorotrityl chloride resin.

Preferably, the nitrogen-pyrazole protecting agent or the solid support is selected from di-tert-butyl dicarbonate or a trityl chloride resin.

The reaction is carried out in the presence of a tertiary base such as triethylamine, N,N-diisopropylethylamine or pyridine, in a suitable solvent such as, for instance, dichloromethane, chloroform, tetrahydrofuran, acetonitrile, diethyl ether, 1,4-dioxane or N,N-dimethylformamide, at a temperature ranging from about 0° C. to room temperature and for a suitable time, for instance from about 30 minutes to about 96 hours.

According to step b) of the process, the compound of formula (III) is reacted under basic hydrolysis conditions, for instance in the presence of a conventional aqueous base such as sodium, potassium or lithium hydroxide.

The reaction is carried out in a suitable solvent such as, for instance, N,N-dimethylformamide, ethanol, methanol or tetrahydrofuran, at a temperature comprised from about 20° C. to reflux and for a suitable time, for instance from about 30 minutes to about 96 hours.

According to step c) of the process, the reaction between a compound of formula (IV) and a derivative of formula (V) can be carried out in the presence of a coupling agent such as, for instance, benzotriazol-1-yloxytris(pyrrolidino)phosphonium hexafluorophosphatecarbodiimide, 1,3-dicyclohexylcarbodiimide, bromo-tris-pyrrolidino-phosphonium hexafluorophosphate, 1,3-diisopropylcarbodiimide, o-benzotriazol-1-yl-n,n,n',n'-tetramethyluronium tetrafluoroborate, 1-(3-dimethylaminopropyl)-3-ethylcarbodiimide, N-cyclohexylcarbodiimide-N'-propyloxymethyl polystyrene or N-cyclohexylcarbodiimide-N'-methyl polystyrene, in a suitable solvent such as, for instance, dichloromethane, chloroform, tetrahydrofuran, diethyl ether, 1,4-dioxane, acetonitrile, toluene, or N,N-dimethylformamide, and at a temperature ranging from about −10° C. to reflux for a suitable time, for instance from about 30 minutes to about 96 hours.

The said reaction is optionally carried out in the presence of a suitable catalyst, for instance 4-dimethylaminopyridine, or in the presence of a further coupling agent such as N-hydroxybenzotriazole.

The reaction between a compound of formula (IV) and a compound of formula (V) can be also carried out, for example, through a mixed anhydride method by using an alkyl chloroformate, such as ethyl, isobutyl, or isopropyl chloroform ate, in the presence of a tertiary base such as triethylamine, N,N-diisopropylethylamine or pyridine, in a suitable solvent such as, for instance, toluene, dichloromethane, chloroform, tetrahydrofuran, acetonitrile, diethyl ether, 1,4-dioxane, or N,N-dimethylformamide, and at a temperature ranging from about −30° C. to room temperature.

According to step d) of the process, the compound of formula (VI) is reacted with a suitable azodicarboxylate derivative and a phosphine. Suitable azodicarboxylate derivatives are, as an example, diethyl azodicarboxylate, diisopropyl azodicarboxylate or di-tert-butyl azodicarboxylate; diethyl azodicarboxylate being preferred.

A suitable phosphine is, for instance, triphenylphosphine, tri-n-butylphosphine, tricyclohexylphosphine or triethylphosphine; tri-n-butylphosphine being preferred.

The reaction is carried out in a suitable solvent such as, for instance, tetrahydrofuran, toluene, dichloromethane, 1,4-dioxane or N,N-dimethylformamide, at a temperature ranging from about −10° C. to reflux and for a suitable time ranging from about 30 minutes to about 96 hours.

According to step e) of the process, the compound of formula (VII) is converted into the corresponding amino derivative of formula (VIII) under reductive conditions.

The reaction may be thus carried out in the presence of a reducing agent such as, for instance, tin (II) chloride, sodium borohydride, sodium dithionite, ammonium formate or chromium (II) chloride; tin (II) chloride being preferred.

The reaction may occur in a suitable solvent such as, for instance, N,N-dimethylformamide, 1,4-dioxane, 1-methyl-2-pyrrolidinone or acetonitrile, at a temperature ranging from −10° C. to reflux and for a suitable time, for instance from about 30 minutes to about 96 hours.

The said reduction may be also performed as a catalytic hydrogenation, according to conventional techniques, in the presence of a suitable catalyst such as, for instance, copper (II) acetate, palladium on charcoal or 4-dimethylaminopyridine.

According to step f) of the process, the compound of formula (VIII) is reacted with any one of the compounds of formula (IX), (X) or (XI), so as to obtain the corresponding derivative of formula (XII). In this respect, it is clear to the skilled man that a carboxamido derivative of formula (XII) wherein Y is (>C=O) is obtained through reaction with a compound of formula (IX); a sulphonamido derivative of formula (XII) wherein Y is (—$SO_2$—) is obtained through reaction with a compound of formula (X); and an ureido derivative of formula (XII) wherein Y is (—NHCO—) is obtained though reaction with a compound of formula (XI).

As formerly indicated, within the compound of formula (X) X is hydroxy or a suitable leaving group such as, for instance, a halogen atom. Preferably, in the reaction with a compound of formula (IX) X is hydroxy, chlorine or bromine.

The reaction between a compound of formula (VIII) and a carboxylic acid derivative of formula (IX) wherein X is hydroxy can be carried out in the presence of a coupling agent such as, for instance, benzotriazol-1-yloxytris(pyrrolidino)phosphonium hexafluorophosphatecarbodiimide, 1,3-dicyclohexylcarbodiimide, bromo-tris-pyrrolidino-phosphonium hexafluorophosphate, 1,3-diisopropylcarbodiimide, o-benzotriazol-1-yl-n,n,n',n'-tetramethyluronium tetrafluoroborate, 1-(3-dimethylaminopropyl)-3-ethylcarbodiimide, N-cyclohexylcarbodiimide-N'-propyloxymethyl polystyrene or N-cyclohexylcarbodiimide-N'-methyl polystyrene, in a suitable solvent such as, for instance, dichloromethane, chloroform, tetrahydrofuran, diethyl ether, 1,4-dioxane, acetonitrile, toluene or N,N-dimethylformamide, at a temperature ranging from about −10° C. to reflux and for a suitable time ranging from about 30 minutes to about 96 hours.

The said reaction is optionally carried out in the presence of a suitable catalyst, for instance 4-dimethylaminopyridine, or in the presence of a further coupling agent such as N-hydroxybenzotriazole. The reaction between a compound of formula (VIII) and a compound of formula (IX) can also be carried out through a mixed anhydride method, that is by using an alkyl chloroformate such as ethyl, isobutyl, or isopropyl chloroformate, in the presence of a tertiary base such as triethylamine, N,N-diisopropylethylamine or pyridine, in a suitable solvent such as toluene, dichloromethane, chloroform, tetrahydrofuran, acetonitrile, diethyl ether, 1,4-dioxane or N,N-dimethylformamide, and at a temperature ranging from about −30° C. to room temperature.

The reaction between a compound of formula (VIII) and a compound of formula (IX) wherein X is a suitable leaving group, for instance chlorine or bromine, can be carried out in the presence of a tertiary base such as triethylamine, N,N-diisopropylethylamine or pyridine, in a suitable solvent such as toluene, dichloromethane, chloroform, diethyl ether, tetrahydrofuran, acetonitrile or N,N-dimethylformamide, and at a temperature ranging from about −10° C. to reflux.

As per step f) of the process, within the compound of formula (X) X' is a suitable leaving group such as, for instance, a halogen atom. Preferably, X' is chlorine or bromine.

The reaction between a compound of formula (VIII) and a sulphonyl derivative of formula (X) can be carried out in the presence of a tertiary base such as triethylamine, N,N-diisopropylethylamine or pyridine, in a suitable solvent such as toluene, dichloromethane, chloroform, diethyl ether, tetrahydrofuran, acetonitrile or N,N-dimethylformamide, at a temperature ranging from about −10° C. to reflux.

As per step f) of the process, the reaction between a compound of formula (VIII) and an isocyanate derivative of formula (XI) can be carried out in the presence of a tertiary base such as triethylamine, N,N-diisopropylethylamine or pyridine, in a suitable solvent such as toluene, dichloromethane, chloroform, diethyl ether, tetrahydrofuran, acetonitrile, or N,N-dimethylformamide, and at a temperature ranging from about −10° C. to reflux.

Alternatively, as per step f) of the process, the compound of formula (VIII) is reacted under reductive conditions with a aldehyde or ketone derivative of formula (XIII) so as to obtain the corresponding compound of fomula (XII) wherein R is as above defined. From the above, it is clear to the skilled man that by reacting an aldehyde derivative of formula (XIII), for instance wherein R" is a hydrogen atom, the corresponding derivative of formula (XII) wherein R is a —$CH_2$-R' group will be obtained; likewise, by reacting a ketone derivative of formula (XIII), both R' and R" groups will be part of the R group of the compound of formula (XII) thus prepared.

This reaction, widely known as reductive alkylation of amines, occurs in the presence of a reducing agent such as, for instance, sodium borohydride, sodium cyanoborohydride or sodium triacetoxyborohydride, in a suitable solvent such as N,N-dimethylformamide, N,N-dimethylacetamide, chloroform, dichloromethane, tetrahydrofuran or acetonitrile, optionally in the presence of acetic acid, methanol or ethanol as co-solvents, at a temperature ranging from about −10° C. to reflux and for a time varying from about 30 minutes to about 96 hours.

Finally, as far as step f) of the process is concerned, ureido derivatives of formula (XII) wherein R is hydrogen and Y is (—NHCO—) may be prepared by reacting the compound of formula (VIII) with a suitable acylating agent, for instance triphosgene or trichloromethyl chloroformate, in the presence of aqueous or gaseous ammonia, according to conventional techniques.

The said reaction is carried out in a suitable solvent such as, for instance, dichloromethane, chloroform, toluene, tetrahydrofuran or dioxane, optionally in the presence of a tertiary base, for instance triethylamine, and of a catalyst such as 4-dimethylaminopyridine, at a temperature ranging from about −10° C. to room temperature and for a time varying from about 30 minutes to about 96 hours.

According to step g) of the process, the compound of formula (XII) is treated or deprotected under acidic conditions, that is in the presence of suitable acids such as, for instance, hydrochloric, trifluoroacetic, methanesulphonic or p-toluensulphonic acid, as well as by using conventional acid ion exchange resins.

The reaction is carried out under conventional methods, for instance by using a solution of the acid, e.g. a 10% to 100% (v/v) of trifluoroacetic acid in dichlorometane, at a temperature ranging from about 0° C. to reflux, and for a suitable time, for instance from about 5 minutes to about 2 hours.

From the above it is clear to the skilled man that the optional conversion of a compound of formula (I) into another compound of formula (I) may be carried out by conventional methods. Likewise, a compound of formula (XII) may be converted into another compound of formula (XII) before undergoing deprotection.

As an example, an alkylcarboxamido derivative of formula (XII) wherein Y is carbonyl (>C=O) may be conveniently reduced to the corresponding amino derivative of formula (XII) wherein Y is a single bond by working according to conventional methods, and subsequently converted into the compound of formula (I) as per step g) of the process.

Also the optional salification of a compound of formula (I) or the conversion of its salt into the free compound, as well as the separation of a mixture of isomers into the single isomers, may be all carried out by conventional methods.

Within the aforementioned process for preparing the compounds of formula (I), the intermediate derivatives of formula (VIII) are novel and, hence, represent a further object of the invention.

The compounds of formula (II), (V), (IX), (X), (XI) and (XIII) of the process are known or can be prepared according to known methods. As an example, the above compounds of formula (II) can be prepared according to the procedure described in: Et-Abadelah, M. M. et al., *Eur. J. Med. Chem.*, 33 (1998) 33–42.

As it will be really appreciated by the man skilled in the art, when preparing the compounds of formula (I) object of the invention, optional functional groups within both the starting materials or the intermediates thereof which could give rise to unwanted side reactions, need to be properly protected according to conventional techniques. Likewise, the conversion of these latter into the free deprotected compounds may be carried out according to known procedures.

In addition to the above, it is also clear to the skilled man that the compounds of formula (I) of the invention can be advantageously prepared by combining the above described reactions in a combinatorial fashion, for example according to solid-phase-synthesis (SPS) techniques, so as to get a combinatorial chemical library of compounds of formula (I).

It is therefore a further object of the invention a library of two or more compounds of formula (I)

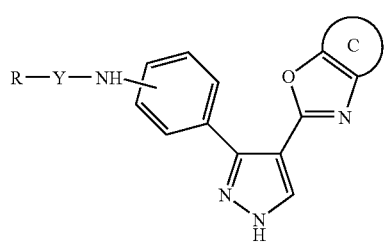

(I)

wherein

R represents a hydrogen atom; a straight or branched $C_1$–$C_8$ alkyl group; a straight or branched $C_2$–$C_8$ alkenyl group; an aryl or aryl $C_1$–$C_6$ alkyl group; a saturated or unsaturated $C_3$–$C_6$ cycloalkyl or cycloalkyloxy group optionally further condensed with 1 or 2 benzene rings; or it is an optionally benzocondensed 5 or 6 membered heterocyclic or heterocyclyl $C_1$–$C_6$ alkyl group, having 1 or 2 heteroatoms selected among nitrogen, oxygen or sulfur; each of the above defined R groups being optionally further substituted by one or more groups selected from:

i) halogen, nitro, cyano, hydroxy, oxo groups (═O);

ii) straight or branched $C_1$–$C_6$ alkyl, alkoxyalkyl or perfluorinated alkyl;

iii) aryl or 5 or 6 membered heterocycles having 1 or 2 heteroatoms selected among nitrogen, oxygen or sulfur, optionally substituted by halogen, nitro, cyano, $C_1$–$C_6$ alkyl or alkoxy;

iv) straight or branched $C_1$–$C_6$ alkoxy, alkoxyalkyloxy, arylalkyloxy or aryloxy optionally substituted by halogen, nitro, cyano, $C_1$–$C_6$ alkyl or alkoxy;

v) straight or branched $C_1$–$C_6$ alkylthio or alkylsulphonyl, arylthio or arylsulphonyl;

vi) $C_3$–$C_6$ cycloalkyl;

vii) amino, $C_1$–$C_6$ alkylamino, dialkylamino or arylamino;

viii) $C_1$–$C_6$ alkylcarbonyl, alkyloxycarbonyl, alkylaminocarbonyl, aminocarbonyl, arylcarbonyl or heterocyclylcarbonyl optionally substituted by halogen, nitro, cyano, $C_1$–$C_6$ alkyl or alkoxy;

ix) $C_1$–$C_6$ alkylcarbonylamino, alkyloxycarbonylamino, arylalkyloxycarbonylamino, arylcarbonylamino or aryloxycarbonylamino;

x) carboxy, $C_1$–$C_6$ alkylcarbonyloxy or arylcarbonyloxy;

Y is a single bond or a divalent group selected from carbonyl (>C═O), aminocarbonyl (—NHCO—) or sulphonyl (—SO$_2$—);

C is benzene, naphthalene or an optionally benzocondensed 5 or 6 membered heterocycle having 1 or 2 heteroatoms selected among nitrogen, oxygen or sulphur; each of which being optionally further substituted by one or more groups selected from halogen, nitro, cyano, straight or branched $C_1$–$C_6$ alkyl or alkoxy, alkylsulphonyl or aryl groups;

or pharmaceutically acceptable salts thereof.

All of the compounds of formula (I) which are prepared according to combinatorial chemistry techniques, for instance as reported in the examples, whenever appropriate in the form of pharmaceutically acceptable salts, are herewith conveniently indicated and defined as "products by process", that is as compounds of formula (I) which are obtainable through a given process.

As such, it is a further object of the present invention a compound of formula (I) which is obtainable, for instance through a combinatorial chemistry technique, by reacting each of the amino derivatives of formula (VIII), as set forth in table I, with any one of the carboxylic acid derivatives of formula (IX), as set forth in table II, and by subsequently operating as per the process of the invention.

It is a further object of the present invention a compound of formula (I) which is obtainable, for instance through a combinatorial chemistry technique, by reacting each of the amino derivatives of formula (VIII), as set forth in table I, with any one of the isocyanate derivatives of formula (XI), as set forth in table III, and by subsequently operating as per the process of the invention.

It is a further object of the present invention a compound of formula (I) which is obtainable, for instance through a combinatorial chemistry technique, by reacting each of the amino derivatives of formula (VIII), as set forth in table I, with any one of the sulphonyl chloride derivatives of formula (X), as set forth in table IV, and by subsequently operating as per the process of the invention.

TABLE I

Amino derivatives of formula (VIII)

1. 2-[3-(3-aminophenyl)-1-tritylpolystyrene-1H-pyrazol-4-yl]-1,3-benzoxazole
2. 2-[3-(3-aminophenyl)-1-tritylpolystyrene-1H-pyrazol-4-yl]-1,3-naphth[2,3-d]oxazole
3. 2-[3-(3-aminophenyl)-1-tritylpolystyrene-1H-pyrazol-4-yl]-1,3-oxazolo[4,5-b]pyridine
4. 2-[3-(3-aminophenyl)-1-tritylpolystyrene-1H-pyrazol-4-yl]-6-methyl-1,3-benzoxazole
5. 2-[3-(3-aminophenyl)-1-tritylpolystyrene-1H-pyrazol-4-yl]-5-chloro-1,3-benzoxazole
6. 2-[3-(3-aminophenyl)-1-tritylpolystyrene-1H-pyrazol-4-yl]-5-tbutyl-1,3-benzoxazole
7. 2-[3-(3-aminophenyl)-1-tritylpolystyrene-1H-pyrazol-4-yl]-5-methyl-1,3-benzoxazole
8. 2-[3-(3-aminophenyl)-1-tritylpolystyrene-1H-pyrazol-4-yl]-1,3-naphth[1,2-d]oxazole
9. 2-[3-(3-aminophenyl)-1-tritylpolystyrene-1H-pyrazol-4-yl]-5,7-chloro-6-methyl-1,3-benzoxazole
10. 2-[3-(3-aminophenyl)-1-tritylpolystyrene-1H-pyrazol-4-yl]-5-ethylsulfonyl-1,3-benzoxazole
11. 2-[3-(3-aminophenyl)-1-tritylpolystyrene-1H-pyrazol-4-yl]-5-phenyl-1,3-benzoxazole
12. 2-[3-(3-aminophenyl)-1-tritylpolystyrene-1H-pyrazol-4-yl]-4-methyl-7-isopropyl-1,3-benzoxazole
13. 2-[3-(3-aminophenyl)-1-tritylpolystyrene-1H-pyrazol-4-yl]-4-methyl-1,3-benzoxazole
14. 2-[3-(4-aminophenyl)-1-tritylpolystyrene-1H-pyrazol-4-yl]-1,3-benzoxazole
15. 2-[3-(4-aminophenyl)-1-tritylpolystyrene-1H-pyrazol-4-yl]-1,3-naphth[2,3-d]oxazole
16. 2-[3-(4-aminophenyl)-1-tritylpolystyrene-1H-pyrazol-4-yl]-1,3-oxazolo[4,5-b]pyridine
17. 2-[3-(4-aminophenyl)-1-tritylpolystyrene-1H-pyrazol-4-yl]-6-methyl-1,3-benzoxazole
18. 2-[3-(4-aminophenyl)-1-tritylpolystyrene-1H-pyrazol-4-yl]-5-chloro-1,3-benzoxazole
19. 2-[3-(4-aminophenyl)-1-tritylpolystyrene-1H-pyrazol-4-yl]-5-tbutyl-1,3-benzoxazole
20. 2-[3-(4-aminophenyl)-1-tritylpolystyrene-1H-pyrazol-4-yl]-5-methyl-1,3-benzoxazole
21. 2-[3-(4-aminophenyl)-1-tritylpolystyrene-1H-pyrazol-4-yl]-1,3-naphth[1,2-d]oxazole
22. 2-[3-(4-aminophenyl)-1-tritylpolystyrene-1H-pyrazol-4-yl]-5,7-chloro-6-methyl-1,3-benzoxazole
23. 2-[3-(4-aminophenyl)-1-tritylpolystyrene-1H-pyrazol-4-yl]-5-ethylsulfonyl-1,3-benzoxazole
24. 2-[3-(4-aminophenyl)-1-tritylpolystyrene-1H-pyrazol-4-yl]-5-phenyl-1,3-benzoxazole
25. 2-[3-(4-aminophenyl)-1-tritylpolystyrene-1H-pyrazol-4-yl]-4-methyl-7-isopropyl-1,3-benzoxazole
26. 2-[3-(4-aminophenyl)-1-tritylpolystyrene-1H-pyrazol-4-yl]-4-methyl-1,3-benzoxazole

TABLE II

Carboxylic acid derivatives of formula (IX)

1. 9-FLUORENECARBOXYLIC ACID;
2. 1-PHENYL-1-CYCLOPROPANECARBOXYLIC ACID;
3. 1-METHYLCYCLOPROPANE-1-CARBOXYLIC ACID;
4. CYCLOBUTANECARBOXYLIC ACID;
5. CYCLOPENTANECARBOXYLIC ACID;
6. (−)-MENTHOXYACETIC ACID;
7. 1,2,3,4-TETRAHYDRO-2-NAPHTHOIC ACID;
8. 2-FLUOROBENZOIC ACID;
9. 2,5-DIMETHOXYBENZOIC ACID;
10. 2-BIPHENYLCARBOXYLIC ACID;
11. 2-(4-CHLOROBENZOYL)BENZOIC ACID;
12. 2,6-DIMETHYLBENZOIC ACID;
13. 3-CYANOBENZOIC ACID;
14. 3-BROMOBENZOIC ACID;
15. 3,4-DIMETHOXYBENZOIC ACID;
16. 3,4,5-TRIMETHOXYBENZOIC ACID;
17. 3,4-DIETHOXYBENZOIC ACID;
18. 4-CYANOBENZOIC ACID;
19. 4-IODOBENZOIC ACID;
20. 4-DIETHYLAMINOBENZOIC ACID;
21. 4-BIPHENYLCARBOXYLIC ACID;
22. 3-METHYL-2-OXOVALERIC ACID;
23. PYRUVIC ACID;
24. 2-METHYLVALERIC ACID;
25. TERT-BUTYLACETIC ACID;
26. 3-(2-METHOXYPHENYL)PROPIONIC ACID;
27. 5-NITRO-2-FUROIC ACID;
28. 1-NAPHTHOIC ACID;
29. 2-NAPHTHOIC ACID;
30. 2-KETOBUTYRIC ACID;
31. PIVALIC ACID;
32. 2,2-DIMETHYLBUTYRIC ACID;
33. DIPHENYLACETIC ACID;
34. N,N-DIMETHYLGLYCINE;
35. 2,3-DICHLOROPHENOXYACETIC ACID;

TABLE II-continued

Carboxylic acid derivatives of formula (IX)

36. PHENYLACETIC ACID;
37. 2,4-DICHLOROPHENYLACETIC ACID;
38. 3-FLUOROPHENYLACETIC ACID;
39. 4-ETHOXYPHENYLACETIC ACID;
40. P-TOLYLACETIC ACID;
41. 4-PENTYNOIC ACID;
42. MONO-METHYL GLUTARATE;
43. MONOMETHYL ADIPATE;
44. 6-ACETAMIDOHEXANOIC ACID;
45. L-PYROGLUTAMIC ACID;
46. 3-FUROIC ACID;
47. THIOPHENE-3-CARBOXYLIC ACID;
48. THIOPHENE-3-ACETIC ACID;
49. NICOTINIC ACID;
50. NALIDIXIC ACID;
51. 2-NITRO-4-TRIFLUOROMETHYLBENZOIC ACID;
52. 4-METHYL-3-NITROBENZOIC ACID;
53. 3-NITROBENZOIC ACID;
54. 3-NITROPHENYLACETIC ACID;
55. 4-CARBOXYBENZENESULFONAMIDE;
56. SUCCINAMIC ACID;
57. N-(4-NITROBENZOYL)-BETA-ALANINE;
58. 3-(PHENYLSULFONYL)PROPIONIC ACID;
59. 2,2,3,3-TETRAMETHYLCYCLOPROPANECARBOXYLIC ACID;
60. 2-(4-NITROPHENYL)PROPIONIC ACID;
61. 2,2-DIMETHYL-4-PENTENOIC ACID;
62. 3-(DIETHYLAMINO)PROPIONIC ACID HYDROCHLORIDE;
63. 4-DIMETHYLAMINOBUTYRIC ACID HYDROCHLORIDE;
64. 4-ISOPROPYLPHENOXYACETIC ACID;
65. 5-BENZOYLPENTANOIC ACID;
66. 4-ACETAMIDO-3-NITROBENZOIC ACID;
67. D-CAMPHOLIC ACID;
68. 2,5-DIBROMOBENZOIC ACID;
69. 3-ACETOXYBENZOIC ACID;
70. 2,4,6-TRIMETHOXYPHENYLACETIC ACID;
71. 2-BENZYLOXYPHENYLACETIC ACID;
72. (3,5-DIMETHOXYPHENYL)ACETIC ACID;
73. 2-NITROPHENOXYACETIC ACID;
74. CHROMONE-3-CARBOXYLIC ACID;
75. N-ACETYL-4-FLUORO-DL-PHENYLALANINE;
76. N-M-TOLYLPHTHALAMIC ACID;
77. 4-ACETAMIDOBUTYRIC ACID;
78. 3-(2-THENOYL)-PROPIONIC ACID;
79. 3,5-DIACETAMIDOBENZOIC ACID;
80. 5-ACETAMIDO-2-NITROBENZOIC ACID;
81. ACETIC ACID;
82. 5-METHYLHEXANOIC ACID;
83. N-BENZOYL-B-ALANINE;
84. 4-BROMO-3-METHYLBENZOIC ACID;
85. 4,5-DIBROMOTHIOPHENE-2-CARBOXYLIC ACID;
86. 2-ACETAMIDO-5-BROMOBENZOIC ACID;
87. 4-BROMO-2-METHYLBENZOIC ACID;
88. 2-FLUORO-6-IODOBENZOIC ACID;
89. 2-FURANGLYOXYLIC ACID;
90. N,N-DIMETHYLSUCCINAMIC ACID;
91. 2-(2-METHOXYETHOXY)ACETIC ACID;
92. 4-CHLORO-ALPHA-METHYLPHENYLACETIC ACID;
93. 1-(P-TOLYL)-1-CYCLOPENTANECARBOXYLIC ACID;
94. PICOLINIC ACID HYDROCHLORIDE;
95. 3,5-DIBROMOBENZOIC ACID;
96. 5-CHLOROTHIANAPHTHENE-3-ACETIC ACID;
97. 2-NITROTHIOPHENE-4-CARBOXYLIC ACID;
98. 3-CHLORO-2-METHYLBENZOIC ACID;
99. 2-BROMO-4-FLUOROBENZOIC ACID;
100. 3-(2-CHLORO-6-FLUOROPHENYL)-5-METHYLISOXAZOLE-4-CARBOXYLIC ACID;
101. FENBUFEN;
102. INDOPROFEN;
103. CHRYSANTHEMUM MONOCARBOXYLIC ACID;
104. 6-ACETOXY-2-NAPHTHOIC ACID;
105. 3-METHYLTHIOPROPIONIC ACID;
106. (R)-(+)-N-(1-PHENYLETHYL)PHTHALAMIC ACID;
107. ALPHA-KETOVALERIC ACID;
108. 5-METHYL-1-PHENYLPYRAZOLE-4-CARBOXYLIC ACID;
109. 3-METHYL-1-CYCLOHEXANECARBOXYLIC ACID;
110. 3-METHOXYCYCLOHEXANECARBOXYLIC ACID;
111. DICYCLOHEXYLACETIC ACID;

TABLE II-continued

Carboxylic acid derivatives of formula (IX)

112. 5,6-DICHLORONICOTINIC ACID;
113. 4-(DIMETHYLAMINO)PHENYLACETIC ACID;
114. (R)-(+)-N-(1-PHENYLETHYL)SUCCINAMIC ACID;
115. (S)-(−)-N-(1-PHENYLETHYL)SUCCNAMIC ACID;
116. (+)-MENTHYLOXYACETIC ACID;
117. SUPROFEN;
118. N,N-DIMETHYL-L-PHENYLALANINE;
119. 4-IODOPHENYLACETIC ACID;
120. 4-(3,4-DIMETHOXYPHENYL)BUTYRIC ACID;
121. 2-FLUORO-5-NITROBENZOIC ACID;
122. N,N-DIETHYL-3,6-DIFLUOROPHTHALAMIC ACID;
123. 2-BROMO-5-NITROBENZOIC ACID;
124. 4-BROMO-2-FLUOROBENZOIC ACID;
125. 5-(2-THIENYL)PENTANOIC ACID;
126. ISOXAZOLE-5-CARBOXYLIC ACID;
127. 5-NITROTHIOPHENE-2-CARBOXYLIC ACID;
128. 2-(4-PYRIDYL)THIAZOLE-4-CARBOXYLIC ACID;
129. 2-METHYL-4,4,4-TRIFLUOROBUTYRIC ACID;
130. 1-(AMINOCARBONYL)-1-CYCLOPROPANECARBOXYLIC ACID;
131. 1-CYANOCYCLOPROPANECARBOXYLIC ACID;
132. (S)-(−)-2-ACETOXYPROPIONIC ACID;
133. 3-(METHYLSULFONYL)BENZOIC ACID;
134. 2-CHLORO-4-METHYLSULFONYLBENZOIC ACID;
135. 2,6-DICHLOROPYRIDINE-4-CARBOXYLIC ACID;
136. 3-PYRIDINEPROPIONIC ACID;
137. 5-(4-CHLORO-2-NITROPHENYL)-2-FUROIC ACID;
138. 7-CHLORO-1-ETHYL-6-FLUORO-4-OXOHYDROQUINOLINE-3-CARBOXYLIC ACID;
139. CIS-2-(2-THIOPHENECARBONYL)-1-CYCLOHEXANECARBOXYLIC ACID;
140. 5-BROMO-3-PYRIDYLACETIC ACID;
141. 5-METHYLISOXAZOLE-4-CARBOXYLIC ACID;
142. 2,2-DIMETHYLHEXANOIC ACID;
143. 3-CARBOXYPROPANESULFONAMIDE;
144. 6-CYANONICOTINIC ACID;
145. (R)-(−)-2-METHOXYPROPIONIC ACID;
146. (S)-(+)-2-METHOXYPROPIONIC ACID;
147. 4-(TERT-BUTOXYMETHYL)BENZOIC ACID;
148. CIS-2-(BENZYLOXYCARBONYLAMINO)-CYCLOHEXANECARBOXYLIC ACID;
149. CIS-2-(BENZYLOXYCARBONYLAMINO)-4-CYCLOHEXENE-1-CARBOXYLIC ACID.

TABLE III

Isocyanate derivatives of formula (XI)

1. PHENYL ISOCYANATE
2. 2-BROMOPHENYL ISOCYANATE
3. 2-FLUOROPHENYL ISOCYANATE
4. 2,4-DIFLUOROPHENYL ISOCYANATE
5. 2,6-DIFLUOROPHENYL ISOCYANATE
6. 2-CHLOROPHENYL ISOCYANATE
7. 2,3-DICHLOROPHENYL ISOCYANATE
8. 2,4-DICHLOROPHENYL ISOCYANATE
9. 2,5-DICHLOROPHENYL ISOCYANATE
10. 2,6-DICHLOROPHENYL ISOCYANATE
11. 2-METHOXYPHENYL ISOCYANATE
12. 2,4-DIMETHOXYPHENYL ISOCYANATE
13. 2,5-DIMETHOXYPHENYL ISOCYANATE
14. 2-ETHOXYPHENYL ISOCYANATE
15. 2-(TRIFLUOROMETHYL)PHENYL ISOCYANATE
16. O-TOLYL ISOCYANATE
17. 2,6-DIMETHYLPHENYL ISOCYANATE
18. 2-ETHYLPHENYL ISOCYANATE
19. 3-BROMOPHENYL ISOCYANATE
20. 3-FLUOROPHENYL ISOCYANATE
21. 3-CHLOROPHENYL ISOCYANATE
22. 3,4-DICHLOROPHENYL ISOCYANATE
23. 3-METHOXYPHENYL ISOCYANATE
24. 3-(TRIFLUOROMETHYL)PHENYL ISOCYANATE
25. M-TOLYL ISOCYANATE
26. 4-BROMOPHENYL ISOCYANATE
27. 4-FLUOROPHENYL ISOCYANATE
28. 4-CHLOROPHENYL ISOCYANATE
29. 4-METHOXYPHENYL ISOCYANATE
30. 4-(TRIFLUOROMETHYL)PHENYL ISOCYANATE
31. P-TOLYL ISOCYANATE
32. BENZOYL ISOCYANATE
33. TERT-BUTYL ISOCYANATE
34. (S)-(−)-1-PHENYLETHYL ISOCYANATE
35. ISOPROPYL ISOCYANATE
36. ETHYL ISOCYANATE
37. ALLYL ISOCYANATE
38. N-PROPYL ISOCYANATE
39. N-BUTYL ISOCYANATE
40. CYCLOHEXYL ISOCYANATE
41. 1-NAPHTHYL ISOCYANATE
42. (R)-(−)-1-(1-NAPHTHYL)ETHYL ISOCYANATE
43. BENZYL ISOCYANATE
44. 3,5-BIS(TRIFLUOROMETHYL)PHENYL ISOCYANATE
45. 2,5-DIFLUOROPHENYL ISOCYANATE
46. 2,4,5-TRICHLOROPHENYL ISOCYANATE
47. 2,4,6-TRICHLOROPHENYL ISOCYANATE
48. 2-ISOPROPYLPHENYL ISOCYANATE
49. 2,3-DIMETHYLPHENYL ISOCYANATE
50. 4-METHOXY-2-METHYLPHENYL ISOCYANATE
51. 2,4-DIMETHYLPHENYL ISOCYANATE
52. 2,5-DIMETHYLPHENYL ISOCYANATE
53. 2-ETHYL-6-METHYLPHENYL ISOCYANATE
54. 3-CYANOPHENYL ISOCYANATE

TABLE III-continued

Isocyanate derivatives of formula (XI)

55. 5-CHLORO-2,4-DIMETHOXYPHENYL ISOCYANATE
56. 3-CHLORO-4-METHYLPHENYL ISOCYANATE
57. 3,5-DICHLOROPHENYL ISOCYANATE
58. 5-CHLORO-2-METHOXYPHENYL ISOCYANATE
59. 3,4,5-TRIMETHOXYPHENYL ISOCYANATE
60. 3,5-DIMETHOXYPHENYL ISOCYANATE
61. 3-(METHYLTHIO)PHENYL ISOCYANATE
62. 3-ACETYLPHENYL ISOCYANATE
63. 3,4-DIMETHYLPHENYL ISOCYANATE
64. 3,5-DIMETHYLPHENYL ISOCYANATE
65. 2-METHOXY-5-METHYLPHENYL ISOCYANATE
66. 3-ETHYLPHENYL ISOCYANATE
67. 4-BROMO-2-(TRIFLUOROMETHYL)PHENYL ISOCYANATE
68. 4-CHLORO-2-(TRIFLUOROMETHYL)PHENYL ISOCYANATE
69. 4-CHLORO-3-(TRIFLUOROMETHYL)PHENYL ISOCYANATE
70. 4-IODOPHENYL ISOCYANATE
71. 4-PHENOXYPHENYL ISOCYANATE
72. 4-ETHOXYPHENYL ISOCYANATE
73. 4-ACETYLPHENYL ISOCYANATE
74. 4-ISOPROPYLPHENYL ISOCYANATE
75. 4-ETHYLPHENYL ISOCYANATE
76. 4-N-BUTYLPHENYL ISOCYANATE
77. 2,4,6-TRIMETHYLPHENYL ISOCYANATE
78. 2-ISOPROPYL-6-METHYLPHENYL ISOCYANATE
79. 2,6-DIETHYLPHENYL ISOCYANATE
80. 5-CHLORO-2-METHYLPHENYL ISOCYANATE
81. 4-CHLORO-2-METHYLPHENYL ISOCYANATE
82. 4-(TRIFLUOROMETHOXY)PHENYL ISOCYANATE
83. 3-CHLORO-5-(TRIFLUOROMETHYL)PHENYL ISOCYANATE
84. 2-CHLORO-6-METHYLPHENYL ISOCYANATE
85. 2,4,5-TRIMETHYLPHENYL ISOCYANATE
86. 3-CHLORO-2-METHOXYPHENYL ISOCYANATE
87. 3-CHLORO-2-METHYLPHENYL ISOCYANATE
88. 3-CHLORO-4-FLUOROPHENYL ISOCYANATE
89. 4-BROMO-2-METHYLPHENYL ISOCYANATE
90. 4-BROMO-2,6-DIMETHYLPHENYL ISOCYANATE
91. 2,6-DIBROMO-4-FLUOROPHENYL ISOCYANATE
92. 4-BUTOXYPHENYL ISOCYANATE
93. 3-FLUORO-4-METHYLPHENYL ISOCYANATE
94. 5-FLUORO-2-METHYLPHENYL ISOCYANATE
95. 2-BIPHENYLYL ISOCYANATE
96. 4-BIPHENYLYL ISOCYANATE
97. 2-BROMO-4,6-DIFLUOROPHENYL ISOCYANATE
98. (R)-(+)-1-PHENYLETHYL ISOCYANATE
99. 1-(1-NAPHTHYL)ETHYL ISOCYANATE
100. (S)-(+)-1-(1-NAPHTHYL) ETHYL ISOCYANATE
101. 3,4-DIFLUOROPHENYL ISOCYANATE
102. 3-ISOPROPENYL-ALPHA,ALPHA-DIMETHYLBENZYL ISOCYANATE
103. 2-(TRIFLUOROMETHOXY)PHENYL ISOCYANATE
104. 4-BENZYLOXYPHENYL ISOCYANATE
105. 4-BROMO-2-CHLOROPHENYL ISOCYANATE
106. 4-BROMO-2-FLUOROPHENYL ISOCYANATE
107. 2-FLUORO-5-METHYLPHENYL ISOCYANATE
108. 2,3,4-TRIFLUOROPHENYL ISOCYANATE
109. 2-(DIFLUOROMETHOXY)PHENYL ISOCYANATE
110. 4-(DIFLUOROMETHOXY)PHENYL ISOCYANATE
111. 2-METHYLBENZYL ISOCYANATE
112. 2-CHLOROBENZYL ISOCYANATE
113. 4-FLUOROBENZYL ISOCYANATE
114. 4-METHOXYBENZYL ISOCYANATE
115. 2,6-DIFLUOROBENZOYL ISOCYANATE
116. 4-FLUOROBENZOYL ISOCYANATE
117. 2-FLUORO-3-(TRIFLUOROMETHYL)PHENYL ISOCYANATE
118. 2-FLUORO-5-(TRIFLUOROMETHYL)PHENYL ISOCYANATE
119. 2-FLUORO-6-(TRIFLUOROMETHYL)PHENYL ISOCYANATE
120. 4-FLUORO-2-(TRIFLUOROMETHYL)PHENYL ISOCYANATE
121. 2-(TERT-BUTYL)PHENYL ISOCYANATE
122. 3-PYRIDYL ISOCYANATE

TABLE IV

Sulphonyl chloride derivatives of formula (X)

1. 1-NAPHTHALENESULFONYL CHLORIDE
2. 2-NAPHTHALENESULFONYL CHLORIDE
3. 2-THIOPHENESULFONYL CHLORIDE
4. 8-QUINOLINESULFONYL CHLORIDE
5. BENZENESULFONYL CHLORIDE
6. 2,4,5-TRICHLOROBENZENESULFONYL CHLORIDE
7. 2,5-DICHLOROBENZENESULFONYL CHLORIDE
8. 3,5-DICHLORO-2-HYDROXYBENZENESULFONYL CHLORIDE
9. 2-MESITYLENESULFONYL CHLORIDE
10. 4-BROMOBENZENESULFONYL CHLORIDE
11. 4-FLUOROBENZENESULFONYL CHLORIDE
12. 4-CHLOROBENZENESULFONYL CHLORIDE
13. PIPSYL CHLORIDE
14. 4-METHOXYBENZENESULFONYL CHLORIDE
15. 4-TERT-BUTYLBENZENESULFONYL CHLORIDE
16. P-TOLUENESULFONYL CHLORIDE
17. ISOPROPYLSULFONYL CHLORIDE
18. METHANESULFONYL CHLORIDE
19. ALPHA-TOLUENESULFONYL CHLORIDE
20. ETHANESULFONYL CHLORIDE
21. 1-PROPANESULFONYL CHLORIDE
22. 1-BUTANESULFONYL CHLORIDE
23. PENTAMETHYLBENZENESULFONYL CHLORIDE
24. 2,3,5,6-TETRAMETHYLBENZENESULFONYL CHLORIDE
25. 3-(TRIFLUOROMETHYL)BENZENESULPHONYL CHLORIDE
26. 3,5-BIS(TRIFLUOROMETHYL)BENZENESULFONYL CHLORIDE
27. 2,3,4-TRICHLOROBENZENESULFONYL CHLORIDE
28. 2,5-DIMETHOXYBENZENESULFONYL CHLORIDE
29. 4-METHOXY-2,3,6-TRIMETHYLBENZENESULFONYL CHLORIDE
30. 3,4-DICHLOROBENZENESULFONYL CHLORIDE
31. 4,5-DIBROMOTHIOPHENE-2-SULFONYL CHLORIDE
32. 3-CHLORO-4-FLUOROBENZENESULPHONYL CHLORIDE
33. 4-ETHYLBENZENESULFONYL CHLORIDE
34. 4-N-PROPYLBENZENESULFONYL CHLORIDE
35. 4-N-AMYLBENZENESULFONYL CHLORIDE
36. 4-ISOPROPYLBENZENESULPHONYL CHLORIDE
37. 4-BROMO-2,5-DIFLUOROBENZENESULFONYL CHLORIDE
38. 2-FLUOROBENZENESULPHONYL CHLORIDE
39. 3-FLUOROBENZENESULPHONYL CHLORIDE
40. 4-(TRIFLUOROMETHOXY)BENZENESULPHONYL CHLORIDE
41. 4-(TRIFLUOROMETHYL)BENZENESULFONYL CHLORIDE
42. 2,4-DIFLUOROBENZENESULPHONYL CHLORIDE
43. 2,4-DICHLORO-5-METHYLBENZENESULFONYL CHLORIDE
44. 4-CHLORO-2,5-DIMETHYLBENZENESULPHONYL CHLORIDE
45. 2-CHLOROBENZENESULFONYL CHLORIDE
46. 4-BROMO-2,5-DICHLOROTHIOPHENE-3-SULFONYL CHLORIDE
47. 2,5-DICHLOROTHIOPHENE-3-SULPHONYL CHLORIDE
48. 5-CHLOROTHIOPHENE-2-SULFONYL CHLORIDE
49. 2-(TRIFLUOROMETHYL)BENZENESULFONYL CHLORIDE
50. 3-CHLOROBENZENESULFONYL CHLORIDE
51. 3,5-DICHLOROBENZENESULFONYL CHLORIDE
52. M-TOLUENESULFONYL CHLORIDE
53. 2-CHLORO-6-METHYLBENZENESULFONYL CHLORIDE
54. 5-BROMO-2-METHOXYBENZENESULFONYL CHLORIDE
55. 3,4-DIMETHOXYBENZENESULFONYL CHLORIDE
56. 2,3-DICHLOROBENZENESULFONYL CHLORIDE
57. 2-BROMOBENZENESULFONYL CHLORIDE
58. 2,3-DICHLOROTHIOPHENE-5-SULPHONYL CHLORIDE
59. 4-PHENYLTHIOPHENE-2,4-DISULFONYL
60. 5-PHENYLTHIOPHENE-2,5-DISULFONYL CHLORIDE
61. 3-CHLORO-2-METHYLBENZENESULFONYL CHLORIDE
62. 2-CHLORO-5-(TRIFLUOROMETHYL)BENZENESULFONYL CHLORIDE
63. 2,6-DICHLOROBENZENESULFONYL CHLORIDE
64. 3-BROMOBENZENESULFONYL CHLORIDE
65. 2-(TRIFLUOROMETHOXY)BENZENESULFONYL CHLORIDE
66. 4-CYANOBENZENESULFONYL CHLORIDE
67. 2-CYANOBENZENESULFONYL CHLORIDE
68. 4-(N-BUTOXY)BENZENESULFONYL CHLORIDE

TABLE IV-continued

Sulphonyl chloride derivatives of formula (X)

69. 4-ACETAMIDO-3-CHLOROBENZENESULFONYL CHLORIDE
70. 3,5-DIMETHYLISOXAZOLE-4-SULFONYL CHLORIDE
71. 2,4-DICHLOROBENZENESULFONYL CHLORIDE
72. 2-CHLORO-4-FLUOROBENZENESULPHONYL CHLORIDE
73. 5-FLUORO-2-METHYLBENZENESULPHONYL CHLORIDE
74. 5-CHLORO-2-METHOXYBENZENESULFONYL CHLORIDE
75. 2,4,6-TRICHLOROBENZENESULFONYL CHLORIDE
76. 4-BIPHENYLSULFONYL CHLORIDE
77. 5-BROMOTHIOPHENE-2-SULFONYL CHLORIDE
78. 2,6-DIFLUOROBENZENESULFONYL CHLORIDE
79. 4-N-BUTYLBENZENESULFONYL CHLORIDE
80. 4-METHYLSULFONYLBENZENESULFONYL CHLORIDE
81. 2-METHYLSULFONYLBENZENESULFONYL CHLORIDE
82. 4-ACETYLBENZENESULFONYL CHLORIDE
83. 3-METHOXYBENZENESULPHONYL CHLORIDE
84. 2-METHOXY-4-METHYLBENZENESULPHONYL CHLORIDE

Pharmacology

The compounds of formula (I) are active as protein kinase inhibitors and are therefore useful, for instance, to restrict the unregulated proliferation of tumor cells.

In therapy, they may be used in the treatment of various tumors such as, for instance, carcinomas, e.g. mammary carcinoma, lung carcinoma, bladder carcinoma, colon carcinoma, ovary and endometrial tumors, sarcomas, e.g. soft tissue and bone sarcomas, and the hematological malignancies such as, e.g., leukemias.

In addition, the compounds of formula (I) are also useful in the treatment of other cell proliferative disorders such as psoriasis, vascular smooth cell proliferation associated with atherosclerosis and post-surgical stenosis and restenosis and in the treatment of Alzheimer's disease.

The inhibiting activity of putative protein kinase inhibitors and the potency of selected compounds was determined through a method of assay based on the use of the Multi-Screen-PH 96 well plate (Millipore), in which a phosphocellulose filter paper was placed at each well bottom allowing binding of positive charged substrate after a washing/filtration step.

When a radioactivity labeled phosphate moiety was transferred by the ser/threo kinase to the filter-bound histone, light emitted was measured in a scintillation counter.

Inhibition Assay of cdk2/Cyclin A Activity

Kinase reaction: 1.5 µM histone H1 substrate, 25 µM ATP (0.2 µCi $P^{33}\gamma$-ATP), 30 ng of baculovirus co-expressed cdk2/Cyclin A, 10 µM inhibitor in a final volume of 100 µl buffer (TRIS HCl 10 mM pH 7.5, MgCl$_2$ 10 µmM, 7.5 mM DTT) were added to each well of a 96 U bottom well plate. After 10 min at 37 ° C. incubation, reaction was stopped by 20 µl EDTA 120 mM.

Capture: 100 µl were transferred from each well to MultiScreen plate, to allow substrate binding to phosphocellulose filter. Plates were then washed 3 times with 150 µl/well PBS Ca++/Mg++ free and filtered by MultiScreen filtration system.

Detection: filters were allowed to dry at 37° C., then 100 µl/well scintillant were added and 33P labeled histone H1 was detected by radioactivity counting in the Top-Count instrument.

Results: data were analyzed and expressed as % inhibition referred to total activity of enzyme (=100%).

All compounds showing inhibition ≧50% were further analyzed in order to study and define potency (IC50) as well as the kinetic-profile of inhibitor through Ki calculation.

IC50 determination: the protocol used was the same described above, where inhibitors were tested at different concentrations ranging from 0.0045 to 10 µM. Experimental data were analyzed by the computer program GraphPad Prizm using the four parameter logistic equation:

$$y=\text{bottom}+(\text{top}-\text{bottom})/(1+10^{((\log IC50-x)*\text{slope})})$$

where x is the logarithm of the inhibitor concentration, y is the response; y starts at bottom and goes to top with a sigmoid shape.

Ki calculation: either the concentration of ATP and histone H1 substrate were varied: 4, 8, 12, 24, 48 µM for ATP (containing proportionally diluted $P^{33}\gamma$-ATP) and 0.4, 0.8, 1.2, 2.4, 4.8 µM for histone were used in absence and presence of two different, properly chosen inhibitor concentrations.

Experimental data were analyzed by the computer program "SigmaPlot" for Ki determination, using a random bireactant system equation:

$$v = \frac{v_{\max}\frac{(A)(B)}{aKAKB}}{1+\frac{(A)}{KA}+\frac{(B)}{KB}+\frac{(A)(B)}{aKAKB}}$$

where A=ATP and B=Histone H1.

In addition the selected compounds have been characterized on a panel of ser/threo kinases strictly related to cell cycle (cdk2/cyclin E, cdk1/cyclin B1, cdk4/Cyclin D1), and also for specificity on MAPK, PKA, EGFR, IGF1-R, Cdc7/dbf4 and aurora-2.

Inhibition Assay of cdk2/Cyclin E Activity

Kinase reaction: 1.5 µM histone H1 (Sigma # H-5505) substrate, 25 µM ATP (0.2 uCi $P^{33}\gamma$-ATP), 15 ng of baculovirus co-expressed cdk2/GST-Cyclin E, suitable concentrations of inhibitor in a final volume of 100 µl buffer (TRIS HCl 10 mM pH 7.5, MgCl$_2$ 10 mM, 7.5 mM DTT+0.2 mg/ml BSA) were added to each well of a 96 U bottom well plate. After 10 min at 37 ° C. incubation, reaction was stopped by 20 µl EDTA 120 mM.

Capture: 100 µl were transferred from each well to MultiScreen plate, to allow substrate binding to phosphocellulose filter. Plates were then washed 3 times with 150 µl/well PBS Ca++/Mg++ free and filtered by MultiScreen filtration system.

Detection: filters were allowed to dry at 37° C., then 100 µl/well scintillant were added and $^{33}P$ labeled histone H1 was detected by radioactivity counting in the Top-Count instrument.

Inhibition Assay of cdk1/Cyclin B1 Activity

Kinase reaction: 1.5 µM histone H1 (Sigma # H-5505) substrate, 25 µM ATP (0.2 µCi $P^{33}\gamma$-ATP), 30 ng of baculovirus co-expressed cdk1/Cyclin B1, suitable concentrations of inhibitor in a final volume of 100 µl buffer (TRIS HCl 10 mM pH 7.5, MgCl$_2$ 10 mM, 7.5 mM DTT+0.2 mg/ml BSA) were added to each well of a 96 U bottom well plate. After 10 min at 37 ° C. incubation, reaction was stopped by 20 µl EDTA 120 mM.

Capture: 100 µl were transferred from each well to MultiScreen plate, to allow substrate binding to phosphocellulose filter. Plates were then washed 3 times with 150 µl/well PBS Ca++/Mg++ free and filtered by MultiScreen filtration system.

Detection: filters were allowed to dry at 37° C., then 100 µl/well scintillant were added and $^{33}$P labeled histone H1 was detected by radioactivity counting in the Top-Count instrument.

Inhibition Assay cdk4/Cyclin D1 Activity

Kinase reaction: 0,4 uM µM mouse GST-Rb(769–921) (# sc-4112 from Santa Cruz) substrate, 10 µM ATP (0.5 µCi P$^{33}$γ-ATP), 100 ng of baculovirus expressed GST-cdk4/GST-Cyclin D1, suitable concentrations of inhibitor in a final volume of 50 µl buffer (TRIS HCl 10 mM pH 7.5, MgCl$_2$ 10 mM, 7.5 mM DTT+0.2 mg/ml BSA) were added to each well of a 96 U bottom well plate. After 40 min at 37 ° C. incubation, reaction was stopped by 20 µl EDTA 120 mM.

Capture: 60 µl were transferred from each well to MultiScreen plate, to allow substrate binding to phosphocellulose filter. Plates were then washed 3 times with 150 µl/well PBS Ca$^{++}$/Mg$^{++}$ free and filtered by MultiScreen filtration system.

Detection: filters were allowed to dry at 37° C., then 100 µl/well scintillant were added and $^{33}$P labeled Rb fragment was detected by radioactivity counting in the Top-Count instrument.

Inhibition Assay of MAPK Activity

Kinase reaction: 10 µM MBP (Sigma # M-1891) substrate, 25 µM ATP (0.2 µCi p$^{33}$γ-ATP), 25 ng of bacterially expressed GST-MAPK (Upstate Biotechnology # 14-173), suitable concentrations of inhibitor in a final volume of 100 µl buffer (TRIS HCl 10 mM pH 7.5, MgCl$_2$ 10 mM, 7.5 mM DTT+0.1 mg/ml BSA) were added to each well of a 96 U bottom well plate. After 15 min at 37 ° C. incubation, reaction was stopped by 20 µl EDTA 120 mM.

Capture: 100 µl were transferred from each well to MultiScreen plate, to allow substrate binding to phosphocellulose filter. Plates were then washed 3 times with 150 µl/well PBS Ca$^{++}$/Mg$^{++}$ free and filtered by MultiScreen filtration system.

Detection: filters were allowed to dry at 37° C., then 100 µl/well scintillant were added and $^{33}$P labeled MBP was detected by radioactivity counting in the Top-Count instrument.

Inhibition Assay of PKA Activity

Kinase reaction: 10 µM histone H1 (Sigma # H-5505) substrate, 10 µM ATP (0.2 µCi P$^{33}$γ-ATP), 1 U of bovine heart PKA (Sigma # 2645), suitable concentrations of inhibitor in a final volume of 100 µl buffer (TRIS HCl 10 mM pH 7.5, MgCl$_2$ 10 mM, 7.5 mM DTT+0.2 mg/ml BSA) were added to each well of a 96 U bottom well plate. After 5 min at 37° C. incubation, reaction was stopped by 20 µl EDTA 120 mM.

Capture: 100 µl were transferred from each well to MultiScreen plate, to allow substrate binding to phosphocellulose filter. Plates were then washed 3 times with 150 µl/well PBS Ca$^{++}$/Mg$^{++}$ free and filtered by MultiScreen filtration system.

Detection: filters were allowed to dry at 37° C, then 100 µl/well scintillant were added and $^{33}$P labeled histone H1 was detected by radioactivity counting in the Top-Count instrument.

Inhibition Assay of EGFR Activity

Kinase reaction: 25 nM in house biotinylated PolyGluTyr (Sigma # 0275) substrate, 2,5 µM ATP (0.3 µCi P$^{33}$γ-ATP), 80 ng baculovirus expressed GST-EGFR, suitable concentrations of inhibitor in a final volume of 100 µl buffer (Hepes 50 mM pH 7,5, MnCl$_2$—MgCl$_2$ 3mM, 1 mM DTT+3 µM NaVO3, 0.1 mg/ml BSA) were added to each well of a 96 U bottom well plate. After 5 min. at 37° C. incubation, reaction was stopped by 20 µl EDTA 120 mM.

Capture: 100 µl were transferred from each well to streptavidin-Flashplate, to allow biotinylated-substrate binding to plate. Plates were then washed 3 times with 150 µl/well PBS Ca$^{++}$/Mg$^{++}$ free.

Detection: radioactivity counting in the Top-Count instrument.

Inhibition Assay of IGF1-R Activity

The inhibition assay of IGF1-R activity was performed according to the following protocol.

Kinase reaction: 10 µM biotinylated MBP (Sigma cat. # M-1891) substrate, 0–20 µM inhibitor, 6 µM cold ATP, 2 nM $^{33}$P-ATP, and 22.5 ng IGF1-R (pre-incubated for 30 min at room temperature with cold 60 µM cold ATP) in a final volume of 30 µl buffer (50 mM HEPES pH 7.9, 3 mM MnCl$_2$, 1 mM DTT, 3 µM NaVO$_3$) were added to each well of a 96 U bottom well plate. After incubation for 35 min at room temperature, the reaction was stopped by addition of 100 µl PBS buffer containing 32 mM EDTA, 500 µM cold ATP, 0.1% Triton X100 and 10 mg/ml-streptavidin coated SPA beads. After 15 min incubation, 110 µL of suspension were withdrawn and transferred into 96-well OPTIPLATEs containing 100 µl of 5M CsCl. After 4 hours, the plates were read for 2 min in a Packard TOP-Count radioactivity reader.

Results: Experimental data were analyzed with the program GraphPad Prizm.

In addition, the inhibiting activity of putative protein kinase inhibitors and the potency of selected compounds was also determined through a method of assay based on the use of a SPA (Scintillation Proximity Assay) 96 well plate assay. The assay is based on the ability of streptavidin coated SPA beads to capture a biotinylated peptide derived from a phosphorylation site of histone.

When a radioactivity labeled phosphate moiety was transferred by the ser/threo kinase to the biotinylated histone peptide, light emitted was measured in a scintillation counter.

Inhibition Assay of cdk5/p25 Activity

The inhibition assay of cdk5/p25 activity was performed according to the following protocol.

Kinase reaction: 1.0 µM biotinylated histone peptide substrate, 0.25 µCi P$^{33}$γ-ATP, 4 nM cdk5/p25 complex, 0–100 µM inhibitor in a final volume of 100 µl buffer (Hepes 20 mM pH 7.5, MgCl2 15 mM, 1 mM DTT) were added to each well of a 96 U bottom well plate. After 20 min at 37° C. incubation, the reaction was stopped by the addition of 500 ug SPA beads in phosphate-buffered saline containing 0.1% Triton X-100, 50 µM ATP and 5 mM EDTA. The beads were allowed to settle, and the radioactivity incorporated in the $^{33}$P-labelled peptide was detected in a Top Count scintillation counter.

Results: Data were analyzed and expressed as % Inhibition using the formula:

100X(1−(Unknown−Bkgd)/(Enz. Control−Bkgd))

IC50 values were calculated using a variation of the four parameter logistics equation:

$Y=100/[1+10\hat{}((Log\ EC50-X)*Slope)]$

Where X=log(µM) and Y=% Inhibition.

Inhibition Assay of Cdc7/dbf4 Activity

The inhibition assay of Cdc7/dbf4 activity was performed according to the following protocol.

The Biotin-MCM2 substrate is trans-phosphorylated by the Cdc7/Dbf4 complex in the presence of ATP traced with γ$^{33}$-ATP. The phosphorylated Biotin-MCM2 substrate is then captured by Streptavidin-coated SPA beads and the extent of phosphorylation evaluated by β counting.

The inhibition assay of Cdc7/dbf4 activity was performed in 96 wells plate according to the following protocol.

To each well of the plate were added:
- 10 μl substrate (biotinylated MCM2, 6 nM final concentration)
- 10 μl enzyme (Cdc7/Dbf4, 12.5 nM final concentration)
- 10 μl test compound (12 increasing concentrations in the nM to μM range to generate a dose-response curve)
- 10 μl of a mixture of cold ATP (10 μM final concentration) and radioactive ATP (1/2500 molar ratio with cold ATP) was then used to start the reaction which was allowed to take place at 37° C.

Substrate, enzyme and ATP were diluted in 50 mM HEPES pH 7.9 containing 15 mM $MgCl_2$, 2 mM DTT, 3 μM $NaVO_3$, 2 mM glycerophosphate and 0.2 mg/ml BSA. The solvent for test compounds also contained 10% DMSO.

After incubation for 20 minutes, the reaction was stopped by adding to each well 100 μl of PBS pH 7.4 containing 50 mM EDTA, 1 mM cold ATP, 0.1% Triton X100 and 10 mg/ml streptavidin coated SPA beads.

After 15 minutes of incubation at room temperature to allow the biotinylated MCM2-streptavidin SPA beads interaction to occur, beads were trapped in a 96 wells filter plate (Unifilter$^R$ GF/B™) using a Packard Cell Harvester (Filtermate), washed with distilled water and then counted using a Top Count (Packard).

Counts were blank-subtracted and then the experimental data (each point in triplicate) were analyzed for IC50 determination using a non-linear regression analysis (Sigma Plot).

Inhibition Assay of Aurora-2 Activity

The inhibiting activity and the potency of selected compounds was determined through a method of assay based on the use of the streptavidin scintillation proximity assay beads (amershampharmacia biotech) run in a 96 well plates. At the end of the reaction, the biotinylated peptide substrate was captured with the beads and subsequently allowed to stratify using $CsCl_2$.

When a radioactivity labeled phosphate moiety was transferred by the kinase to the beads-bound peptide, light emitted was measured in a scintillation counter.

The inhibition assay of Aurora-2 activity was performed in 96 wells plate according to the following protocol.

Kinase reaction: 8 μM biotinylated peptide (4 repeats of LRRWSLG), 10 μM ATP (0.5 μCi $P^{33}γ$-ATP), 10 nM Aurora2, 10 μM inhibitor in a final volume of 60 μl buffer (HEPES 50 mM pH 7.0, $MgCl_2$ 10 mM, 1 mM DTT, 0.125 mg/ml BSA, 3 μM orthovanadate) were added to each well of a 96 U bottom well plate. After 30 minutes at room temperature incubation, reaction was stopped and biotinylated peptide captured by adding 100 μl of bead suspension.

Stratification: 100 μl of CsCl2 7.5 M were added to each well and let stand one hour before radioactivity was counted in the Top-Count instrument.

Results: data were analyzed and expressed as % inhibition referred to total activity of enzyme (=100%).

All compounds showing inhibition ≧60% were further analyzed in order to study the potency of the inhibitor through IC50 calculation.

The protocol used was the same described above, except that serial dilution of the inhibitor was used. Experimental data were fitted by nonlinear regression using the following equation:

$$v = v_0 + \frac{(v_0 - v_b)}{1 + 10^{n(\log IC_{50} - \log[I])}}$$

With $v_b$ as the baseline velocity, v as the observed reaction velocity, $v_o$ as the velocity in the absence of inhibitors, and [I] as the inhibitor concentration.

The compounds of formula (I) of the present invention, suitable for administration to a mammal, e.g. to humans, can be administered by the usual routes and the dosage level depends upon the age, weight, conditions of the patient and the administration route. For example, a suitable dosage adopted for oral administration of a compound of formula (I) may range from about 10 to about 500 mg pro dose, from 1 to 5 times daily.

The compounds of the invention can be administered in a variety of dosage forms, e.g. orally, in the form of tablets, capsules, sugar or film coated tablets, liquid solutions or suspensions; rectally in the form of suppositories; parenterally, e.g. intramuscularly, or by intravenous and/or intrathecal and/or intraspinal injection or infusion.

In addition, the compounds of the invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), metallomatrixprotease inhibitors, telomerase inhibitors, tyrosine kinase inhibitors, anti-growth factor receptor agents, anti-HER agents, anti-EGFR agents, anti-angiogenesis agents, farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

As an example, the compounds of the invention can be administered in combination with one or more chemotherapeutic agents such as, for instance, exemestane, formestane, anastrozole, letrozole, fadrozole, taxane, taxane derivatives, encapsulated taxanes, CPT-11, camptothecin derivatives, anthracycline glycosides, e.g., doxorubicin, idarubicin, epirubicin, etoposide, navelbine, vinblastine, carboplatin, cisplatin, estramustine phosphate, celecoxib, tamoxifen, raloxifen, Sugen SU-5416, Sugen SU-6668, Herceptin, and the like, optionally within liposomal formulations thereof.

If formulated as a fixed dose, such combination products employ the compounds of this invention within the dosage range described above and the other pharmaceutically active agent within the approved dosage range.

Compounds of formula (I) may be used sequentially with known anticancer agents when a combination formulation is inappropriate.

The present invention also includes pharmaceutical compositions comprising a compound of formula (I) or a pharmaceutically acceptable salt thereof in association with a pharmaceutically acceptable excipient (which can be a carrier or a diluent).

The pharmaceutical compositions containing the compounds of the invention are usually prepared following conventional methods and are administered in a pharmaceutically suitable form.

For example, the solid oral forms may contain, together with the active compound, diluents, e.g. lactose, dextrose, saccharose, sucrose, cellulose, corn starch or potato starch;

lubricants, e.g. silica, talc, stearic, magnesium or calcium stearate, and/or polyethylene glycols; binding agents, e.g. starches, arabic gum, gelatin, methylcellulose, carboxymethylcellulose or polyvinyl pyrrolidone; disaggregating agents, e.g. a starch, alginic, alginates or sodium starch glycolate; effervescing mixtures; dyestuffs; sweeteners; wetting agents such as lecithin, polysorbates, laurylsulfates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerin and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusions may contain as carrier, for example, sterile water or preferably they may be in the form of sterile, aqueous, isotonic saline solutions or they may contain as a carrier propylene glycol.

The suppositories may contain together with the active compound a pharmaceutically acceptable carrier, e.g. cocoa butter, polyethylene glycol, a polyoxyethylene sorbitan fatty ester surfactant or lecithin.

The following examples are herewith intended to better illustrate the present invention without posing any limitation to it.

EXAMPLES

The following examples are herewith intended to better illustrate the present invention without posing any limitation to it.

Example 1

Ethyl 3-(3-nitrophenyl)-1-tritylpolystyrene-1H-pyrazole-4-carboxylate

Diisopropylethylamine (3.26 ml, 19.5 mmol) and a solution of ethyl 3-(3-nitrophenyl)-pyrazole-4-carboxylate (2.5 g, 9.5 mmol) in dimethylformamide DMF (12 ml) were added to a slurry of Trityl chloride resin (5 g, 1.27 mmol/g loading, 6.35 mmol, 1 eq.) in dichlorometane (35 ml). The mixture was gently stirred at r.t. for 16 h and then filtered under reduced pressure. The resin was suspended in a mixture of dichlorometane/methanol/diethylamine 85:10:5 (100 ml), stirred for 20 minutes and filtered. After washing consecutively with dichlorometane (DCM), methanol and diethyl ether, it was dried overnight in oven at 35° C. under reduced pressure to give 6 g of resin.

By working in an analogous way and by using 3-(4-nitrophenyl)-pyrazole-4-carboxylate, it was obtained ethyl 3-(4-nitrophenyl)-1-tritylpolystyrene-1H-pyrazole-4-carboxylate.

Example 2

3-(3-nitrophenyl)-1-tritylpolystyrene-1H-pyrazole-4-carboxylic acid

To a suspension of ethyl 3-(3-nitrophenyl)-1-tritylpolystyrene-1H-pyrazole-4-carboxylate (6.4 g, 1 mmol/g loading) in 77 ml of methanol sodium hydroxide 35% (6.4 ml, 12 eq.) was added. The mixture was stirred at 70° C. for 16 h. After cooling, the slurry was filtered under reduced pressure and washed abundantly with methanol to dissolve the sodium hydroxide precipitated during the reaction. The treatment was repeated three times more. The resin was afterwards washed with methanol, DCM, diethyl ether and dried at 35° C. under vacuum, to give 6 g of 3-(3-nitrophenyl)-1-tritylpolystyrene-1H-pyrazole-4-carboxylic acid.

By working in an analogous way and by using ethyl 3-(4nitrophenyl)-1-tritylpolystyrene-1H-pyrazole-4-carboxylate, 3-(4-nitrophenyl)-1-tritylpolystyrene-1H-pyrazole-4-carboxylic acid was thus obtained.

Example 3

N-(2-hydroxyphenyl)-3-(3-nitrophenyl)-1-tritylpolystyrene-1H-pyrazole-4-carboxamide A solution of N-hydroxybenzotriazole (1.35 g, 1 mmol) and o-benzotriazol-1-yl-n,n,n',n'-tetramethyluronium tetrafluoroborate (3.2 g, 1 mmol) in 15 ml of dry dimethylformamide was added to a slurry of 3-(3-nitrophenyl)-1-tritylpolystyrene-1H-pyrazole-4-carboxylic acid (2 g, 2 mmol) in 5 ml of dry DMF. The mixture was stirred for 30 minutes then o-aminophenol was added and the final suspension was stirred at r.t. for 20 h. The slurry was filtered under reduced pressure, the resin washed abundantly with DMF, DCM, MeOH and diethyl ether and dried at 35° C. under vacuum.

By working in an analogous way and by using the appropriate aniline derivative, the following compounds were prepared:

N-(3-hydroxynaphtalen-2-yl)-3-(3-nitrophenyl) 1-tritylpolystyrene-1H-pyrazole-4-carboxamide;
N-(3-hydroxypyrid-2-yl)-3-(3-nitrophenyl)-1-tritylpolystyrene-1H-pyrazole-4-carboxamide;
N-[(2-hydroxy4-methyl)phenyl]-3-(3-nitrophenyl)-1-tritylpolystyrene-1H-pyrazole-4-carboxamide;
N-[(2-hydroxy-5-chloro)phenyl]-3-(3-nitrophenyl)-1-tritylpolystyrene-1H-pyrazole-4-carboxamide;
N-(2-hydroxy-5-tbutylphenyl)-3-(3-nitrophenyl)-1-tritylpolystyrene-1H-pyrazole-4-carboxamide;
N-[(2-hydroxy-5-methyl)phenyl]-3-(3-nitrophenyl)-1-tritylpolystyrene-1H-pyrazole-4-carboxamide;
N-(2-hydroxynaphtalen-1-yl)-3-(3-nitrophenyl)-1-tritylpolystyrene-1H-pyrazole-4-carboxamide;
N-[(2-hydroxy-3,5-chloro4-methyl)phenyl]-3-(3-nitrophenyl)-1-tritylpolystyrene-1H-pyrazole-4-carboxamide;
N-[(2-hydroxy-5-ethylsulfonyl)phenyl]-3-(3-nitrophenyl)-1-tritylpolystyrene-1H-pyrazole-4-carboxamide;
N-[(2-hydroxy-5-phenyl)phenyl]-3-(3-nitrophenyl)-1-tritylpolystyrene-1H-pyrazole-4-carboxamide;
N-[(2-hydroxy-3-isopropyl-6-methyl)phenyl]-3-(3-nitrophenyl)-1-tritylpolystyrene-1H-pyrazole-4-carboxamide;
N-[(2-hydroxy-6-methyl)phenyl]-3-(3-nitrophenyl)-1-tritylpolystyrene-1H-pyrazole-4-carboxamide;
N-(3-hydroxynaphtalen-2-yl)-3-(4nitrophenyl)-1-tritylpolystyrene-1H-pyrazole-4-carboxamide;
N-(3-hydroxypyrid-2-yl)-3-(4-nitrophenyl)-1-tritylpolystyrene-1H-pyrazole-4-carboxamide;

N-(2-hydroxyphenyl)-3-(4-nitrophenyl)-1-tritylpolystyrene-1H-pyrazole-4-carboxamide;
N-[(2-hydroxy-4-methyl)phenyl]-3-(4-nitrophenyl)-1-tritylpolystyrene-1H-pyrazole-4-carboxamide;
N-[(2-hydroxy-5-chloro)phenyl]-3-(4-nitrophenyl)-1-tritylpolystyrene-1H-pyrazole-4-carboxamide;
N-(2-hydroxy-5-tbutylphenyl)-3-(4-nitrophenyl)-1-tritylpolystyrene-1H-pyrazole-4-carboxamide;
N-[(2-hydroxy-5-methyl)phenyl]-3-(4-nitrophenyl)-1-tritylpolystyrene-1H-pyrazole-4-carboxamide;
N-(2-hydroxynaphtalen-1-yl)-3-(4-nitrophenyl)-1-tritylpolystyrene-1H-pyrazole-4-carboxamide;
N-[(2-hydroxy-3,5-chloro-4-methyl)phenyl]-3-(4-nitrophenyl)-1-tritylpolystyrene-1H-pyrazole-4-carboxamide;
N-[(2-hydroxy-5-ethylsulfonyl)phenyl]-3-(4-nitrophenyl)-1-tritylpolystyrene-1H-pyrazole-4-carboxamide;
N-[(2-hydroxy-5-phenyl)phenyl]-3-(4-nitrophenyl)-1-tritylpolystyrene-1H-pyrazole-4-carboxamide;
N-[(2-hydroxy-3-isopropyl-6-methyl)phenyl]-3-(4-nitrophenyl)-1-tritylpolystyrene-1H-pyrazole-4-carboxamide;
N-[(2-hydroxy-6-methyl)phenyl]-3-(4-nitrophenyl)-1-tritylpolystyrene-1H-pyrazole-4-carboxamide.

Example 4

2-[3-(3-nitrophenyl-1-tritylpolystyrene-1H-pyrazol-4-yl]-1,3-benzoxazole

Tributylphosphine (2.5 ml, 10 mmol) followed by diethyl azodicarboxylate (1.6 ml, 10 mmol) were added dropwise to a slurry of N-(2-hydroxyphenyl)-3-(3-nitrophenyl)-1-tritylpolystyrene-1H-pyrazole-4-carboxamide (2.1 g, 2 mmol, 1 eq) in 20 ml of dry tetrahydrofuran. The brown suspension was stirred at r.t. for 16 h. After filtering under reduced pressure, the resin was washed with dimethylformamide (3×), DCM (3×), methanol (3×) and diethyl ether (3×) and dried at 35° C. under vacuum.

By working in an analogous way and by starting from the appropriate derivative prepared as described in example 3, the following compounds were prepared:
2-[3-(3-nitrophenyl)-1-tritylpolystyrene-1H-pyrazol-4-yl]-1,3-naphth[2,3-d]oxazole;
2-[3-(3-nitrophenyl)-1-tritylpolystyrene-1H-pyrazol-4-yl]-1,3-oxazolo[4,5-b]pyridine;
2-[3-(3-nitrophenyl)-1-tritylpolystyrene-1H-pyrazol-4-yl]-6-methyl-1,3-benzoxazole;
2-[3-(3-nitrophenyl)-1-tritylpolystyrene-1H-pyrazol-4-yl]-5-chloro-1,3-benzoxazole;
2-[3-(3-nitrophenyl)-1-tritylpolystyrene-1H-pyrazol-4-yl]-5-tbutyl-1,3-benzoxazole;
2-[3-(3-nitrophenyl)-1-tritylpolystyrene-1H-pyrazol-4-yl]-5-methyl-1,3-benzoxazole;
2-[3-(3-nitrophenyl)-1-tritylpolystyrene-1H-pyrazol-4-yl]-1,3-naphth[1,2-d]oxazole;
2-[3-(3-nitrophenyl)-1-tritylpolystyrene-1H-pyrazol-4-yl]-5,7-chloro-6-methyl-1,3-benzoxazole;
2-[3-(3-nitrophenyl)-1-tritylpolystyrene-1H-pyrazol-4-yl]-5-ethylsulfonyl-1,3-benzoxazole;
2-[3-(3-nitrophenyl)-1-tritylpolystyrene-1H-pyrazol-4-yl]-5-phenyl-1,3-benzoxazole;
2-[3-(3-nitrophenyl)-1-tritylpolystyrene-1H-pyrazol-4-yl]-4-methyl-7-isopropyl-1,3-benzoxazole;
2-[3-(3-nitrophenyl)-1-tritylpolystyrene-1H-pyrazol-4-yl]-4-methyl-1,3-benzoxazole;
2-[3-(4-nitrophenyl)-1-tritylpolystyrene-1H-pyrazol-4-yl]-1,3-benzoxazole;
2-[3-(4-nitrophenyl)-1-tritylpolystyrene-1H-pyrazol-4-yl]-1,3-naphth[2,3-d]oxazole;
2-[3-(4-nitrophenyl)-1-tritylpolystyrene-1H-pyrazol-4-yl]-1,3-oxazolo[4,5-b]pyridine;
2-[3-(4-nitrophenyl)-1-tritylpolystyrene-1H-pyrazol-4-yl]-6-methyl-1,3-benzoxazole;
2-[3-(4-nitrophenyl)-1-tritylpolystyrene-1H-pyrazol-4-yl]-5-chloro-1,3-benzoxazole;
2-[3-(4-nitrophenyl)-1-tritylpolystyrene-1H-pyrazol-4-yl]-5-tbutyl-1,3-benzoxazole;
2-[3-(4-nitrophenyl)-1-tritylpolystyrene-1H-pyrazol-4-yl]-5-methyl-1,3-benzoxazole;
2-[3-(4-nitrophenyl)-1-tritylpolystyrene-1H-pyrazol-4-yl]-1,3-naphth[1,2-d]oxazole;
2-[3-(4-nitrophenyl)-1-tritylpolystyrene-1H-pyrazol-4-yl]-5,7-chloro-6-methyl-1,3-benzoxazole;
2-[3-(4-nitrophenyl)-1-tritylpolystyrene-1H-pyrazol-4-yl]-5-ethylsulfonyl-1,3-benzoxazole;
2-[3-(4-nitrophenyl)-1-tritylpolystyrene-1H-pyrazol-4-yl]-5-phenyl-1,3-benzoxazole;
2-[3-(4-nitrophenyl)-1-tritylpolystyrene-1H-pyrazol-4-yl]-4-methyl-7-isopropyl-1,3-benzoxazole;
2-[3-(4-nitrophenyl)-1-tritylpolystyrene-1H-pyrazol-4-yl]-4-methyl-1,3-benzoxazole.

Example 5

2-[3-(3-aminophenyl)-1-tritylpolystyrene-1H-pyrazol-4-yl]-1,3-benzoxazole

A solution of tin (II) chloride monohydrated (6.6 g, 30 mmol) in dimethylformamide (10 ml) was added to a slurry of 2-[3-(3-nitrophenyl)-1-tritylpolystyrene-1H-pyrazol-4-yl]-1,3-benzoxazole (2 g, 2 mmol). The suspension was stirred at r.t. for 16 h. After filtering under reduced pressure the resin was washed with DMF (3×), DCM (3×), MeOH (3×) and diethyl ether (3×) and dried at 35° C. under vacuum, yielding 6.5 g of 2-[3-(3-aminophenyl)-1-tritylpolystyrene-1H-pyrazol-4-yl]-1,3-benzoxazole.

By working in an analogous way and by using the appropriate nitro derivatives from example 4, the following additional compounds were prepared:
2) 2-[3-(3-aminophenyl)-1-tritylpolystyrene-1H-pyrazol-4-yl]-1,3-naphth[2,3-d]oxazole;
3) 2-[3-(3-aminophenyl)-1-tritylpolystyrene-1H-pyrazol-4-yl]-1,3-oxazolo[4,5-b]pyridine;
4) 2-[3-(3-aminophenyl)-1-tritylpolystyrene-1H-pyrazol-4-yl]-6-methyl-1,3-benzoxazole;
5) 2-[3-(3-aminophenyl)-1-tritylpolystyrene-1H-pyrazol-4-yl]-5-chloro-1,3-benzoxazole;
6) 2-[3-(3-aminophenyl)-1-tritylpolystyrene-1H-pyrazol-4-yl]-5-tbutyl-1,3-benzoxazole;
7) 2-[3-(3-aminophenyl)-1-tritylpolystyrene-1H-pyrazol-4-yl]-5-methyl-1,3-benzoxazole;
8) 2-[3-(3-aminophenyl)-1-tritylpolystyrene-1H-pyrazol-4-yl]-1,3-naphth[1,2-d]oxazole;
9) 2-[3-(3-aminophenyl)-1-tritylpolystyrene-1H-pyrazol-4-yl]-5,7-chloro-6-methyl-1,3-benzoxazole;
10) 2-[3-(3-aminophenyl)-1-tritylpolystyrene-1H-pyrazol-4-yl]-5-ethylsulfonyl-1,3-benzoxazole;
11) 2-[3-(3-aminophenyl)-1-tritylpolystyrene-1H-pyrazol-4-yl]-5-phenyl-1,3-benzoxazole;
12) 2-[3-(3-aminophenyl)-1-tritylpolystyrene-1H-pyrazol-4-yl]-4-methyl-7-isopropyl-1,3-benzoxazole;
13) 2-[3-(3-aminophenyl)-1-tritylpolystyrene-1H-pyrazol-4-yl]-4-methyl-1,3-benzoxazole;

14) 2-[3-(4-aminophenyl)-1-tritylpolystyrene-1H-pyrazol-4-yl]-1,3-benzoxazole;
15) 2-[3-(4-aminophenyl)-1-tritylpolystyrene-1H-pyrazol-4-yl]-1,3-naphth[2,3-d]oxazole;
16) 2-[3-(4-aminophenyl)-1-tritylpolystyrene-1H-pyrazol-4-yl]-1,3-oxazolo[4,5-b]pyridine;
17) 2-[3-(4-aminophenyl)-1-tritylpolystyrene-1H-pyrazol-4-yl]-6-methyl-1,3-benzoxazole;
18) 2-[3-(4-aminophenyl)-1-tritylpolystyrene-1H-pyrazol-4-yl]-5-chloro-1,3-benzoxazole;
19) 2-[3-(4-aminophenyl)-1-tritylpolystyrene-1H-pyrazol-4-yl]-5-tbutyl-1,3-benzoxazole;
20) 2-[3-(4-aminophenyl)-1-tritylpolystyrene-1H-pyrazol-4-yl]-5-methyl-1,3-benzoxazole;
21) 2-[3-(4-aminophenyl)-1-tritylpolystyrene-1H-pyrazol-4-yl]-1,3-naphth[1,2-d]oxazole;
22) 2-[3-(4-aminophenyl)-1-tritylpolystyrene-1H-pyrazol-4-yl]-5,7-chloro-6-methyl-1,3-benzoxazole;
23) 2-[3-(4-aminophenyl)-1-tritylpolystyrene-1H-pyrazol-4-yl]-5-ethylsulfonyl-1,3-benzoxazole;
24) 2-[3-(4-aminophenyl)-1-tritylpolystyrene-1H-pyrazol-4-yl]-5-phenyl-1,3-benzoxazole;
25) 2-[3-(4-aminophenyl)-1-tritylpolystyrene-1H-pyrazol-4-yl]-4-methyl-7-isopropyl-1,3-benzoxazole;
26) 2-[3-(4-aminophenyl)-1-tritylpolystyrene-1H-pyrazol-4-yl]-4-methyl-1,3-benzoxazole.

Example 6

Preparation of N-{4-[4-(1,3-benzoxazol-2-yl)pyrazol-3-yl]phenyl}phenylacetamide

A solution of N-Methylmorpholine (55 µL, 0.05 mmoles), benzotriazol-1-yloxytris(pyrrolidino)phosphonium hexafluorophosphatecarbodiimide (260 mg, 0.05 mmol) and phenylacetic acid (68 mg, 0.05 mmoles) in 2 ml of dichloromethane (DCM) was stirred for 30' and then added to a suspension of 2-[3-(4-aminophenyl)-1-tritylpolystyrene-1H-pyrazol-4-yl]-1,3-benzoxazole from example 5 (100 mg, 0.01 mmol) in DCM (1 ml). The obtained suspension was stirred for 20 hrs at 22° C., filtered, washed with DCM (3×), methanol (3×) and diethyl ether (3×), and dried under nitrogen flux.

2 ml of a solution of TFA 10% in dichloromethane were then added to resin and the resulting red suspension was stirred for 1 h. Afterward the resin was filtered and washed twice with 1 ml of DCM. The filtered solution was evaporated under nitrogen flux to give 34 mg of a crude solid, that was purified by preparative LC-MS, using the following conditions:

| Eluent A: | aqueous solution of trifluoroacetic acid (0.01% v/v) | | |
|---|---|---|---|
| Eluent B: | acetonitrile | | |
| Gradient: | Time (m) | % A | 19 % B |
| | 0 (injection) | 90 | 10 |
| | 8 | 10 | 90 |
| | 10 (end) | 10 | 90 |
| Flow: | 20 ml/m | | |
| Column: | Waters Symmetry ™ C18 19 × 50 mm | | |
| Detector: | mass spectrometer, electrospray ionisation, positive mode. | | |

A liquid handler triggered by the mass spectrometer automatically collected the fractions containing the title compound. After evaporation of the solvent 10 mg of N-{4-[4-(1,3-benzoxazol-2-yl)pyrazol-3-yl]phenyl}phenylacetamide as a colorless solid were obtained. [M+H]+=394. $^1$H-NMR (DMSOd$_6$), diagnostic signals (ppm): 10.3 (s, 1H), 3.67 (s, 2H, CH$_3$).

Analogously, the following compounds were prepared by using the appropriate amino derivatives from example 5 and the appropriate carboxylic acid:

N-{4-[4-(5-methyl-1,3-benzoxazol-2-yl)pyrazol-3-yl]phenyl}phenylacetamide. [M+H]+=408. $^1$H-NMR (DMSOd$_6$), diagnostic signals (ppm): 3.67 (s,2H), 2.41 (s,3H).

N-{3-[4-(5-methyl-1,3-benzoxazol-2-yl)pyrazol-3-yl]phenyl}phenylacetamide. [M+H]+=408. $^1$H-NMR (DMSOd$_6$), diagnostic signals (ppm): 3.63 (s,2H), 2.41 (s,3H).

N-{4-[4-(5-methyl-1,3-benzoxazol-2-yl)pyrazol-3-yl]phenyl}-4-chlorophenylacetamide. [M+H]+=442. $^1$H-NMR (DMSOd$_6$), diagnostic signals (ppm): 7.48 (d, J=8 Hz, 1H), 7.4–7.3 (m,4H), 3.64 (s,2H).

N-{4-[4-(1,3-benzoxazol-2-yl)pyrazol-3-yl]phenyl}-4-chlorophenylacetamide. [M+H]+=428. $^1$H-NMR (DMSOd$_6$), diagnostic signals (ppm): 3.54 (s, 2H).

N-{4-[4-(5-methyl-1,3-benzoxazol-2-yl)pyrazol-3-yl]phenyl}-2-methyl-propionamide. [M+H]+=360. $^1$H-NMR (DMSOd6), diagnostic signals (ppm): 2.41 (s, 3H), 2.6 (m,1H), 1.12 (d, 6H).

N-[4-(5-methyl-1,3-benzoxazol-2-yl)-1H-pyrazol-3-yl]cyclopropanecarboxamide. [M+H]+=358. $^1$H-NMR (DMSOd6), diagnostic signals (ppm): 13.5 (s,1H), 10.3 (s,1H), 2.41 (s,3H), 1.8 (m,1H), 0.8 (m,4H).

N-[3-(1,3-benzoxazol-2-yl)-1H-pyrazol-3-yl]cyclopropanecarboxamide. [M+H]+=358. $^1$H-NMR (DMSOd6), diagnostic signals (ppm): 7.7–7.6 (m,2H), 7.4–7.3 (m,2H), 1.78 (m,1H).

N-[3-(5-methyl-1,3-benzoxazol-2-yl)-1H-pyrazol-3-yl]cyclopropanecarboxamide. [M+H]+=358. $^1$H-NMR (DMSOd6), diagnostic signals (ppm): 2.41 (s,3H), 1.8 (m,1H), 0.78 (m,4H).

N-{3-[4-(1,3-benzoxazol-2-yl)pyrazol-3-yl]phenyl)-benzamide. [M+H]+=394. $^1$H-NMR (DMSOd6), diagnostic signals (ppm): 2.41 (s,3H).

N-{3-[4-(5-methyl-1,3-benzoxazol-2-yl)pyrazol-3-yl]phenyl}-benzamide. [M+H]+=380. 1H-NMR (DMSOd6), diagnostic signals (ppm): 7.94 (d, J=8.5, 2H), 7.7–7.6 (m,2H), 7.4–7.3 (m, 2H).

N-{4-[4-(5-methyl-1,3-benzoxazol-2-yl)pyrazol-3-yl]phenyl}-benzamide. [M+H]+=394. 1H-NMR (DMSOd6), diagnostic signals (ppm): 2.41 (s,3H).

N-{3-[4-(1,3-benzoxazol-2-yl)pyrazol-3-yl]phenyl}-3-methoxybenzamide. [M+H]+=410. $^1$H-NMR (DMSOd6), diagnostic signals (ppm): 7.7 (m, 2H), 7.4–7.3 (m,2H), 3.82 (s, 3H).

N-{3-[4-(5-methyl-1,3-benzoxazol-2-yl)pyrazol-3-yl]phenyl}-3-methoxybenzamide. [M+H]+=424. $^1$H-NMR (DMSOd6), diagnostic signals (ppm): 3.82 (s,3H), 2.41 (s, 3H).

N-{4-[4-(1,3-benzoxazol-2-yl)pyrazol-3-yl]phenyl}-3-methoxybenzamide. [M+H]+=424. $^1$H-NMR (DMSOd6), diagnostic signals (ppm): 3.84 (s,3H), 2.42 (s,3H).

N-{3-[4-(1,3-benzoxazol-2-yl)pyrazol-3-yl]phenyl}-2-methyl-propionamide [M+H]+=346.

N-(3-[4-(5-methyl-1,3-benzoxazol-2-yl)pyrazol-3-yl]phenyl}phenylacetamide. [M+H]+=394.

N-{3-[4-(5-methyl-1,3-benzoxazol-2-yl)pyrazol-3-yl]phenyl}-2-methyl-propionamide [M+H]+=360.

N-{4-[4-(1,3-benzoxazol-2-yl)pyrazol-3-yl]phenyl}-2-methyl-propionamide [M+H]+346.

N-[4-(1,3-benzoxazol-2-yl)-1H-pyrazol-3-yl]cyclopropanecarboxamide. [M+H]+=344.

N-{4-[4-(1,3-benzoxazol-2-yl)pyrazol-3-yl]phenyl}benzamide. [M+H]+=380.
N-{4-[4-(5-methyl-1,3-benzoxazol-2-yl)pyrazol-3-yl]phenyl}-3-methoxybenzamide. [M+H]+=410.
N-{4-[4-(1,3-benzoxazol-2-yl)pyrazol-3-yl]phenyl}-4-chlorophenylacetamide. [M+H]+=428.
N-{4-[4-(5-methyl-1,3-benzoxazol-2-yl)pyrazol-3-yl]phenyl}-4-chlorophenylacetamide. [M+H]+=442.

Example 7

Preparation of a Library N-[4-(1,3-benzoxazol-2-yl)pyrazol-3-yl]phenylamides

A combinatorial library of 3874 N-[4-(1,3-benzoxazol-2-yl)pyrazol-3-yl]phenylamides was obtained by portioning and reacting, according to the procedure described in example 6, the 26 resins prepared in example 5 with the 149 carboxylic acids of formula (IX) reported in table II.

Example 8

N-{4-[4(1,3-benzoxazol-2-yl)-pyrazol-3-yl]phenyl}-N'-benzylurea

Benzyl isocyanate (123 μl, 0.10 mmol) was added to a suspension of 2-[3-(4-aminophenyl)-1-tritylpolystyrene-1H-pyrazol-4-yl]-1,3-benzoxazole from example 5 (100 mg, 0.01 mmol) in DCM (1 ml). The obtained suspension was stirred for 20 hrs at 22° C., filtered, washed with DCM (3×), MeOH (3×) and Et2O(3×), and dried under nitrogen flux.

2 ml of a solution of TFA 10% in DCM were then added to resin and the resulting red suspension was stirred for 1 h. Afterward the resin was filtered and washed twice with 1 ml of DCM. The filtered solution was evaporated under nitrogen flux to give 32 mg of a crude solid, that was purified by preparative LC-MS using the following conditions:

| Eluent A: | aqueous solution of trifluoroacetic acid (0.01% v/v) | | |
|---|---|---|---|
| Eluent B: | acetonitrile | | |
| Gradient: | Time (m) | % A | % B |
| | 0 (injection) | 90 | 10 |
| | 8 | 10 | 90 |
| | 10 (end) | 10 | 90 |
| Flow: | 20 ml/m | | |
| Column: | Waters Symmetry ™ C18 19 × 50 mm | | |
| Detector: | mass spectrometer, electrospray ionisation, positive mode. | | |

A liquid handler triggered by the mass spectrometer automatically collected the fractions containing the title compound. After evaporation of the solvent 14 mg of N-{4-[4-(1,3-benzoxazol-2-yl)-pyrazol-3-yl]phenyl}-N'-benzylurea (colorless solid, [M+H]+=409) were obtained. $^1$H-NMR (DMSOd$_6$), diagnostic signals (ppm): 7.74 (d, J=8.6 Hz, 2H), 7.7–7.6 (m, 2H), 4.31 (d, J=6 Hz, 2H).

Analogously, the following compounds were prepared by using the appropriate amino derivatives from example 5 and the appropriate isocyanate:
N-{4-[4-(1,3-benzoxazol-2-yl)-pyrazol-3-yl]phenyl}-N'-phenylurea [M+H]+=409. $^1$H-NMR (DMSOd$_6$), diagnostic signals (ppm): 7.8 (d, J=8.6 Hz), 2H), 7.7–7.6 (m, 2H), 6.96 (t, J=7.3 Hz, 1H).
N-{4-[4-(5-methyl-1,3-benzoxazol-2-yl)-pyrazol-3-yl]phenyl}-N'-benzylurea. [M+H]+=423. $^1$H-NMR (DMSOd$_6$), diagnostic signals (ppm): 7.7 (d, J=6.6 Hz, 2H), 7.5 (d, J=6.6 Hz, 2H), 6.8 (t, 1H), 4.3 (d, 1H), 2.41 (s, 3H).
N-{3-[4-(5-methyl-1,3-benzoxazol-2-yl)-pyrazol-3-yl]phenyl}-N'-benzylurea. [M+H]+=423. $^1$H-NMR (DMSOd$_6$), diagnostic signals (ppm): 7.52 (d, J=8 Hz,1H), 4.28 (d, J=5.8 Hz, 2H), 2.41 (s, 3H).
N-{3-[4-(5-methyl-1,3-benzoxazol-2-yl)-pyrazol-3-yl]phenyl}-N'-phenylurea [M+H]+=409. $^1$H-NMR (DMSOd$_6$), diagnostic signals (ppm): 7.54 (d, J=8 Hz, 1H), 6.95 (t,J=7.3 Hz, 1H), 2.41 (s.3H).
N-{4-[4-(5-methyl-1,3-benzoxazol-2-yl)-pyrazol-3-yl]phenyl}-N'-phenylurea [M+H]+=409.
N-{3-[4-(1,3-benzoxazol-2-yl)-pyrazol-3-yl]phenyl}-N'-phenylurea [M+H]+=395.
N-{3-[4-(1,3-benzoxazol-2-yl)-pyrazol-3-yl]phenyl}-N'-benzylurea. [M+H]+=409.

Example 9

Preparation of a library N-[4-(1,3-benzoxazol-2-yl)pyrazol-3-yl]phenylureas

A combinatorial library of 3172 N-[4-(1,3-benzoxazol-2-yl)pyrazol-3-yl]phenylureas was obtained by portioning and reacting, according to the procedure described in example 8, the 26 resins prepared in example 5 with the 122 isocyanates of formula (XI) reported in table III.

Example 10

N-{3-[4-(1,3-benzoxazol-2-yl)-pyrazol-3-yl]phenyl}toluenesulfonamide

A solution of Diisopropylethylamine (103 μl, 0.06 mmol) and tosyl chloride (0.06 mmol) in 2 ml of DCM was added to a suspension of the resin 6 (100 mg, 0.01 mmol) in DCM (1 ml). The obtained suspension was stirred for 20 hrs at 22° C., filtered, washed with DCM, MeOH and Et2O, and dried under nitrogen flux. 2 ml of a solution of TFA 10% in DCM were then added to resin and the resulting red suspension was stirred for 1 h. Afterward the resin was filtered and washed twice with 1 ml of DCM. The filtered solution was evaporated under nitrogen flux to give 21 mg of a crude solid, that was purified by preparative LC-MS using the following conditions:

| Eluent A: | aqueous solution of trifluoroacetic acid (0.01% v/v) | | |
|---|---|---|---|
| Eluent B: | acetonitrile | | |
| Gradient: | Time (m) | % A | % B |
| | 0 (injection) | 90 | 10 |
| | 8 | 10 | 90 |
| | 10 (end) | 10 | 90 |
| Flow: | 20 ml/m | | |
| Column: | Waters Symmetry ™ C18 19 × 50 mm | | |
| Detector: | mass spectrometer, electrospray ionisation, positive mode. | | |

A liquid handler triggered by the mass spectrometer automatically collected the fractions containing the title compound. After evaporation of the solvent 10 mg of N-{3-[4-(1,3-benzoxazol-2-yl)-pyrazol-3-yl]phenyl}toluensulfonamide (colorless solid, [M+H]+=430) were obtained. $^1$H-NMR (DMSOd$_6$), diagnostic signals (ppm): 7.7–7.6 (m, 2H), 7.4–7.3 (m, 2H), 2.33 (s, 3H).

Analogously, the following compounds were prepared by using the appropriate amino derivatives from example 5 and the appropriate sulphonyl chloride:
N-{3-[4-(5-methyl-1,3-benzoxazol-2-yl)-pyrazol-3-yl]phenyl}toluensulfonamide. [M+H]+=444.

N-{4-[4-(1,3-benzoxazol-2-yl)-pyrazol-3-yl]
phenyl}toluensulfonamide. [M+H]+=430.
N-{4-[4-(5-methyl-1,3-benzoxazol-2-yl)-pyrazol-3-yl]
phenyl}toluensulfonamide. [M+H]+=444.

Example 11

Preparation of a Library N-[4-(1,3-benzoxazol-2-yl)
pyrazol-3-yl]sulfonamides

A combinatorial library of 2184 N-[4-(1,3-benzoxazol-2-yl)pyrazol-3-yl]sulfonamides was obtained by portioning and reacting, according to the procedure described in example 10, the 26 resins prepared in example 5 with the 84 sulphonyl chlorides of formula (X) reported in table IV.

The invention claimed is:

1. A compound which is an oxazolyl-pyrazole derivative represented by formula (I):

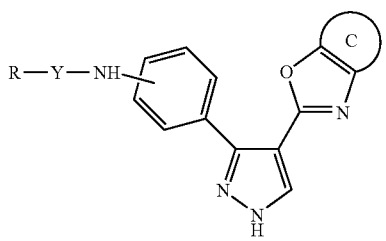

(I)

wherein
R represents a hydrogen atom; a straight or branched $C_1$–$C_8$ alkyl group; a straight or branched $C_2$–$C_8$ alkenyl group; an aryl or aryl $C_1$–$C_6$ alkyl group; a saturated or unsaturated $C_3$–$C_6$ cycloalkyl or cycloalkyloxy group optionally further condensed with 1 or 2 benzene rings; or it is an optionally benzocondensed 5 or 6 membered heterocyclic or heterocyclyl $C_1$–$C_6$ alkyl group, having 1 or 2 heteroatoms selected among nitrogen, oxygen or sulfur; each of the above defined R groups being optionally further substituted by one or more groups selected from:
 i) halogen, nitro, cyano, hydroxy, oxo groups (=O);
 ii) straight or branched $C_1$–$C_6$ alkyl, alkoxyalkyl or perfluorinated alkyl;
 iii) aryl or 5 or 6 membered heterocycles having 1 or 2 heteroatoms selected among nitrogen, oxygen or sulfur, optionally substituted by halogen, nitro, cyano, $C_1$–$C_6$ alkyl or alkoxy;
 iv) straight or branched $C_1$–$C_6$ alkoxy, alkoxyalkyloxy, arylalkyloxy or aryloxy optionally substituted by halogen, nitro, cyano, $C_1$–$C_6$ alkyl or alkoxy;
 v) straight or branched $C_1$–$C_6$ alkylthio or alkylsulphonyl, arylthio or arylsulphonyl;
 vi) $C_3$–$C_6$ cycloalkyl;
 vii) amino, $C_1$–$C_6$ alkylamino, dialkylamino or arylamino;
 viii) $C_1$–$C_6$ alkylcarbonyl, alkyloxycarbonyl, alkylaminocarbonyl, aminocarbonyl, arylcarbonyl or heterocyclylcarbonyl optionally substituted by halogen, nitro, cyano, $C_1$–$C_6$ alkyl or alkoxy;
 ix) $C_1$–$C_6$ alkylcarbonylamino, alkyloxycarbonylamino, arylalkyloxycarbonylamino, arylcarbonylamino or aryloxycarbonylamino;
 x) carboxy, $C_1$–$C_6$ alkylcarbonyloxy or arylcarbonyloxy;

Y is a single bond or a divalent group selected from carbonyl (>C=O), aminocarbonyl (—NHCO—) or sulphonyl (—SO$_2$—);
C is benzene, naphthalene or an optionally benzocondensed 5 or 6 membered heterocycle having 1 or 2 heteroatoms selected among nitrogen, oxygen or sulphur; each of which being optionally further substituted by one or more groups selected from halogen, nitro, cyano, straight or branched $C_1$–$C_6$ alkyl or alkoxy, alkylsulphonyl or aryl groups;
or a pharmaceutically acceptable salt thereof.

2. The compound of claim 1 wherein R is selected from straight or branched $C_1$–$C_8$ alkyl or $C_2$–$C_6$ alkenyl, aryl, aryl $C_1$–$C_6$ alkyl or 5 or 6 membered heterocyclyl, saturated or unsaturated $C_3$–$C_6$ cycloalkyl or cycloalkyloxy optionally further condensed as defined in claim 1, or optionally benzocondensed 5 or 6 membered heterocycle having 1 or 2 heteroatoms selected among nitrogen, oxygen or sulfur; each of which being optionally substituted as defined in claim 1; Y is a divalent group selected from carbonyl (>C=O), aminocarbonyl (—NHCO—) or sulphonyl (—SO$_2$—); and C is a benzene or a naphthalene ring or it is a 5 or 6 membered heterocycle with 1 or 2 heteroatoms selected among nitrogen, oxygen and sulfur, each of which being optionally further substituted as defined in claim 1.

3. The compound of claim 2 wherein R is a straight or branched $C_1$–$C_8$ alkyl or $C_2$–$C_6$ alkenyl, phenyl, phenyl $C_1$–$C_6$ alkyl, 1-naphthyl, 2-naphthyl, biphenyl, pyridyl, pyrazolyl, thienyl, isoxazolyl, thiazolyl, pyrazolyl, cyclopropyl, cyclobutyl, cyclopentyl, fluorene-9-yl, cyclohexyl, cyclohexyloxy, cyclohexenyl, tetrahydronaphthyl, piperidine or tetrahydroquinoline; each of which being optionally further substituted as defined in claim 1; Y is a divalent group selected from carbonyl (>C=O), aminocarbonyl (—NHCO—) or sulphonyl (—SO$_2$—); and C is a benzene, naphthalene or pyridine ring, each of which being optionally further substituted as defined in claim 1.

4. The compound of claim 1 wherein Y is a carbonyl (>C=O) group.

5. The compound of claim 1 wherein Y is an aminocarbonyl (—NHCO—) group.

6. The compound of claim 1 wherein Y is a sulphonyl (—SO$_2$—) group.

7. The compound of claim 1, optionally in the form of a pharmaceutically acceptable salt, selected from the group consisting of:
 1. N-{4-[4-(1,3-benzoxazol-2-yl)pyrazol-3-yl]phenyl}-N'-methyl urea;
 2. N-{4-[4-(1,3-benzoxazol-2-yl)pyrazol-3-yl]phenyl}-N'-ethyl urea;
 3. N-{4-[4-(1,3-benzoxazol-2-yl)pyrazol-3-yl]phenyl}-N'-isopropyl urea;
 4. N-{4-[4-(1,3-benzoxazol-2-yl)pyrazol-3-yl]phenyl}-N'-phenyl urea;
 5. N-{4-[4-(1,3-benzoxazol-2-yl)pyrazol-3-yl]phenyl}-N'-3-chlorophenyl urea;
 6. N-{4-[4-(1,3-benzoxazol-2-yl)pyrazol-3-yl]phenyl}-N'-4-fluorophenyl urea;
 7. N-{4-[4-(1,3-benzoxazol-2-yl)pyrazol-3-yl]phenyl}-N'-2,4-fluorophenyl urea;
 8. N-{4-[4-(1,3-benzoxazol-2-yl)pyrazol-3-yl]phenyl}-N'-benzyl urea;
 9. N-{4-[4-(1,3-benzoxazol-2-yl)pyrazol-3-yl]phenyl}-N'-4-methoxyphenyl urea;
 10. N-{4-[4-(1,3-benzoxazol-2-yl)pyrazol-3-yl]phenyl}-N'-2,6-dimethylphenyl urea;

11. N-{4-[4-(1,3-benzoxazol-2-yl)pyrazol-3-yl]phenyl}-N'-3-methoxyphenyl urea;
12. N-{4-[4-(1,3-benzoxazol-2-yl)pyrazol-3-yl]phenyl}benzenesulphonamide;
13. N-{4-[4-(1,3-benzoxazol-2-yl)pyrazol-3-yl]phenyl}methanesulphonamide;
14. N-{4-[4-(1,3-benzoxazol-2-yl)pyrazol-3-yl]phenyl}toluensulphonamide;
15. N-{4-[4-(1,3-benzoxazol-2-yl)pyrazol-3-yl]phenyl}ethanesulphonamide;
16. N-{4-[4-(1,3-benzoxazol-2-yl)pyrazol-3-yl]phenyl}acetamide;
17. N-{4-[4-(1,3-benzoxazol-2-yl)pyrazol-3-yl]phenyl}benzamide;
18. N-{4-[4-(1,3-benzoxazol-2-yl)pyrazol-3-yl]phenyl}chromone-3-carboxamide;
19. N-{4-[4-(1,3-benzoxazol-2-yl)pyrazol-3-yl]phenyl}cis-2-(2-thiophenecarbonyl)-1-cyclohexanecarboxamide;
20. N-{4-[4-(1,3-benzoxazol-2-yl)pyrazol-3-yl]phenyl}cyclobutanecarboxamide;
21. N-{4-[4-(1,3-benzoxazol-2-yl)pyrazol-3-yl]phenyl}cyclopentanecarboxamide;
22. N-{4-[4-(1,3-benzoxazol-2-yl)pyrazol-3-yl]phenyl}dicyclohexylacetamide;
23. N-{4-[4-(1,3-benzoxazol-2-yl)pyrazol-3-yl]phenyl}diphenylacetamide;
24. N-{4-[4-(1,3-benzoxazol-2-yl)pyrazol-3-yl]phenyl}isoxazole-5-carboxamide;
25. N-{4-[4-(1,3-benzoxazol-2-yl)pyrazol-3-yl]phenyl}menthyloxyacetamide;
26. N-{4-[4-(1,3-benzoxazol-2-yl)pyrazol-3-yl]phenyl}nicotinamide;
27. N-{4-[4-(1,3-benzoxazol-2-yl)pyrazol-3-yl]phenyl}phenylacetamide;
28. N-{4-[4-(1,3-benzoxazol-2-yl)pyrazol-3-yl]phenyl}picolinamide;
29. N-{4-[4-(1,3-benzoxazol-2-yl)pyrazol-3-yl]phenyl}p-tolylacetamide;
30. N-{4-[4-(1,3-benzoxazol-2-yl)pyrazol-3-yl]phenyl}succinamide;
31. N-{4-[4-(1,3-benzoxazol-2-yl)pyrazol-3-yl]phenyl}tert-butylacetamide;
32. N-{4-[4-(1,3-benzoxazol-2-yl)pyrazol-3-yl]phenyl}thiophene-3-acetamide;
33. N-{4-[4-(1,3-benzoxazol-2-yl)pyrazol-3-yl]phenyl}thiophene-3-carboxamide;
34. N-{3-[4-(6-methyl-1,3-benzoxazol-2-yl)pyrazol-3-yl]phenyl}-N'-methyl urea;
35. N-{3-[4-(6-methyl-1,3-benzoxazol-2-yl)pyrazol-3-yl]phenyl}-N'-ethyl urea;
36. N-{3-[4-(6-methyl-1,3-benzoxazol-2-yl)pyrazol-3-yl]phenyl}-N'-isopropyl urea;
37. N-{3-[4-(6-methyl-1,3-benzoxazol-2-yl)pyrazol-3-yl]phenyl}-N'-phenyl urea;
38. N-{3-[4-(6-methyl-1,3-benzoxazol-2-yl)pyrazol-3-yl]phenyl}-N'-3-chlorophenyl urea;
39. N-{3-[4-(6-methyl-1,3-benzoxazol-2-yl)pyrazol-3-yl]phenyl}-N'-4-fluorophenyl urea;
40. N-{3-[4-(6-methyl-1,3-benzoxazol-2-yl)pyrazol-3-yl]phenyl}-N'-2,4-fluorophenyl urea;
41. N-{3-[4-(6-methyl-1,3-benzoxazol-2-yl)pyrazol-3-yl]phenyl}-N'-benzyl urea;
42. N-{3-[4-(6-methyl-1,3-benzoxazol-2-yl)pyrazol-3-yl]phenyl}-N'-4-methoxyphenyl urea;
43. N-{3-[4-(6-methyl-1,3-benzoxazol-2-yl)pyrazol-3-yl]phenyl}-N'-2,6-dimethylphenyl urea;
44. N-{3-[4-(6-methyl-1,3-benzoxazol-2-yl)pyrazol-3-yl]phenyl}-N'-3-methoxyphenyl urea;
45. N-{3-[4-(6-methyl-1,3-benzoxazol-2-yl)pyrazol-3-yl]phenyl}benzenesulphonamide;
46. N-{3-[4-(6-methyl-1,3-benzoxazol-2-yl)pyrazol-3-yl]phenyl}methanesulphonamide;
47. N-{3-[4-(6-methyl-1,3-benzoxazol-2-yl)pyrazol-3-yl]phenyl}toluensulphonamide;
48. N-{3-[4-(6-methyl-1,3-benzoxazol-2-yl)pyrazol-3-yl]phenyl}ethanesulphonamide;
49. N-{3-[4-(6-methyl-1,3-benzoxazol-2-yl)pyrazol-3-yl]phenyl}acetamide;
50. N-{3-[4-(6-methyl-1,3-benzoxazol-2-yl)pyrazol-3-yl]phenyl}benzamide;
51. N-{3-[4-(6-methyl-1,3-benzoxazol-2-yl)pyrazol-3-yl]phenyl}chromone-3-carboxamide;
52. N-{3-[4-(6-methyl-1,3-benzoxazol-2-yl)pyrazol-3-yl]phenyl}cis-2-(2-thiophenecarbonyl)-1-cyclohexanecarboxamide;
53. N-{3-[4-(6-methyl-1,3-benzoxazol-2-yl)pyrazol-3-yl]phenyl}cyclobutanecarboxamide;
54. N-{3-[4-(6-methyl-1,3-benzoxazol-2-yl)pyrazol-3-yl]phenyl}cyclopentanecarboxamide;
55. N-{3-[4-(6-methyl-1,3-benzoxazol-2-yl)pyrazol-3-yl]phenyl}dicyclohexylacetamide;
56. N-{3-[4-(6-methyl-1,3-benzoxazol-2-yl)pyrazol-3-yl]phenyl}diphenylacetamide;
57. N-{3-[4-(6-methyl-1,3-benzoxazol-2-yl)pyrazol-3-yl]phenyl}isoxazole-5-carboxamide;
58. N-{3-[4-(6-methyl-1,3-benzoxazol-2-yl)pyrazol-3-yl]phenyl}menthyloxyacetamide;
59. N-{3-[4-(6-methyl-1,3-benzoxazol-2-yl)pyrazol-3-yl]phenyl}nicotinamide;
60. N-{3-[4-(6-methyl-1,3-benzoxazol-2-yl)pyrazol-3-yl]phenyl}phenylacetamide;
61. N-{3-[4-(6-methyl-1,3-benzoxazol-2-yl)pyrazol-3-yl]phenyl}picolinamide;
62. N-{3-[4-(6-methyl-1,3-benzoxazol-2-yl)pyrazol-3-yl]phenyl}(p-tolyl)acetamide;
63. N-{3-[4-(6-methyl-1,3-benzoxazol-2-yl)pyrazol-3-yl]phenyl}succinamide;
64. N-{3-[4-(6-methyl-1,3-benzoxazol-2-yl)pyrazol-3-yl]phenyl}tert-butylacetamide;
65. N-{3-[4-(6-methyl-1,3-benzoxazol-2-yl)pyrazol-3-yl]phenyl}thiophene-3-acetamide;
66. N-{3-[4-(6-methyl-1,3-benzoxazol-2-yl)pyrazol-3-yl]phenyl}thiophene-3-carboxamide;
67. N-{4-[4-(6-methyl-1,3-benzoxazol-2-yl)pyrazol-3-yl]phenyl}9-fluorenecarboxamide;
68. N-{4-[4-(6-methyl-1,3-benzoxazol-2-yl)pyrazol-3-yl]phenyl}(3,5-dimethoxyphenyl)acetamide;
69. N-{4-[4-(6-methyl-1,3-benzoxazol-2-yl)pyrazol-3-yl]phenyl}1-(aminocarbonyl)-1-cyclopropanecarboxamide;
70. N-{4-[4-(6-methyl-1,3-benzoxazol-2-yl)pyrazol-3-yl]phenyl}1-(p-tolyl)-1-cyclopentanecarboxamide;
71. N-{4-[4-(6-methyl-1,3-benzoxazol-2-yl)pyrazol-3-yl]phenyl}1,2,3,4-tetrahydro-2-naphtalene amide;
72. N-{4-[4-(6-methyl-1,3-benzoxazol-2-yl)pyrazol-3-yl]phenyl}1-cyanocyclopropanecarboxamide;
73. N-{4-[4-(6-methyl-1,3-benzoxazol-2-yl)pyrazol-3-yl]phenyl}1-methylcyclopropane-1-carboxamide;
74. N-{4-[4-(6-methyl-1,3-benzoxazol-2-yl)pyrazol-3-yl]phenyl}1-naphtalene amide;
75. N-{4-[4-(6-methyl-1,3-benzoxazol-2-yl)pyrazol-3-yl]phenyl}1-phenyl-1-cyclopropanecarboxamide;

76. N-{4-[4-(6-methyl-1,3-benzoxazol-2-yl)pyrazol-3-yl]phenyl}2-(2-methoxyethoxy)acetamide;
77. N-{4-[4-(6-methyl-1,3-benzoxazol-2-yl)pyrazol-3-yl]phenyl}2-(4-chlorobenzoyl)benzamide;
78. N-{4-[4-(6-methyl-1,3-benzoxazol-2-yl)pyrazol-3-yl]phenyl}2-(4-nitrophenyl)propionamide;
79. N-{4-[4-(6-methyl-1,3-benzoxazol-2-yl)pyrazol-3-yl]phenyl}2-(4-pyridyl)thiazole-4-carboxamide;
80. N-{4-[4-(6-methyl-1,3-benzoxazol-2-yl)pyrazol-3-yl]phenyl}2-(benzyloxycarbonylamino)4-cyclohexene-1-carboxamide;
81. N-{4-[4-(6-methyl-1,3-benzoxazol-2-yl)pyrazol-3-yl]phenyl}2-(benzyloxycarbonylamino)-cyclohexanecarboxamide;
82. N-{4-[4-(6-methyl-1,3-benzoxazol-2-yl)pyrazol-3-yl]phenyl}2,2,3,3-tetramethylcyclopropanecarboxamide;
83. N-{4-[4-(6-methyl-1,3-benzoxazol-2-yl)pyrazol-3-yl]phenyl}2,2-dimethyl4-pentenamide;
84. N-{4-[4-(6-methyl-1,3-benzoxazol-2-yl)pyrazol-3-yl]phenyl}2,2-dimethylhexanamide;
85. N-{4-[4-(6-methyl-1,3-benzoxazol-2-yl)pyrazol-3-yl]phenyl}2,3-dichlorophenoxyacetamide;
86. N-{4-[4-(6-methyl-1,3-benzoxazol-2-yl)pyrazol-3-yl]phenyl}2,4,6-trimethoxyphenylacetamide;
87. N-{4-[4-(6-methyl-1,3-benzoxazol-2-yl)pyrazol-3-yl]phenyl}2,4-dichlorophenylacetamide;
88. N-{4-[4-(6-methyl-1,3-benzoxazol-2-yl)pyrazol-3-yl]phenyl}2,5-dibromobenzamide;
89. N-{4-[4-(6-methyl-1,3-benzoxazol-2-yl)pyrazol-3-yl]phenyl}2,5-dimethoxybenzamide;
90. N-{4-[4-(6-methyl-1,3-benzoxazol-2-yl)pyrazol-3-yl]phenyl}2,6-dichloropyridine-4-carboxamide;
91. N-{4-[4-(6-methyl-1,3-benzoxazol-2-yl)pyrazol-3-yl]phenyl}2,6-dimethylbenzamide;
92. N-{4-[4-(6-methyl-1,3-benzoxazol-2-yl)pyrazol-3-yl]phenyl}2-acetamido-5-bromobenzamide;
93. N-{4-[4-(6-methyl-1,3-benzoxazol-2-yl)pyrazol-3-yl]phenyl}2-acetoxypropionamide;
94. N-{4-[4-(6-methyl-1,3-benzoxazol-2-yl)pyrazol-3-yl]phenyl}2-benzyloxyphenylacetamide;
95. N-{4-[4-(6-methyl-1,3-benzoxazol-2-yl)pyrazol-3-yl]phenyl}2-biphenylcarboxamide;
96. N-{4-[4-(6-methyl-1,3-benzoxazol-2-yl)pyrazol-3-yl]phenyl}2-bromo-4-fluorobenzamide;
97. N-{4-[4-(6-methyl-1,3-benzoxazol-2-yl)pyrazol-3-yl]phenyl}2-chloro-4-methylsulfonylbenzamide;
98. N-{4-[4-(6-methyl-1,3-benzoxazol-2-yl)pyrazol-3-yl]phenyl}2-fluoro-6-iodobenzamide;
99. N-{4-[4-(6-methyl-1,3-benzoxazol-2-yl)pyrazol-3-yl]phenyl}2-fluorobenzamide;
100. N-{4-[4-(6-methyl-1,3-benzoxazol-2-yl)pyrazol-3-yl]phenyl}2-ketobutyramide;
101. N-{4-[4-(5-chloro-1,3-benzoxazol-2-yl)pyrazol-3-yl]phenyl}2-methoxypropionamide;
102. N-{4-[4-(5-chloro-1,3-benzoxazol-2-yl)pyrazol-3-yl]phenyl}2-methyl-4,4,4-trifluorobutyramide;
103. N-{4-[4-(5-chloro-1,3-benzoxazol-2-yl)pyrazol-3-yl]phenyl}2-naphtaleneamide;
104. N-{4-[4-(5-chloro-1,3-benzoxazol-2-yl)pyrazol-3-yl]phenyl}3-(2-chloro-6-fluorophenyl)-5-methylisoxazole-4-carboxamide;
105. N-{4-[4-(5-chloro-1,3-benzoxazol-2-yl)pyrazol-3-yl]phenyl}3-(2-methoxyphenyl)propionamide;
106. N-{4-[4-(5-chloro-1,3-benzoxazol-2-yl)pyrazol-3-yl]phenyl}3-(2-thenoyl)-propionamide;
107. N-{4-[4-(5-chloro-1,3-benzoxazol-2-yl)pyrazol-3-yl]phenyl}3-(diethylamino)propionamide;
108. N-{4-[4-(5-chloro-1,3-benzoxazol-2-yl)pyrazol-3-yl]phenyl}3-(methylsulphonyl)benzamide;
109. N-{4-[4-(5-chloro-1,3-benzoxazol-2-yl)pyrazol-3-yl]phenyl}3-(phenylsulphonyl)propionamide;
110. N-{4-[4-(5-chloro-1,3-benzoxazol-2-yl)pyrazol-3-yl]phenyl}3,4,5-trimethoxybenzamide;
111. N-{4-[4-(5-chloro-1,3-benzoxazol-2-yl)pyrazol-3-yl]phenyl}3,4-diethoxybenzamide;
112. N-{4-[4-(5-chloro-1,3-benzoxazol-2-yl)pyrazol-3-yl]phenyl}3,4-dimethoxybenzamide;
113. N-{4-[4-(5-chloro-1,3-benzoxazol-2-yl)pyrazol-3-yl]phenyl}3,5-diacetamidobenzamide;
114. N-{4-[4-(5-chloro-1,3-benzoxazol-2-yl)pyrazol-3-yl]phenyl}3,5-dibromobenzamide;
115. N-{4-[4-(5-chloro-1,3-benzoxazol-2-yl)pyrazol-3-yl]phenyl}3-acetoxybenzamide;
116. N-{4-[4-(5-chloro-1,3-benzoxazol-2-yl)pyrazol-3-yl]phenyl}3-bromobenzamide;
117. N-{4-[4-(5-chloro-1,3-benzoxazol-2-yl)pyrazol-3-yl]phenyl}3-chloro-2-methylbenzamide;
118. N-{4-[4-(5-chloro-1,3-benzoxazol-2-yl)pyrazol-3-yl]phenyl}3-cyanobenzamide;
119. N-{4-[4-(5-chloro-1,3-benzoxazol-2-yl)pyrazol-3-yl]phenyl}3-fluorophenylacetamide;
120. N-{4-[4-(5-chloro-1,3-benzoxazol-2-yl)pyrazol-3-yl]phenyl}3-methoxycyclohexanecarboxamide;
121. N-{4-[4-(5-chloro-1,3-benzoxazol-2-yl)pyrazol-3-yl]phenyl}3-methyl-1-cyclohexanecarboxamide;
122. N-{4-[4-(5-chloro-1,3-benzoxazol-2-yl)pyrazol-3-yl]phenyl}3-methylthiopropionamide;
123. N-{4-[4-(5-chloro-1,3-benzoxazol-2-yl)pyrazol-3-yl]phenyl}3-pyridinepropionamide;
124. N-{4-[4-(5-chloro-1,3-benzoxazol-2-yl)pyrazol-3-yl]phenyl}4-(3,4-dimethoxyphenyl)butyramide;
125. N-{4-[4-(5-chloro-1,3-benzoxazol-2-yl)pyrazol-3-yl]phenyl}4-(dimethylamino)phenylacetamide;
126. N-{4-[4-(5-chloro-1,3-benzoxazol-2-yl)pyrazol-3-yl]phenyl}4-(tert-butoxymethyl)benzamide;
127. N-{4-[4-(5-chloro-1,3-benzoxazol-2-yl)pyrazol-3-yl]phenyl}4,5-dibromothiophene-2-carboxamide;
128. N-{4-[4-(5-chloro-1,3-benzoxazol-2-yl)pyrazol-3-yl]phenyl}4-acetamido-3-nitrobenzamide;
129. N-{4-[4-(5-chloro-1,3-benzoxazol-2-yl)pyrazol-3-yl]phenyl}4-acetamidobutyramide;
130. N-{4-[4-(5-chloro-1,3-benzoxazol-2-yl)pyrazol-3-yl]phenyl}4-biphenylcarboxamide;
131. N-{4-[4-(5-chloro-1,3-benzoxazol-2-yl)pyrazol-3-yl]phenyl}4-bromo-2-fluorobenzamide;
132. N-{4-[4-(5-chloro-1,3-benzoxazol-2-yl)pyrazol-3-yl]phenyl}4-bromo-2-methylbenzamide;
133. N-{4-[4-(5-chloro-1,3-benzoxazol-2-yl)pyrazol-3-yl]phenyl}4-bromo-3-methylbenzamide;
134. N-{4-[4-(5-chloro-1,3-benzoxazol-2-yl)pyrazol-3-yl]phenyl}4-carboxybenzenesulfonamide;
135. N-{4-[4-(5-methyl-1,3-benzoxazol-2-yl)pyrazol-3-yl]phenyl}4-chloro-alpha-methylphenylacetamide;
136. N-{4-[4-(5-methyl-1,3-benzoxazol-2-yl)pyrazol-3-yl]phenyl}4-cyanobenzamide;
137. N-{4-[4-(5-methyl-1,3-benzoxazol-2-yl)pyrazol-3-yl]phenyl}4-diethylaminobenzamide;
138. N-{4-[4-(5-methyl-1,3-benzoxazol-2-yl)pyrazol-3-yl]phenyl}4-dimethylaminobutyramide;
139. N-{4-[4-(5-methyl-1,3-benzoxazol-2-yl)pyrazol-3-yl]phenyl}4-ethoxyphenylacetamide;
140. N-{4-[4-(5-methyl-1,3-benzoxazol-2-yl)pyrazol-3-yl]phenyl}4-iodobenzamide;

141. N-{4-[4-(5-methyl-1,3-benzoxazol-2-yl)pyrazol-3-yl]phenyl}4-iodophenylacetamide;
142. N-{4-[4-(5-methyl-1,3-benzoxazol-2-yl)pyrazol-3-yl]phenyl}4-isopropylphenoxyacetamide;
143. N-{4-[4-(5-methyl-1,3-benzoxazol-2-yl)pyrazol-3-yl]phenyl}4-methyl-3-nitrobenzamide;
144. N-{4-[4-(5-methyl-1,3-benzoxazol-2-yl)pyrazol-3-yl]phenyl}5-(2-thienyl)pentanamide;
145. N-{4-[4-(5-methyl-1,3-benzoxazol-2-yl)pyrazol-3-yl]phenyl}5,6-dichloronicotinamide;
146. N-{4-[4-(5-methyl-1,3-benzoxazol-2-yl)pyrazol-3-yl]phenyl}5-acetamido-2-nitrobenzamide;
147. N-{4-[4-(5-methyl-1,3-benzoxazol-2-yl)pyrazol-3-yl]phenyl}5-benzoylpentanamide;
148. N-{4-[4-(5-methyl-1,3-benzoxazol-2-yl)pyrazol-3-yl]phenyl}5-bromo-3-pyridylacetamide;
149. N-{4-[4-(5-methyl-1,3-benzoxazol-2-yl)pyrazol-3-yl]phenyl}5-chlorothianaphthene-3-acetamide;
150. N-{4-[4-(5-methyl-1,3-benzoxazol-2-yl)pyrazol-3-yl]phenyl}5-methyl-1-phenylpyrazole-4-carboxamide;
151. N-{4-[4-(5-methyl-1,3-benzoxazol-2-yl)pyrazol-3-yl]phenyl}5-methylhexanamide;
152. N-{4-[4-(5-methyl-1,3-benzoxazol-2-yl)pyrazol-3-yl]phenyl}5-methylisoxazole-4-carboxamide;
153. N-{4-[4-(5-methyl-1,3-benzoxazol-2-yl)pyrazol-3-yl]phenyl}6-acetoxy-2-naphtaleneamide;
154. N-{4-[4-(5-methyl-1,3-benzoxazol-2-yl)pyrazol-3-yl]phenyl}6-cyanonicotinamide;
155. N-{4-[4-(5-methyl-1,3-benzoxazol-2-yl)pyrazol-3-yl]phenyl}7-chloro-1-ethyl-6-fluoro4-oxohydroquinoline-3-carboxamide;
156. N-{4-[4-(5-tertbutyl-1,3-benzoxazol-2-yl)pyrazol-3-yl]phenyl}-N'-methyl urea;
157. N-{4-[4-(5-tertbutyl-1,3-benzoxazol-2-yl)pyrazol-3-yl]phenyl}-N'-ethyl urea;
158. N-{4-[4-(5-tertbutyl-1,3-benzoxazol-2-yl)pyrazol-3-yl]phenyl}-N'-isopropyl urea;
159. N-{4-[4-(5-tertbutyl-1,3-benzoxazol-2-yl)pyrazol-3-yl]phenyl}-N'-phenyl urea;
160. N-{4-[4-(5-tertbutyl-1,3-benzoxazol-2-yl)pyrazol-3-yl]phenyl}-N'-3-chlorophenyl urea;
161. N-{4-[4-(5-tertbutyl-1,3-benzoxazol-2-yl)pyrazol-3-yl]phenyl}-N'-4-fluorophenyl urea;
162. N-{4-[4-(5-tertbutyl-1,3-benzoxazol-2-yl)pyrazol-3-yl]phenyl}-N'-2,4-fluorophenyl urea;
163. N-{4-[4-(5-tertbutyl-1,3-benzoxazol-2-yl)pyrazol-3-yl]phenyl}-N'-benzyl urea;
164. N-{4-[4-(5-tertbutyl-1,3-benzoxazol-2-yl)pyrazol-3-yl]phenyl}-N'-4-methoxyphenyl urea;
165. N-{4-[4-(5-tertbutyl-1,3-benzoxazol-2-yl)pyrazol-3-yl]phenyl}-N'-2,6-dimethylphenyl urea;
166. N-{4-[4-(5-tertbutyl-1,3-benzoxazol-2-yl)pyrazol-3-yl]phenyl}-N'-3-methoxyphenyl urea;
167. N-{4-[4-(5-tertbutyl-1,3-benzoxazol-2-yl)pyrazol-3-yl]phenyl}benzenesulphonamide;
168. N-{4-[4-(5-tertbutyl-1,3-benzoxazol-2-yl)pyrazol-3-yl]phenyl}methanesulphonamide;
169. N-{4-[4-(5-tertbutyl-1,3-benzoxazol-2-yl)pyrazol-3-yl]phenyl}toluensulphonamide;
170. N-{4-[4-(5-tertbutyl-1,3-benzoxazol-2-yl)pyrazol-3-yl]phenyl}ethanesulphonamide;
171. N-{4-[4-(5-tertbutyl-1,3-benzoxazol-2-yl)pyrazol-3-yl]phenyl}acetamide;
172. N-{4-[4-(5-tertbutyl-1,3-benzoxazol-2-yl)pyrazol-3-yl]phenyl}benzamide;
173. N-{4-[4-(5-tertbutyl-1,3-benzoxazol-2-yl)pyrazol-3-yl]phenyl}chromone-3-carboxamide;
174. N-{4-[4-(5-tertbutyl-1,3-benzoxazol-2-yl)pyrazol-3-yl]phenyl}cis-2-(2-thiophenecarbonyl)-1-cyclohexanecarboxamide;
175. N-{4-[4-(5-tertbutyl-1,3-benzoxazol-2-yl)pyrazol-3-yl]phenyl}cyclobutanecarboxamide;
176. N-{4-[4-(5-tertbutyl-1,3-benzoxazol-2-yl)pyrazol-3-yl]phenyl}cyclopentanecarboxamide;
177. N-{4-[4-(5-tertbutyl-1,3-benzoxazol-2-yl)pyrazol-3-yl]phenyl}dicyclohexylacetamide;
178. N-{4-[4-(5-tertbutyl-1,3-benzoxazol-2-yl)pyrazol-3-yl]phenyl}diphenylacetamide;
179. N-{4-[4-(5,7-chloro-6-methyl-1,3-benzoxazol-2-yl)pyrazol-3-yl]phenyl}isoxazole-5-carboxamide;
180. N-{4-[4-(5,7-chloro-6-methyl-1,3-benzoxazol-2-yl)pyrazol-3-yl]phenyl}menthyloxyacetamide;
181. N-{4-[4-(5,7-chloro-6-methyl-1,3-benzoxazol-2-yl)pyrazol-3-yl]phenyl}nicotinamide;
182. N-{4-[4-(5,7-chloro-6-methyl-1,3-benzoxazol-2-yl)pyrazol-3-yl]phenyl}phenylacetamide;
183. N-{4-[4-(5,7-chloro-6-methyl-1,3-benzoxazol-2-yl)pyrazol-3-yl]phenyl}picolinamide;
184. N-{4-[4-(5,7-chloro-6-methyl-1,3-benzoxazol-2-yl)pyrazol-3-yl]phenyl}p-tolylacetamide;
185. N-{4-[4-(5,7-chloro-6-methyl-1,3-benzoxazol-2-yl)pyrazol-3-yl]phenyl}succinamide;
186. N-{4-[4-(5,7-chloro-6-methyl-1,3-benzoxazol-2-yl)pyrazol-3-yl]phenyl}tert-butylacetamide;
187. N-{4-[4-(5,7-chloro-6-methyl-1,3-benzoxazol-2-yl)pyrazol-3-yl]phenyl}thiophene-3-acetamide;
188. N-{4-[4-(5,7-chloro-6-methyl-1,3-benzoxazol-2-yl)pyrazol-3-yl]phenyl}thiophene-3-carboxamide;
189. N-{4-[4-(5-ethylsulfonyl-1,3-benzoxazol-2-yl)pyrazol-3-yl]phenyl}4-chloro-alpha-methylphenylacetamide;
190. N-{4-[4-(5-ethylsulfonyl-1,3-benzoxazol-2-yl)pyrazol-3-yl]phenyl}4-cyanobenzamide;
191. N-{4-[4-(5-ethylsulfonyl-1,3-benzoxazol-2-yl)pyrazol-3-yl]phenyl}4-diethylaminobenzamide;
192. N-{4-[4-(5-ethylsulfonyl-1,3-benzoxazol-2-yl)pyrazol-3-yl]phenyl}4-dimethylaminobutyramide;
193. N-{4-[4-(5-ethylsulfonyl-1,3-benzoxazol-2-yl)pyrazol-3-yl]phenyl}4-ethoxyphenylacetamide;
194. N-{4-[4-(5-ethylsulfonyl-1,3-benzoxazol-2-yl)pyrazol-3-yl]phenyl}4-iodobenzamide;
195. N-{4-[4-(5-ethylsulfonyl-1,3-benzoxazol-2-yl)pyrazol-3-yl]phenyl}4-iodophenylacetamide;
196. N-{4-[4-(5-ethylsulfonyl-1,3-benzoxazol-2-yl)pyrazol-3-yl]phenyl}4-isopropylphenoxyacetamide;
197. N-{4-[4-(5-ethylsulfonyl-1,3-benzoxazol-2-yl)pyrazol-3-yl]phenyl}4-methyl-3-nitrobenzamide;
198. N-{4-[4-(5-ethylsulfonyl-1,3-benzoxazol-2-yl)pyrazol-3-yl]phenyl}5-(2-thienyl)pentanamide;
199. N-{4-[4-(5-phenyl-1,3-benzoxazol-2-yl)pyrazol-3-yl]phenyl}5,6-dichloronicotinamide;
200. N-{4-[4-(5-phenyl-1,3-benzoxazol-2-yl)pyrazol-3-yl]phenyl}5-acetamido-2-nitrobenzamide;
201. N-{4-[4-(5-phenyl-1,3-benzoxazol-2-yl)pyrazol-3-yl]phenyl}5-benzoylpentanamide;
202. N-{4-[4-(5-phenyl-1,3-benzoxazol-2-yl)pyrazol-3-yl]phenyl}5-bromo-3-pyridylacetamide;
203. N-{4-[4-(5-phenyl-1,3-benzoxazol-2-yl)pyrazol-3-yl]phenyl}5-chlorothianaphthene-3-acetamide;
204. N-{4-[4-(4-methyl-1,3-benzoxazol-2-yl)pyrazol-3-yl]phenyl}5-methyl-1-phenylpyrazole-4-carboxamide;
205. N-{4-[4-(4-methyl-1,3-benzoxazol-2-yl)pyrazol-3-yl]phenyl}5-methylhexanamide;

206. N-{4-[4-(4-methyl-1,3-benzoxazol-2-yl)pyrazol-3-yl]phenyl}5-methylisoxazole-4-carboxamide;
207. N-{4-[4-(4-methyl-1,3-benzoxazol-2-yl)pyrazol-3-yl]phenyl}6-acetoxy-2-naphtaleneamide;
208. N-{4-[4-(4-methyl-1,3-benzoxazol-2-yl)pyrazol-3-yl]phenyl}6-cyanonicotinamide;
209. N-{4-[4-(4-methyl-1,3-benzoxazol-2-yl)pyrazol-3-yl]phenyl}7-chloro-1-ethyl-6-fluoro-4-oxohydroquinoline-3-carboxamide;
210. N-{4-[4-(4-methyl-1,3-benzoxazol-2-yl)pyrazol-3-yl]phenyl}9-fluorenecarboxamide;
211. N-{4-[4-(4-methyl-1,3-benzoxazol-2-yl)pyrazol-3-yl]phenyl}(3,5-dimethoxyphenyl)acetamide;
212. N-{4-[4-(4-methyl-1,3-benzoxazol-2-yl)pyrazol-3-yl]phenyl}1-(aminocarbonyl)-1-cyclopropanecarboxamide;
213. N-{4-[4-(4-methyl-1,3-benzoxazol-2-yl)pyrazol-3-yl]phenyl}1-(p-tolyl)-1-cyclopentanecarboxamide;
214. N-{4-[4-(4-methyl-1,3-benzoxazol-2-yl)pyrazol-3-yl]phenyl}1,2,3,4-tetrahydro-2-naphtaleneamide;
215. N-{4-[4-(4-methyl-1,3-benzoxazol-2-yl)pyrazol-3-yl]phenyl}1-cyanocyclopropanecarboxamide;
216. N-{4-[4-(4-methyl-1,3-benzoxazol-2-yl)pyrazol-3-yl]phenyl}1-methylcyclopropane-1-carboxamide;
217. N-{4-[4-(4-methyl-1,3-benzoxazol-2-yl)pyrazol-3-yl]phenyl}1-naphtalene amide;
218. N-{4-[4-(4-methyl-1,3-benzoxazol-2-yl)pyrazol-3-yl]phenyl}1-phenyl-1-cyclopropanecarboxamide;
219. N-{4-[4-(4-methyl-1,3-benzoxazol-2-yl)pyrazol-3-yl]phenyl}2-(2-methoxyethoxy)acetamide;
220. N-{4-[4-(4-methyl-1,3-benzoxazol-2-yl)pyrazol-3-yl]phenyl}2-(4-chlorobenzoyl)benzamide;
221. N-{4-[4-(4-methyl-1,3-benzoxazol-2-yl)pyrazol-3-yl]phenyl}2-(4-nitrophenyl)propionamide;
222. N-{4-[4-(4-methyl-1,3-benzoxazol-2-yl)pyrazol-3-yl]phenyl}2-(4-pyridyl)thiazole-4-carboxamide;
223. N-{4-[4-(4-methyl-1,3-benzoxazol-2-yl)pyrazol-3-yl]phenyl}2-(benzyloxycarbonylamino)4-cyclohexene-1-carboxamide;
224. N-{4-[4-(4-methyl-7-isopropyl-1,3-benzoxazol-2-yl)pyrazol-3-yl]phenyl}2-(benzyloxycarbonylamino)-cyclohexanecarboxamide;
225. N-{4-[4-(4-methyl-7-isopropyl-1,3-benzoxazol-2-yl)pyrazol-3-yl]phenyl}2,2,3,3-tetramethylcyclopropanecarboxamide;
226. N-{4-[4-(4-methyl-7-isopropyl-1,3-benzoxazol-2-yl)pyrazol-3-yl]phenyl}2,2-dimethyl-4-pentenamide;
227. N-{4-[4-(4-methyl-7-isopropyl-1,3-benzoxazol-2-yl)pyrazol-3-yl]phenyl}2,2-dimethylhexanamide;
228. N-{4-[4-(4-methyl-7-isopropyl-1,3-benzoxazol-2-yl)pyrazol-3-yl]phenyl}2,3-dichlorophenoxyacetamide;
229. N-{4-[4-(4-methyl-7-isopropyl-1,3-benzoxazol-2-yl)pyrazol-3-yl]phenyl}2,4,6-trimethoxyphenylacetamide;
230. N-{4-[4-(4-methyl-7-isopropyl-1,3-benzoxazol-2-yl)pyrazol-3-yl]phenyl}2,4-dichlorophenylacetamide;
231. N-{4-[4-(4-methyl-7-isopropyl-1,3-benzoxazol-2-yl)pyrazol-3-yl]phenyl}2,5-dibromobenzamide;
232. N-{4-[4-(4-methyl-7-isopropyl-1,3-benzoxazol-2-yl)pyrazol-3-yl]phenyl}2,5-dimethoxybenzamide;
233. N-[4-[4-(1,3-naphth[2,3-d]oxazol-2-yl)pyrazol-3-yl]phenyl]2,6-dichloropyridine-4-carboxamide;
234. N-[4-[4-(1,3-naphth[2,3-d]oxazol-2-yl)pyrazol-3-yl]phenyl]2,6-dimethylbenzamide;
235. N-[4-[4-(1,3-naphth[2,3-d]oxazol-2-yl)pyrazol-3-yl]phenyl]2-acetamido-5-bromobenzamide;
236. N-[4-[4-(1,3-naphth[2,3-d]oxazol-2-yl)pyrazol-3-yl]phenyl]2-acetoxypropionamide;
237. N-[4-[4-(1,3-naphth[2,3-d]oxazol-2-yl)pyrazol-3-yl]phenyl]2-benzyloxyphenylacetamide;
238. N-[4-[4-(1,3-naphth[2,3-d]oxazol-2-yl)pyrazol-3-yl]phenyl]2-biphenylcarboxamide;
239. N-[4-[4-(1,3-naphth[2,3-d]oxazol-2-yl)pyrazol-3-yl]phenyl]2-bromo-4-fluorobenzamide;
240. N-[4-[4-(1,3-naphth[2,3-d]oxazol-2-yl)pyrazol-3-yl]phenyl]2-chloro4-methylsulfonylbenzamide;
241. N-[4-[4-(1,3-naphth[2,3-d]oxazol-2-yl)pyrazol-3-yl]phenyl]2-fluoro-6-iodobenzamide;
242. N-[4-[4-(1,3-naphth[2,3-d]oxazol-2-yl)pyrazol-3-yl]phenyl]2-fluorobenzamide;
243. N-[4-[4-(1,3-oxazole[4,5-b]pyridine2-yl)pyrazol-3-yl]phenyl]2-methoxypropionamide;
244. N-[4-[4-(1,3-oxazole[4,5-b]pyridine2-yl)pyrazol-3-yl]phenyl]2-methyl4,4,4-trifluorobutyramide;
245. N-[4-[4-(1,3-oxazole[4,5-b]pyridine2-yl)pyrazol-3-yl]phenyl]2-naphtaleneamide;
246. N-[4-[4-(1,3-oxazole[4,5-b]pyridine2-yl)pyrazol-3-yl]phenyl]3-(2-chloro-6-fluorophenyl)-5-methylisoxazole-4-carboxamide;
247. N-[4-[4-(1,3-oxazole[4,5-b]pyridine2-yl)pyrazol-3-yl]phenyl]3-(2-methoxyphenyl)propionamide;
248. N-[4-[4-(1,3-oxazole[4,5-b]pyridine2-yl)pyrazol-3-yl]phenyl]3-(2-thenoyl)-propionamide;
249. N-[4-[4-(1,3-oxazole[4,5-b]pyridine2-yl)pyrazol-3-yl]phenyl]3-(diethylamino)propionamide;
250. N-[4-[4-(1,3-oxazole[4,5-b]pyridine2-yl)pyrazol-3-yl]phenyl]3-(methylsulphonyl)benzamide;
251. N-[4-[4-(1,3-oxazole[4,5-b]pyridine2-yl)pyrazol-3-yl]phenyl]3-(phenylsulphonyl)propionamide;
252. N-[4-[4-(1,3-naphth[2,3-d]oxazol-2-yl)pyrazol-3-yl]phenyl]3,4,5-trimethoxybenzamide;
253. N-[4-[4-(1,3-naphth[2,3-d]oxazol-2-yl)pyrazol-3-yl]phenyl]3,4-diethoxybenzamide,
254. N-[4-[4-(1,3-naphth[2,3-d]oxazol-2-yl)pyrazol-3-yl]phenyl]3,4-dimethoxybenzamide;
255. N-[4-[4-(1,3-naphth[2,3-d]oxazol-2-yl)pyrazol-3-yl]phenyl]3,5-diacetamidobenzamide;
256. N-[4-[4-(1,3-naphth[2,3-d]oxazol-2-yl)pyrazol-3-yl]phenyl]3,5-dibromobenzamide;
257. N-[4-[4-(1,3-naphth[2,3-d]oxazol-2-yl)pyrazol-3-yl]phenyl]3-acetoxybenzamide;
258. N-[4-[4-(1,3-naphth[2,3-d]oxazol-2-yl)pyrazol-3-yl]phenyl]3-bromobenzamide;
259. N-[4-[4-(1,3-naphth[2,3-d]oxazol-2-yl)pyrazol-3-yl]phenyl]3-chloro-2-methylbenzamide;
260. N-[4-[4-(1,3-naphth[2,3-d]oxazol-2-yl)pyrazol-3-yl]phenyl]3-cyanobenzamide;
261. N-{3-[4-(1,3-benzoxazol-2-yl)pyrazol-3-yl]phenyl}3-fluorophenylacetamide;
262. N-{3-[4-(1,3-benzoxazol-2-yl)pyrazol-3-yl]phenyl}3-methoxycyclohexanecarboxamide;
263. N-{3-[4-(1,3-benzoxazol-2-yl)pyrazol-3-yl]phenyl}3-methyl-1-cyclohexanecarboxamide;
264. N-{3-[4-(1,3-benzoxazol-2-yl)pyrazol-3-yl]phenyl}3-methylthiopropionamide;
265. N-{3-[4-(1,3-benzoxazol-2-yl)pyrazol-3-yl]phenyl}3-pyridinepropionamide;
266. N-{3-[4-(1,3-benzoxazol-2-yl)pyrazol-3-yl]phenyl}4-(3,4-dimethoxyphenyl)butyramide;
267. N-{3-[4-(1,3-benzoxazol-2-yl)pyrazol-3-yl]phenyl}4-(dimethylamino)phenylacetamide;
268. N-{3-[4-(1,3-benzoxazol-2-yl)pyrazol-3-yl]phenyl}4-(tert-butoxymethyl)benzamide;

269. N-{3-[4-(1,3-benzoxazol-2-yl)pyrazol-3-yl]phenyl}4,5-dibromothiophene-2-carboxamide;
270. N-{3-[4-(5-chloro-1,3-benzoxazol-2-yl)pyrazol-3-yl]phenyl}4-acetamido-3-nitrobenzamide;
271. N-{3-[4-(5-chloro-1,3-benzoxazol-2-yl)pyrazol-3-yl]phenyl}4-acetamidobutyramide;
272. N-{3-[4-(5-chloro-1,3-benzoxazol-2-yl)pyrazol-3-yl]phenyl}4-biphenylcarboxamide;
273. N-{3-[4-(5-chloro-1,3-benzoxazol-2-yl)pyrazol-3-yl]phenyl}4-bromo-2-fluorobenzamide;
274. N-{3-[4-(5-chloro-1,3-benzoxazol-2-yl)pyrazol-3-yl]phenyl}4-bromo-2-methylbenzamide;
275. N-{3-[4-(5-chloro-1,3-benzoxazol-2-yl)pyrazol-3-yl]phenyl}4-bromo-3-methylbenzamide;
276. N-{3-[4-(5-chloro-1,3-benzoxazol-2-yl)pyrazol-3-yl]phenyl}4-carboxybenzenesulfonamide;
277. N-{3-[4-(5-chloro-1,3-benzoxazol-2-yl)pyrazol-3-yl]phenyl}-N'-methyl urea;
278. N-{3-[4-(5-chloro-1,3-benzoxazol-2-yl)pyrazol-3-yl]phenyl}-N'-ethyl urea;
279. N-{3-[4-(5-chloro-1,3-benzoxazol-2-yl)pyrazol-3-yl]phenyl}-N'-isopropyl urea;
280. N-{3-[4-(5-chloro-1,3-benzoxazol-2-yl)pyrazol-3-yl]phenyl}-N'-phenyl urea;
281. N-{3-[4-(5-chloro-1,3-benzoxazol-2-yl)pyrazol-3-yl]phenyl}-N'-3-chlorophenyl urea;
282. N-{3-[4-(5-chloro-1,3-benzoxazol-2-yl)pyrazol-3-yl]phenyl}-N'-4-fluorophenyl urea;
283. N-{3-[4-(5-chloro-1,3-benzoxazol-2-yl)pyrazol-3-yl]phenyl}-N'-2,4-fluorophenyl urea;
284. N-{3-[4-(5-chloro-1,3-benzoxazol-2-yl)pyrazol-3-yl]phenyl}-N'-benzyl urea;
285. N-{3-[4-(5-methyl-1,3-benzoxazol-2-yl)pyrazol-3-yl]phenyl}-N'-4-methoxyphenyl urea;
286. N-{3-[4-(5-methyl-1,3-benzoxazol-2-yl)pyrazol-3-yl]phenyl}-N'-2,6-dimethylphenyl urea;
287. N-{3-[4-(5-methyl-1,3-benzoxazol-2-yl)pyrazol-3-yl]phenyl}-N'-3-methoxyphenyl urea;
288. N-{3-[4-(5-methyl-1,3-benzoxazol-2-yl)pyrazol-3-yl]phenyl}benzenesulphonamide;
289. N-{3-[4-(5-methyl-1,3-benzoxazol-2-yl)pyrazol-3-yl]phenyl}methanesulphonamide;
290. N-{3-[4-(5-methyl-1,3-benzoxazol-2-yl)pyrazol-3-yl]phenyl}toluensulphonamide;
291. N-{3-[4-(5-methyl-1,3-benzoxazol-2-yl)pyrazol-3-yl]phenyl}ethanesulphonamide;
292. N-{3-[4-(5-methyl-1,3-benzoxazol-2-yl)pyrazol-3-yl]phenyl}acetamide;
293. N-{3-[4-(5-methyl-1,3-benzoxazol-2-yl)pyrazol-3-yl]phenyl}benzamide;
294. N-{3-[4-(5-methyl-1,3-benzoxazol-2-yl)pyrazol-3-yl]phenyl}chromone-3-carboxamide;
295. N-{3-[4-(5-methyl-1,3-benzoxazol-2-yl)pyrazol-3-yl]phenyl}cis-2-(2-thiophenecarbonyl)-1-cyclohexanecarboxamide;
296. N-{3-[4-(5-methyl-1,3-benzoxazol-2-yl)pyrazol-3-yl]phenyl}cyclobutanecarboxamide;
297. N-{3-[4-(5-methyl-1,3-benzoxazol-2-yl)pyrazol-3-yl]phenyl}cyclopentanecarboxamide;
298. N-{3-[4-(5-methyl-1,3-benzoxazol-2-yl)pyrazol-3-yl]phenyl}dicyclohexylacetamide;
299. N-{3-[4-(5-methyl-1,3-benzoxazol-2-yl)pyrazol-3-yl]phenyl}diphenylacetamide;
300. N-{3-[4-(5-tertbutyl-1,3-benzoxazol-2-yl)pyrazol-3-yl]phenyl}isoxazole-5-carboxamide;
301. N-{3-[4-(5-tertbutyl-1,3-benzoxazol-2-yl)pyrazol-3-yl]phenyl}menthyloxyacetamide;
302. N-{3-[4-(5-tertbutyl-1,3-benzoxazol-2-yl)pyrazol-3-yl]phenyl}nicotinamide;
303. N-{3-[4-(5-tertbutyl-1,3-benzoxazol-2-yl)pyrazol-3-yl]phenyl}phenylacetamide;
304. N-{3-[4-(5-tertbutyl-1,3-benzoxazol-2-yl)pyrazol-3-yl]phenyl}picolinamide;
305. N-{3-[4-(5-tertbutyl-1,3-benzoxazol-2-yl)pyrazol-3-yl]phenyl}p-tolylacetamide;
306. N-{3-[4-(5-tertbutyl-1,3-benzoxazol-2-yl)pyrazol-3-yl]phenyl}succinamide;
307. N-{3-[4-(5-tertbutyl-1,3-benzoxazol-2-yl)pyrazol-3-yl]phenyl}tert-butylacetamide;
308. N-{3-[4-(5-tertbutyl-1,3-benzoxazol-2-yl)pyrazol-3-yl]phenyl}thiophene-3-acetamide;
309. N-{3-[4-(5-tertbutyl-1,3-benzoxazol-2-yl)pyrazol-3-yl]phenyl}thiophene-3 -carboxamide;
310. N-{3-[4-(5-tertbutyl-1,3-benzoxazol-2-yl)pyrazol-3-yl]phenyl}4-chloro-alpha-methylphenylacetamide;
311. N-{3-[4-(5-tertbutyl-1,3-benzoxazol-2-yl)pyrazol-3-yl]phenyl}4-cyanobenzamide;
312. N-{3-[4-(5-tertbutyl-1,3-benzoxazol-2-yl)pyrazol-3-yl]phenyl}4-diethylaminobenzamide;
313. N-{3-[4-(5-tertbutyl-1,3-benzoxazol-2-yl)pyrazol-3-yl]phenyl}4-dimethylaminobutyramide;
314. N-{3-[4-(5,7-chloro-6-methyl-1,3-benzoxazol-2-yl)pyrazol-3-yl]phenyl}4-ethoxyphenylacetamide;
315. N-{3-[4-(5,7-chloro-6-methyl-1,3-benzoxazol-2-yl)pyrazol-3-yl]phenyl}4-iodobenzamide;
316. N-{3-[4-(5,7-chloro-6-methyl-1,3-benzoxazol-2-yl)pyrazol-3-yl]phenyl}4-iodophenylacetamide;
317. N-{3-[4-(5,7-chloro-6-methyl-1,3-benzoxazol-2-yl)pyrazol-3-yl]phenyl}4-isopropylphenoxyacetamide;
318. N-{3-[4-(5,7-chloro-6-methyl-1,3-benzoxazol-2-yl)pyrazol-3-yl]phenyl}4-methyl-3-nitrobenzamide;
319. N-{3-[4-(5,7-chloro-6-methyl-1,3-benzoxazol-2-yl)pyrazol-3-yl]phenyl}5-(2-thienyl)pentanamide;
320. N-{3-[4-(5,7-chloro-6-methyl-1,3-benzoxazol-2-yl)pyrazol-3-yl]phenyl}5,6 -dichloronicotinamide;
321. N-{3-[4-(5,7-chloro-6-methyl-1,3-benzoxazol-2-yl)pyrazol-3-yl]phenyl}5-acetamido-2-nitrobenzamide;
322. N-{3-[4-(5,7-chloro-6-methyl-1,3-benzoxazol-2-yl)pyrazol-3-yl]phenyl}5-benzoylpentanamide;
323. N-{3-[4-(5,7-chloro-6-methyl-1,3-benzoxazol-2-yl)pyrazol-3-yl]phenyl}5-bromo-3-pyridylacetamide;
324. N-{3-[4-(5-ethylsulfonyl-1,3-benzoxazol-2-yl)pyrazol-3-yl]phenyl}5-chlorothianaphthene-3-acetamide;
325. N-{3-[4-(5-ethylsulfonyl-1,3-benzoxazol-2-yl)pyrazol-3-yl]phenyl}5-methyl-1-phenylpyrazole-4-carboxamide;
326. N-{3-[4-(5-ethylsulfonyl-1,3-benzoxazol-2-yl)pyrazol-3-yl]phenyl}5-methylhexanamide;
327. N-{3-[4-(5-ethylsulfonyl-1,3-benzoxazol-2-yl)pyrazol-3-yl]phenyl}5-methylisoxazole-4-carboxamide;
328. N-{3-[4-(5-ethylsulfonyl-1,3-benzoxazol-2-yl)pyrazol-3-yl]phenyl}6-acetoxy-2-naphtaleneamide;
329. N-{3-[4-(5-ethylsulfonyl-1,3-benzoxazol-2-yl)pyrazol-3-yl]phenyl}6-cyanonicotinamide;
330. N-{3-[4-(5-ethylsulfonyl-1,3-benzoxazol-2-yl)pyrazol-3-yl]phenyl}7-chloro-1-ethyl-6-fluoro-4-oxohydroquinoline-3-carboxamide;
331. N-{3-[4-(5-ethylsulfonyl-1,3-benzoxazol-2-yl)pyrazol-3-yl]phenyl}-N'-methyl urea;
332. N-{3-[4-(5-ethylsulfonyl-1,3-benzoxazol-2-yl)pyrazol-3-yl]phenyl}-N'-ethyl urea;
333. N-{3-[4-(5-ethylsulfonyl-1,3-benzoxazol-2-yl)pyrazol-3-yl]phenyl}-N'-isopropyl urea;

334. N-{3-[4-(5-phenyl-1,3-benzoxazol-2-yl)pyrazol-3-yl]phenyl}-N'-phenyl urea;
335. N-{3-[4-(5-phenyl-1,3-benzoxazol-2-yl)pyrazol-3-yl]phenyl}-N'-3-chlorophenyl urea;
336. N-{3-[4-(5-phenyl-1,3-benzoxazol-2-yl)pyrazol-3-yl]phenyl}-N'-4-fluorophenyl urea;
337. N-{3-[4-(5-phenyl-1,3-benzoxazol-2-yl)pyrazol-3-yl]phenyl}-N'-2,4-fluorophenyl urea;
338. N-{3-[4-(5-phenyl-1,3-benzoxazol-2-yl)pyrazol-3-yl]phenyl}-N'-benzyl urea;
339. N-{3-[4-(5-phenyl-1,3-benzoxazol-2-yl)pyrazol-3-yl]phenyl}-N'-4-methoxyphenyl urea;
340. N-{3-[4-(5-phenyl-1,3-benzoxazol-2-yl)pyrazol-3-yl]phenyl}-N'-2,6-dimethylphenyl urea;
341. N-{3-[4-(5-phenyl-1,3-benzoxazol-2-yl)pyrazol-3-yl]phenyl}-N'-3-methoxyphenyl urea;
342. N-{3-[4-(5-phenyl-1,3-benzoxazol-2-yl)pyrazol-3-yl]phenyl}benzenesulphonamide;
343. N-{3-[4-(5-phenyl-1,3-benzoxazol-2-yl)pyrazol-3-yl]phenyl}methanesulphonamide;
344. N-{3-[4-(4-methyl-7-isopropyl-1,3-benzoxazol-2-yl)pyrazol-3-yl]phenyl}toluensulphonamide;
345. N-{3-[4-(4-methyl-7-isopropyl-1,3-benzoxazol-2-yl)pyrazol-3-yl]phenyl}ethanesulphonamide;
346. N-{3-[4-(4-methyl-7-isopropyl-1,3-benzoxazol-2-yl)pyrazol-3-yl]phenyl}acetamide;
347. N-{3-[4-(4-methyl-7-isopropyl-1,3-benzoxazol-2-yl)pyrazol-3-yl]phenyl}benzamide;
348. N-{3-[4-(4-methyl-7-isopropyl-1,3-benzoxazol-2-yl)pyrazol-3-yl]phenyl}chromone-3-carboxamide;
349. N-{3-[4-(4-methyl-7-isopropyl-1,3-benzoxazol-2-yl)pyrazol-3-yl]phenyl}cis-2-(2-thiophenecarbonyl)-1-cyclohexanecarboxamide;
350. N-{3-[4-(4-methyl-7-isopropyl-1,3-benzoxazol-2-yl)pyrazol-3-yl]phenyl}cyclobutanecarboxamide;
351. N-{3-[4-(4-methyl-7-isopropyl-1,3-benzoxazol-2-yl)pyrazol-3-yl]phenyl}cyclopentanecarboxamide;
352. N-{3-[4-(4-methyl-7-isopropyl-1,3-benzoxazol-2-yl)pyrazol-3-yl]phenyl}dicyclohexylacetamide;
353. N-{3-[4-(4-methyl-7-isopropyl-1,3-benzoxazol-2-yl)pyrazol-3-yl]phenyl}diphenylacetamide;
354. N-[3-[4-(1,3-naphth[2,3-d]oxazol-2-yl)pyrazol-3-yl]phenyl]isoxazole-5-carboxamide;
355. N-[3-[4-(1,3-naphth[2,3-d]oxazol-2-yl)pyrazol-3-yl]phenyl]menthyloxyacetamide;
356. N-[3-[4-(1,3-naphth[2,3-d]oxazol-2-yl)pyrazol-3-yl]phenyl]nicotinamide;
357. N-[3-[4-(1,3-naphth[2,3-d]oxazol-2-yl)pyrazol-3-yl]phenyl]phenylacetamide;
358. N-[3-[4-(1,3-naphth[2,3-d]oxazol-2-yl)pyrazol-3-yl]phenyl]picolinamide;
359. N-[3-[4-(1,3-naphth[2,3-d]oxazol-2-yl)pyrazol-3-yl]phenyl]p-tolylacetamide;
360. N-[3-[4-(1,3-naphth[2,3-d]oxazol-2-yl)pyrazol-3-yl]phenyl]succinamide;
361. N-[3-[4-(1,3-naphth[2,3-d]oxazol-2-yl)pyrazol-3-yl]phenyl]tert-butylacetamide;
362. N-[3-[4-(1,3-naphth[2,3-d]oxazol-2-yl)pyrazol-3-yl]phenyl]thiophene-3-acetamide;
363. N-[3-[4-(1,3-oxazole[4,5-b]pyridine2-yl)pyrazol-3-yl]phenyl]thiophene-3-carboxamide;
364. N-[3-[4-(1,3-oxazole[4,5-b]pyridine2-yl)pyrazol-3-yl]phenyl]2-(2-methoxyethoxy)acetamide;
365. N-[3-[4-(1,3-oxazole[4,5-b]pyridine2-yl)pyrazol-3-yl]phenyl]2-(4-chlorobenzoyl)benzamide;
366. N-[3-[4-(1,3-oxazole[4,5-b]pyridine2-yl)pyrazol-3-yl]phenyl]2-(4-nitrophenyl)propionamide;
367. N-[3-[4-(1,3-oxazole[4,5-b]pyridine2-yl)pyrazol-3-yl]phenyl]2-(4-pyridyl)thiazole-4-carboxamide;
368. N-[3-[4-(1,3-oxazole[4,5-b]pyridine2-yl)pyrazol-3-yl]phenyl]2-(benzyloxycarbonylamino)-4-cyclohexene-1-carboxamide;
369. N-[3-[4-(1,3-oxazole[4,5-b]pyridine2-yl)pyrazol-3-yl]phenyl]2-(benzyloxycarbonylamino)-cyclohexanecarboxamide;
370. N-[3-[4-(1,3-oxazole[4,5-b]pyridine2-yl)pyrazol-3-yl]phenyl]2,2,3,3-tetramethylcyclopropanecarboxamide;
371. N-[3-[4-(1,3-oxazole[4,5-b]pyridine2-yl)pyrazol-3-yl]phenyl]2,2-dimethyl-4-pentenamide;
372. N-[3-[4-(1,3-oxazole[4,5-b]pyridine2-yl)pyrazol-3-yl]phenyl]2,2-dimethylhexanamide;
373. N-[3-[4-(1,3-naphth[2,3-d]oxazol-2-yl)pyrazol-3-yl]phenyl]2,3-dichlorophenoxyacetamide;
374. N-[3-[4-(1,3-naphth[2,3-d]oxazol-2-yl)pyrazol-3-yl]phenyl]2,4,6-trimethoxyphenylacetamide;
375. N-[3-[4-(1,3-naphth[2,3-d]oxazol-2-yl)pyrazol-3-yl]phenyl]2,4-dichlorophenylacetamide;
376. N-[3-[4-(1,3-naphth[2,3-d]oxazol-2-yl)pyrazol-3-yl]phenyl]2,5-dibromobenzamide;
377. N-[3-[4-(1,3-naphth[2,3-d]oxazol-2-yl)pyrazol-3-yl]phenyl]2,5-dimethoxybenzamide;
378. N-[3-[4-(1,3-naphth[2,3-d]oxazol-2-yl)pyrazol-3-yl]phenyl]2,6-dichloropyridine-4-carboxamide;
379. N-[3-[4-(1,3-naphth[2,3-d]oxazol-2-yl)pyrazol-3-yl]phenyl]2,6-dimethylbenzamide;
380. N-[3-[4-(1,3-naphth[2,3-d]oxazol-2-yl)pyrazol-3-yl]phenyl]2-acetamido-5-bromobenzamide;
381. N-[3-[4-(1,3-naphth[2,3-d]oxazol-2-yl)pyrazol-3-yl]phenyl]2-acetoxypropionamide;
382. N-[3-[4-(1,3-naphth[2,3-d]oxazol-2-yl)pyrazol-3-yl]phenyl]2-benzyloxyphenylacetamide.

8. A process for preparing a compound as defined in claim 1, which process comprises:
a) reacting the compound of formula (II) with a suitable nitrogen-pyrazole protecting agent or a solid support

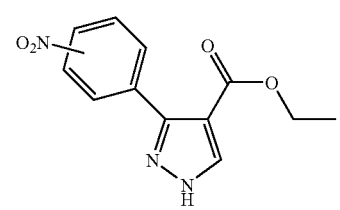
(II)

so as to obtain a compound of formula (III)

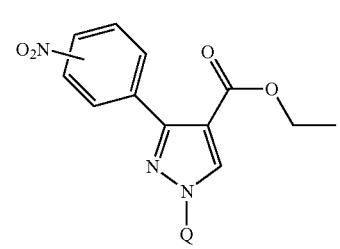
(III)

wherein Q is a nitrogen-pyrazole protecting agent or a solid support;

b) reacting the compound of formula (III) under basic conditions so as to obtain the compound of formula (IV)

(IV)

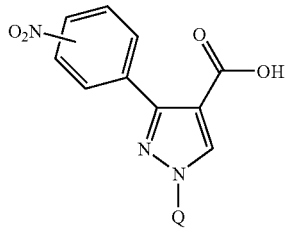

wherein Q is as above defined;

c) reacting the compound of formula (IV) with a derivative of formula (V)

(V)

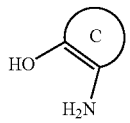

so as to obtain a compound of formula (VI)

(VI)

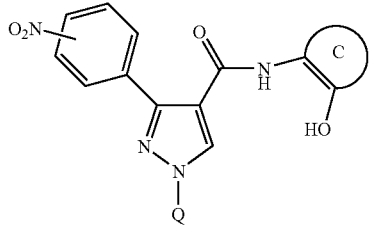

wherein Q and C are as above defined;

d) reacting the compound of formula (VI) with a suitable azodicarboxylate derivative and a phosphine so as to obtain the compound of formula (VII)

(VII)

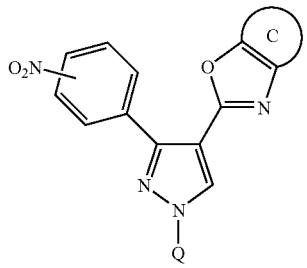

wherein Q and C are as above defined;

e) reducing the compound of formula (VII) so as to obtain the compound of formula (VIII)

(VIII)

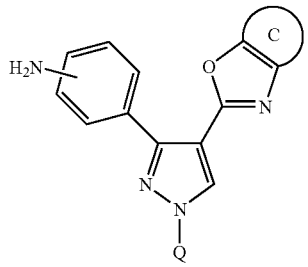

wherein Q and C are as above defined;

f) reacting the compound of formula (VIII) with any one of the compounds of formula (IX), (X) or (XI)

R—COX (IX),

R—SO$_2$X' (X),

R—NCO (XI)

wherein R is as above defined, X is hydroxy or a suitable leaving group and X' is a suitable leaving group, so as to obtain the compound of formula (XII)

(XII)

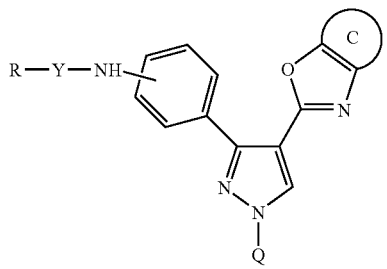

wherein R, Q and C are as above defined and Y is a divalent group selected among (>C=O), (—SO$_2$—) or (—NHCO—); or, alternatively, reacting under reductive conditions the compound of formula (VIII) with a suitable aldehyde or ketone derivative of formula (XIII)

R'—CO—R" (XIII)

wherein R' and R" have the meanings reported for R, provided they are not both hydrogen atoms, so as to obtain the compound of formula (XII) wherein Q and C are as above defined, Y is a single bond and R is a group —CH(R')(R");

or, alternatively, reacting the compound of formula (VIII) with a suitable acylating agent in the presence of ammonia, so as to obtain the compound of formula (XII) wherein Q and C are as above defined, Y is aminocarbonyl (—NHCO—) and R is hydrogen;

g) deprotecting the compound of formula (XII) under acidic conditions so as to obtain the compound of formula (I) and, if desired, converting the said compound of formula (I) into another compound of formula (I) and/or into a salt thereof.

9. The process of claim 8 wherein, in step a), Q is a suitable nitrogen-pyrazole protecting group or a solid support selected from tert-butoxycarbonyl (BOC), di-tert-butyl dicarbonate, 2-(tert-butoxycarbonyloxymino)-2-phenylacetonitrile, chlorotriphenylmethane, trityl, a trityl chloride resin or a chlorotrityl chloride resin.

10. The process of claim 9 wherein the trityl chloride or chlorotrityl chloride resin is a polystyrene resin.

11. The process of claim 8 wherein, in step b), basic conditions comprise the use of sodium, potassium or lithium hydroxide.

12. The process of claim 8 wherein, in step d), the azodicarboxylate derivative is selected from diethyl azodicarboxylate, diisopropyl azodicarboxylate or di-tert-butyl azodicarboxylate.

13. The process of claim 8 wherein, in step d), the phosphine is selected from triphenylphosphine, tri-n-butylphosphine, tricyclohexylphosphine or triethylphosphine.

14. The process of claim 8 wherein, in step e), the compound of formula (VII) is converted into the corresponding amino derivative of formula (VIII) in the presence of a reducing agent selected from tin (II) chloride, sodium borohydride, sodium dithionite, ammonium formate or chromium (II) chloride.

15. The process of claim 8 wherein, in step f), the compound of formula (VIII) is reacted with a compound of formula (IX) wherein X is hydroxy, chlorine or bromine.

16. The process of claim 8 wherein, in step f), the compound of formula (VIII) is reacted with a compound of formula (X) wherein X' is chlorine or bromine.

17. The process of claim 8 wherein, in step f), the compound of formula (VIII) is reacted with the compound of formula (XIII) under reductive conditions comprising the use of sodium borohydride, sodium cyanoborohydride or sodium triacetoxyborohydride.

18. The process of claim 8 wherein, in step f), the compound of formula (VIII) is reacted with a suitable acylating agent selected from trisphosgene or trichloromethyl chloroformate, in the presence of ammonia.

19. The process of claim 8 wherein, in step g), the acidic conditions comprise the use of an acid selected from hydrochloric, trifluoroacetic, methanesulphonic or p-toluensulphonic acid or of an acid ion exchange resin.

20. The compound of formula (VIII) optionally in the form of a pharmaceutically acceptable salt

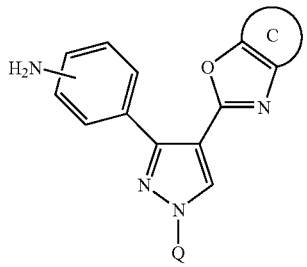

(VIII)

wherein Q and C are as defined in claim 8.

21. A library of two or more compounds selected from oxazolyl-pyrazole derivatives of formula (I)

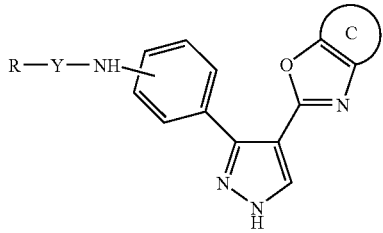

(I)

wherein
R represents a hydrogen atom; a straight or branched $C_1$–$C_8$ alkyl group; a straight or branched $C_2$–$C_8$ alkenyl group; an aryl or aryl $C_1$–$C_6$ alkyl group; a saturated or unsaturated $C_3$–$C_6$ cycloalkyl or cycloalkyloxy group optionally further condensed with 1 or 2 benzene rings; or it is an optionally benzocondensed 5 or 6 membered heterocyclic or heterocyclyl $C_1$–$C_6$ alkyl group, having 1 or 2 heteroatoms selected among nitrogen, oxygen or sulfur; each of the above defined R groups being optionally further substituted by one or more groups selected from:
i) halogen, nitro, cyano, hydroxy, oxo groups (=O);
ii) straight or branched $C_1$–$C_6$ alkyl, alkoxyalkyl or perfluorinated alkyl;
iii) aryl or 5 or 6 membered heterocycles having 1 or 2 heteroatoms selected among nitrogen, oxygen or sulfur, optionally substituted by halogen, nitro, cyano, $C_1$–$C_6$ alkyl or alkoxy;
iv) straight or branched $C_1$–$C_6$ alkoxy, alkoxyalkyloxy, arylalkyloxy or aryloxy optionally substituted by halogen, nitro, cyano, $C_1$–$C_6$ alkyl or alkoxy;
v) straight or branched $C_1$–$C_6$ alkylthio or alkylsulphonyl, arylthio or arylsulphonyl;
vi) $C_3$–$C_6$ cycloalkyl;
vii) amino, $C_1$–$C_6$alkylamino, dialkylamino or arylamino;
viii) $C_1$–$C_6$ alkylcarbonyl, alkyloxycarbonyl, alkylaminocarbonyl, aminocarbonyl, arylcarbonyl or heterocyclylcarbonyl optionally substituted by halogen, nitro, cyano, $C_1$–$C_6$ alkyl or alkoxy;
ix) $C_1$–$C_6$ alkylcarbonylamino, alkyloxycarbonylamino, arylalkyloxycarbonylamino, arylcarbonylamino or aryloxycarbonylamino;
x) carboxy, $C_1$–$C_6$ alkylcarbonyloxy or arylcarbonyloxy;
Y is a single bond or a divalent group selected from carbonyl (>C=O), aminocarbonyl (—NHCO—) or sulphonyl (—$SO_2$—);
C is benzene, naphthalene or an optionally benzocondensed 5 or 6 membered heterocycle having 1 or 2 heteroatoms selected among nitrogen, oxygen or sulphur; each of which being optionally further substituted by one or more groups selected from halogen, nitro, cyano, straight or branched $C_1$–$C_6$ alkyl or alkoxy, alkylsulphonyl or aryl groups;
and the pharmaceutically acceptable salts thereof.

22. A compound as defined in claim 1 which is obtainable by a combinatorial chemical process comprising reacting any of the amino derivatives of formula (VIII) with any one of the carboxylic acid derivatives of formula (IX) and by subsequently operating as per the process of claim 8.

23. A compound as defined in claim 1 which is obtainable by a combinatorial chemical process comprising reacting any of the amino derivatives of formula (VIII) with any one of the isocyanate derivatives of formula (XI) and by subsequently operating as per the process of claim 8.

24. A compound as defined in claim 1 which is obtainable by a combinatorial chemical process comprising reacting any of the amino derivatives of formula (VIII) with any one of the sulphonyl chloride derivatives of formula (X) and by subsequently operating as per the process of claim 8.

25. A pharmaceutical composition comprising an effective amount of a compound as defined in claim 1, and at least one pharmaceutically acceptable excipient, carrier or diluent.

26. A pharmaceutical composition according to claim 25 further comprising one or more chemotherapeutic agents, as a combined preparation for simultaneous, separate or sequential use in anticancer therapy.

27. A product or kit comprising a compound as defined in claim 1 or a pharmaceutical composition thereof as defined in claim 25, and one or more chemotherapeutic agents, as a combined preparation for simultaneous, separate or sequential use in anticancer therapy.

* * * * *